(12) United States Patent
Masuda et al.

(10) Patent No.: US 11,763,449 B2
(45) Date of Patent: Sep. 19, 2023

(54) SYSTEMS AND METHODS FOR GENERATING AND APPLYING MATRIX IMAGES TO MONITOR CARDIAC DISEASE

(71) Applicant: Zoll Medical Corporation, Chelmsford, MA (US)

(72) Inventors: Tsuyoshi Masuda, Pittsburgh, PA (US); Kent Volosin, Mars, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 361 days.

(21) Appl. No.: 16/938,244

(22) Filed: Jul. 24, 2020

(65) Prior Publication Data
US 2022/0028060 A1    Jan. 27, 2022

(51) Int. Cl.
*A61B 5/00*    (2006.01)
*G06T 7/00*    (2017.01)
(Continued)

(52) U.S. Cl.
CPC .......... *G06T 7/0012* (2013.01); *A61B 5/0006* (2013.01); *A61B 5/282* (2021.01);
(Continued)

(58) Field of Classification Search
CPC ....... A61B 5/0006; A61B 5/282; A61B 5/316; A61B 5/352; A61B 5/4842; A61B 5/7264; A61B 7/00
See application file for complete search history.

(56) References Cited

U.S. PATENT DOCUMENTS 8,668,644 B2    3/2014    Ong et al.
9,420,957 B2    8/2016    Ong et al.
(Continued)

FOREIGN PATENT DOCUMENTS

CN    110236518 A  *  9/2019
WO    1998039061    9/1998
(Continued)

OTHER PUBLICATIONS

Li, et al., Electrocardiomatrix: A new method for beat-by-beat visualization and inspection of cardiac signals, Journal of Integrative Cardiology, vol. 1, Issue 5, Sep. 24, 2015, pp. 124-128.
(Continued)

*Primary Examiner* — Allen Porter
*Assistant Examiner* — Laura N Hodge
(74) *Attorney, Agent, or Firm* — Gardella Grace P.A.

(57) ABSTRACT

Systems and methods are provided for monitoring progression of a cardiac disease in a patient by providing cardio-vibrational image matrixes and/or ECG image matrices generated using sensor data supplied by a medical device. In some examples, cardio-vibrational image matrices and/or ECG image matrices are output as image files. In some implementations, systems and methods are provided for using such cardio-vibrational image matrices and/or an ECG image matrices, and/or other clinical information, using machine learning classifiers, to assess cardiac risk in a patient. In some implementations, systems and methods are provided for using cardio-vibrational image matrixes and/or ECG image matrices, and/or other clinical information for real-time analysis of cardiac risk.

30 Claims, 18 Drawing Sheets
(5 of 18 Drawing Sheet(s) Filed in Color)

(51) Int. Cl.
- *A61B 5/282* (2021.01)
- *A61B 5/352* (2021.01)
- *A61B 5/316* (2021.01)
- *G06T 5/00* (2006.01)
- *A61B 7/00* (2006.01)
- *A61N 1/39* (2006.01)
- *A61B 5/361* (2021.01)
- *A61B 5/363* (2021.01)
- *A61B 7/04* (2006.01)

(52) U.S. Cl.
CPC .............. *A61B 5/316* (2021.01); *A61B 5/352* (2021.01); *A61B 5/4842* (2013.01); *A61B 5/7264* (2013.01); *A61B 7/00* (2013.01); *G06T 5/002* (2013.01); *A61B 5/361* (2021.01); *A61B 5/363* (2021.01); *A61B 7/04* (2013.01); *A61B 2562/0219* (2013.01); *A61N 1/3904* (2017.08); *G06T 2207/20081* (2013.01); *G06T 2207/30048* (2013.01)

(56) References Cited

U.S. PATENT DOCUMENTS

| | | | |
|---|---|---|---|
| 9,918,651 | B2 | 3/2018 | Borjigin et al. |
| 2012/0293323 | A1 | 11/2012 | Kaib et al. |
| 2014/0005738 | A1 | 1/2014 | Jorgenson et al. |
| 2014/0107541 | A1 | 4/2014 | Sullivan et al. |
| 2015/0065815 | A1 | 3/2015 | Najarian et al. |
| 2016/0000349 | A1* | 1/2016 | Sullivan ............... A61B 5/7221 600/509 |
| 2016/0058318 | A1 | 3/2016 | Borjigin et al. |
| 2016/0135706 | A1 | 5/2016 | Sullivan et al. |
| 2019/0059748 | A1* | 2/2019 | Kaiser .................... A61B 7/026 |
| 2019/0223839 | A1 | 7/2019 | Shute et al. |
| 2021/0137391 | A1 | 5/2021 | Mak |

FOREIGN PATENT DOCUMENTS

| | | |
|---|---|---|
| WO | 2019142119 | 7/2019 |
| WO | 2022020040 | 1/2022 |

OTHER PUBLICATIONS

Lee, et al., Accurate Detection of Atrial Fibrillation and Atrial Flutter Using the Electrocardiomatrix Technique, Journal of Electrocardiology, vol. 51, Issue 6, Nov.-Dec. 2018, pp. S121-S125.

Xu, et al., Electrocardiomatrix Facilitates Qualitative Identification of Diminished Heart Rate Variability in Critically Ill Patients Shortly Before Cardiac Arrest, Journal of Electrocardiology, vol. 51, Issue 6, Nov.-Dec. 2018, pp. 955-961.

Hannun, et al., Cardiologist-Level Arrhythmia Detection and Classification in Ambulatory Electrocardiograms Using a Deep Neural Network, Nature Medicine, vol. 25, Jan. 7, 2019, pp. 65-69.

Attia, et al., Screening for Cardiac Contractile Dysfunction Using an Artificial Intelligence-Enabled Electrocardiogram, Nature Medicine, vol. 25, Issue 1, Jan. 7, 2019, pp. 70-74.

Xiao, et al., A Deep Learning Approach to Examine Ischemic ST Changes in Ambulatory ECG Recordings, AMIA Joint Summits on Translational Science Proceedings, May 8, 2018, pp. 256-262.

International Search Report and Written Opinion for International Application No. PCT/US2021/037687 dated Oct. 13, 2021.

International Preliminary Report on Patentability for International Application No. PCT/US2021/037867 dated Feb. 2, 2023.

* cited by examiner

SYSTEMS AND METHODS FOR GENERATING AND APPLYING MATRIX IMAGES TO MONITOR CARDIAC DISEASE

BACKGROUND

Electrical shock therapy to the heart was developed to rapidly and effectively terminate potentially lethal cardiac arrhythmias. There are 2 main types of electrical shock therapy. Cardioversion is an electric shock timed to the underlying heartbeat. Defibrillation is an electric shock not timed to the heart's electrical signal.

There are many different kinds of heart rhythms, some of which an electrical shock is appropriate treatment ("shockable rhythm") and some of them a shock would not be appropriate treatment ("non-shockable rhythm"). For example, normal sinus rhythm is a person's normal heart rhythm. There are, however, many abnormal rhythms that could not be treated with an electrical shock. There are also some abnormal rhythms that do not benefit from shocks even though they are potentially lethal arrhythmias, which means that the patient cannot remain alive with the rhythm, but yet applying shocks will not help convert the rhythm.

As an example of a non-shockable rhythm, if a patient experiences asystole (the absence of a heartbeat), application of shocks will be ineffective. Pacing the heart, for example, would be one treatment for asystole. Electrical shocks are also not recommended for the treatment of bradycardias, during which the heart beats too slowly, even though this could be lethal. Electro-mechanical dissociation (EMD), in which there is electrical activity in the heart but it is not making the heart muscle contract, is non-shockable and non-viable, and would require CPR as a first response. Idio-ventricular rhythms, in which the normal electrical activity occurs in the ventricles but not the atria, can also be non-shockable and non-viable. Idio-ventricular rhythms can result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles.

The primary examples of shockable rhythms, for which a first responder or automated defibrillation system should perform defibrillation, include ventricular fibrillation, ventricular tachycardia, and ventricular flutter.

Some conventional medical devices that monitor the cardiopulmonary system obtain a subject's electrocardiogram (ECG) signal from body surface electrodes. Known ambulatory wearable defibrillators, such as the LifeVest® Wearable Cardioverter Defibrillator available from ZOLL Medical Corporation of Chelmsford, Mass., use four ECG sensing electrodes in a dual-channel bipolar configuration. This arrangement of ECG sensing electrodes is usually suitable because in most cases it is rare that noise or electrode movement affects the entire body circumference. The dual-channel bipolar configuration provides redundancy and allows the system to operate on a single channel if necessary. Because signal quality also varies from subject to subject, having two channels provides the opportunity to have improved signal pickup, since the ECG sensing electrodes are located in different body positions.

Heart rhythms may also be monitored using vibrational sensors (e.g., including acoustic sensors and/or audio transducers) to detect and record cardio-vibrational signals and the timing of the cardio vibrations, including any one or all of S1, S2, S3, and S4 cardio vibrations. Other cardio-vibrational parameters which may be monitored by recording cardio-vibrational signals include electromechanical activation time (EMAT), percentage of EMAT (% EMAT), systolic dysfunction index (SDI), and left ventricular systolic time (LVST). EMAT is generally measured from the onset of the Q wave on the ECG to the closure of the mitral valve within the S1 cardio vibration. Prolonged EMAT has been associated with reduced left ventricular ejection fraction (LVEF, being a measure of how much blood is being pumped out of the left ventricle of the heart with each contraction). % EMAT is EMAT corrected for heart rate. % EMAT is related to the efficiency of the pump function of the heart. SDI is a multiplicative combination of ECG and sound parameters (EMAT, S3, QRS duration, and QR interval). SDI predicts left ventricular systolic dysfunction with high specificity. LVST is defined as the time interval between the S1 and the S2 cardio vibrations. It is the systolic portion of the cardiac cycle. LVST has some heart rate dependence and tends to be approximately 40% (range 30-50%) of the cardiac cycle but is affected by disease that produces poor contractility and/or a low ejection fraction.

SUMMARY OF ILLUSTRATIVE EMBODIMENTS

In one aspect, the present disclosure relates to a method for monitoring a progression of a cardiac disease in a patient by providing cardio-vibrational image matrixes generated using sensor data supplied by a medical device. The method may include: accessing a number of cardio-vibrational signals obtained by at least one vibrational sensor monitoring a heart of the patient; generating, by processing circuitry from the number of cardio-vibrational signals, cardio-vibrational measurements of a predetermined duration, the cardio-vibrational measurements including at least a number of S1 peaks and a number of S2 peaks; and transforming, by the processing circuitry, the cardio-vibrational measurements of the predetermined duration into a cardio-vibrational image matrix. Transforming may include segmenting the cardio-vibrational measurements of the predetermined duration into a number of adjacent cardiac portions each having a duration smaller than the predetermined duration, and plotting the number of adjacent cardiac portions using a number of pixel characteristic values mapped to parameter values of corresponding cardio-vibrational measurements to produce the cardio-vibrational image matrix. Plotting may include, on one axis, a time progression of the number of adjacent cardiac portions, and on another axis, the pixel characteristic values of each portion of the number of adjacent cardiac portions, where the pixel characteristic values of each respective portion include values representing at least an S1 parameter value corresponding to a respective S1 peak of the number of S1 peaks, and an S2 parameter value corresponding to a respective S2 peak of the number of S2 peaks, such that the cardio-vibrational image matrix represents, along the time progression of the number of adjacent cardiac portions, visible differences in timing and/or intensity of at least the S1 parameter values of the cardiac portions and the S2 parameter values of the cardiac portions. The method may include outputting the cardio-vibrational image matrix as an image file for use in monitoring the progression of the cardiac disease in the patient.

The characteristic values may include at least one of a pixel intensity or a pixel hue. The parameter values may include at least one of an amplitude, a phase, or a magnitude. The predetermined duration may include at least one of around 15 seconds, around 30 seconds, around 45 seconds, around 90 seconds, around 120 seconds, around 2 minutes, around 3 minutes, or around 10 minutes. The predetermined duration may include at least one of between around 15 seconds and around 30 seconds, between around 30 seconds and around 45 seconds, between around 45 seconds and around 60 seconds, between around 60 seconds and around 90 seconds, between around 90 seconds and 120 seconds, between around 2 minutes or around 3 minutes, or between around 3 minutes and around 10 minutes. The duration smaller than the predetermined duration may include at least one of around 100 milliseconds, around 1000 milliseconds, around 1 second, around 2 seconds, around 5 seconds, or around 10 seconds. The duration smaller than the predetermined duration may include at least one of between around 1 millisecond and around 100 milliseconds, between 100 milliseconds and around 1000 milliseconds, between around 1 second and around 2 seconds, between around 2 seconds and around 5 seconds, or between around 5 seconds and around 10 seconds.

In some embodiments, each portion of the number of adjacent cardiac portions includes at least two S1 peaks of the number of S1 peaks and at least two S2 peaks of the number of S2 peaks. Plotting the number of adjacent cardiac portions may include plotting the pixel characteristic values of each portion vertically along a y-axis and plotting the time progression of the number of adjacent cardiac portions horizontally along an x-axis. The cardio-vibrational image matrix may represent, along the x-axis, visible differences in timing and/or pixel characteristic values of a portion of the number of S1 peaks and a portion of the number of S2 peaks.

In some embodiments, the method includes, prior to transforming, registering, by the processing circuitry, a time scale of the cardio-vibrational measurements of the predetermined duration with a number of R-peaks of an ECG reading of the patient obtained during the predetermined duration, where segmenting includes segmenting at least in part according to the registering. The method may include applying, by the processing circuitry to the cardio-vibrational image matrix, a smoothing algorithm to proximately located pixel characteristic values of the number of pixel characteristic values in the cardio-vibrational image matrix. The number of pixel characteristic values may include between around at least 3 and 16 different colors. The cardio-vibrational measurements may include a number of S3 peaks.

In some embodiments, the medical device includes a wearable cardiac monitoring device. The wearable cardiac medical device may include a cardiac holter monitor and associated number of ECG electrodes. The medical device may include a cardiac monitoring and treatment device. The cardiac monitoring and treatment device may include an automated external defibrillator. The cardiac monitoring and treatment device may include a wearable cardioverter defibrillator.

In some embodiments, the method includes transmitting, by the processing circuitry, the cardio-vibrational image matrix to a remote server. The method may include applying, by the processing circuitry, the cardio-vibrational image matrix to a machine learning classifier to determine an arrhythmia condition in the patient, where the machine learning classifier is trained to identify at least an existence and a nonexistence of an arrhythmia condition in ECG image matrices. The method may include applying, by the processing circuitry, the cardio-vibrational image matrix to at least one machine learning classifier to determine a present classification of a number of classifications of at least one cardiac risk biomarker, and generating, by the processing circuitry using the present classification, a prediction of future potential outcome related to the at least one cardiac risk biomarker.

In one aspect, the present disclosure relates to a system for monitoring a progression of a cardiac disease in a patient by providing cardio-vibrational image matrixes generated using sensor data supplied by a medical device. The system may include a non-volatile computer readable storage medium configured to store a number of cardio-vibrational measurements, and operations stored as computer executable instructions to a non-transitory computer readable media and/or encoded in hardware logic. The operations may be configured to access a number of cardio-vibrational signals obtained by at least one vibrational sensor monitoring a heart of the patient, generate, from the number of cardio-vibrational signals, cardio-vibrational measurements of a predetermined duration, the cardio-vibrational measurements including at least a number of S1 peaks and a number of S2 peaks, where the cardio-vibrational measurements are stored to the non-volatile computer readable storage medium, and transform the cardio-vibrational measurements of the predetermined duration into a cardio-vibrational image matrix. Transforming may include segmenting the cardio-vibrational measurements of the predetermined duration into a number of adjacent cardiac portions each having a duration smaller than the predetermined duration, and plotting the number of adjacent cardiac portions using a number of pixel characteristic values mapped to parameter values of corresponding cardio-vibrational measurements to produce the cardio-vibrational image matrix. Plotting may include, on one axis, a time progression of the number of adjacent cardiac portions, and on another axis, the pixel characteristic values of each portion of the number of adjacent cardiac portions, where the pixel characteristic values of each respective portion include values representing at least an S1 parameter value corresponding to a respective S1 peak of the number of S1 peaks, and an S2 parameter value corresponding to a respective S2 peak of the number of S2 peaks, such that the cardio-vibrational image matrix represents, along the time progression of the number of adjacent cardiac portions, visible differences in timing and/or intensity of at least the S1 parameter values of the cardiac portions and the S2 parameter values of the cardiac portions. The operations may be configured to output the cardio-vibrational image matrix as an image file for use in monitoring the progression of the cardiac disease in the patient.

In some embodiments, the characteristic values include at least one of a pixel intensity or a pixel hue. The parameter values may include at least one of an amplitude, a phase, or a magnitude. The predetermined duration may include at least one of around 15 seconds, around 30 seconds, around 45 seconds, around 90 seconds, around 120 seconds, around 2 minutes, around 3 minutes, or around 10 minutes. The predetermined duration may include at least one of between around 15 seconds and around 30 seconds, between around 30 seconds and around 45 seconds, between around 45 seconds and around 60 seconds, between around 60 seconds and around 90 seconds, between around 90 seconds and 120 seconds, between around 2 minutes or around 3 minutes, or between around 3 minutes and around 10 minutes. The duration smaller than the predetermined duration may include at least one of around 100 milliseconds, around 1000 milliseconds, around 1 second, around 2 seconds, around 5 seconds, or around 10 seconds. The duration smaller than the predetermined duration may include at least one of between around 1 millisecond and around 100 milliseconds, between 100 milliseconds and around 1000 milliseconds, between around 1 second and around 2 seconds, between around 2 seconds and around 5 seconds, or between around 5 seconds and around 10 seconds.

In some embodiments, each portion of the number of adjacent cardiac portions includes at least two S1 peaks of the number of S1 peaks and at least two S2 peaks of the number of S2 peaks. Plotting the number of adjacent cardiac portions may include plotting the pixel characteristic values of each portion vertically along a y-axis and plotting the time progression of the number of adjacent cardiac portions horizontally along an x-axis. The cardio-vibrational image matrix may represent, along the x-axis, visible differences in timing and/or pixel characteristic values of a portion of the number of S1 peaks and a portion of the number of S2 peaks. The operations may be configured to, prior to transforming, register a time scale of the cardio-vibrational measurements of the predetermined duration with a number of R-peaks of an ECG reading of the patient obtained during the predetermined duration, where segmenting includes segmenting at least in part according to the registering.

In some embodiments, the operations are configured to apply, to the cardio-vibrational image matrix, a smoothing algorithm to proximately located pixel characteristic values of the number of pixel characteristic values in the cardio-vibrational image matrix. The number of pixel characteristic values may include between around at least 3 and 16 different colors. The cardio-vibrational measurements may include a number of S3 peaks.

In some embodiments, the medical device includes a wearable cardiac monitoring device. The wearable cardiac medical device may include a cardiac holter monitor and associated number of ECG electrodes. The medical device may include a cardiac monitoring and treatment device. The cardiac monitoring and treatment device may include an automated external defibrillator. The cardiac monitoring and treatment device may include a wearable cardioverter defibrillator.

In some embodiments, the operations are configured to transmit the cardio-vibrational image matrix to a remote server. The operations may be configured to apply the cardio-vibrational image matrix to a machine learning classifier to determine an arrhythmia condition in the patient, where the machine learning classifier is trained to identify at least an existence and a nonexistence of an arrhythmia condition in ECG image matrices. The operations may be configured to apply the cardio-vibrational image matrix to at least one machine learning classifier to determine a present classification of a number of classifications of at least one cardiac risk biomarker, and generate, using the present classification, a prediction of future potential outcome related to the at least one cardiac risk biomarker.

In one aspect, the present disclosure relates to a method for monitoring a cardiac condition of a patient using ECG image matrix representations of ECG signals. The method may include obtaining, in real-time by processing circuitry, a number of ECG signals of a patient from at least two ECG electrodes of a wearable medical device, and monitoring, by the processing circuitry, for an abnormal rhythm in the patient by generating, from the number of ECG signals, ECG measurements of a predetermined duration, transforming the ECG measurements of the predetermined duration into an ECG image matrix, where transforming includes segmenting the ECG measurements of the predetermined duration into a number of adjacent ECG portions each having a duration smaller than the predetermined duration, and plotting the number of ECG portions using a number of pixel characteristic values mapped to parameter values of corresponding ECG measurements to produce the ECG image matrix. Monitoring for an abnormal rhythm may include applying the ECG image matrix to a machine learning classifier to determine an arrhythmia condition in the patient, where the machine learning classifier is trained to identify at least an existence and a nonexistence of an arrhythmia condition in ECG image matrices.

In some embodiments, the machine learning classifier is trained to identify at least the existence and the nonexistence of the arrhythmia condition by identifying noise conditions in the ECG image matrices. Identifying the arrhythmia condition may include classifying the arrhythmia condition based on applying the ECG image matrix to the machine learning classifier, where the machine learning classifier is trained to identify the type of arrhythmia condition using a number of arrhythmia classifications. The number of arrhythmia classifications may include at least one of a duration, a rate, or a mechanism of arrhythmia.

In some embodiments, generating the ECG measurements includes detecting, from the number of ECG signals, a number of ECG features including one or more of a set of R peaks, a set of P peaks, a set of T peaks, or a set of QRS complexes. A beginning of a time scale of the ECG image matrix may be registered to a deflection feature selected from the set of R peaks, the set of P peaks, the set of T peaks, and the set of QRS complexes, and the machine learning classifier may have been trained using a number of ECG image matrices registered to the deflection feature. Segmenting the ECG measurements may involve including at least one deflection feature in each portion of the number of adjacent ECG portions.

In some embodiments, the type of arrhythmia condition includes at least one of a supraventricular tachycardia (SVT), a ventricular tachycardia, ventricular fibrillation, tachycardia, bradycardia, asystole, a heart pause condition, pulseless electrical activity, or atrial fibrillation.

In some embodiments, a controller of the wearable medical device includes the processing circuitry. The processing circuitry may be disposed in a remote computer system. The period of time may be up to 30 seconds. The machine learning classifier may include a deep neural network (DNN) model.

In some embodiments, the method includes determining, by the processing circuitry from the number of ECG signals, a number of ECG metrics relating to one or more of heart rate, heart rate variability, PVC burden or counts, activity, noise quantifications, atrial fibrillation, momentary pauses, heart rate turbulence, QRS height, QRS width, changes in a size or a shape of the ECG morphology, cosine R-T, artificial pacing, corrected QT interval, QT variability, T wave width, T wave alternans, T-wave variability, ST segment changes, early repolarization, late potentials, fractionated QRS/HF content, or fractionated T wave/HF content. The method may include accessing, by the processing circuitry, one or more non-ECG physiological signals, and generating, by the processing circuitry, one or more patient metrics based on the one or more non-ECG physiological signals. The one or more non-ECG physiological signals may include cardio-vibrational signals, and the one or more patient metrics may relate to at least one of electromechanical activation time (EMAT), left ventricular systolic time (LVST), S1 intensity, S2 intensity, S3 intensity, S4 intensity, S1 duration, S2 duration, S3 duration, S4 duration, or heart murmurs. The one or more non-ECG physiological signals may include radiofrequency-based physiological signals, and the one or more patient metrics may relate to at least one of thoracic fluid content, arterial pulse measurements, blood pressure measurements, or heart wall movement. The machine learning classifier may be further trained to identify at least the existence and nonexistence of the arrhythmia condition based on the one or more patient metrics.

In some embodiments, the method includes causing, by the processing circuitry, the wearable medical device to provide an electrical therapeutic shock to the patient based on determining the arrhythmia condition in the patient. Causing the wearable medical device to provide the electrical therapeutic shock may include causing the wearable medical device to provide the electrical therapeutic shock within between at least around 5 seconds and around 2 minutes of an onset of the arrhythmia condition in the patient. The electrical therapeutic shock may include at least one of a defibrillating shock or a pacing pulse.

In one aspect, the present disclosure relates to a system for monitoring a cardiac condition of a patient using ECG image matrix representations of ECG signals. The system may include a non-volatile computer readable storage medium configured to store a number of ECG measurements, at least one machine learning classifier trained to identify at least an existence and a nonexistence of an arrhythmia condition in ECG image matrices, and operations stored as computer executable instructions to a non-transitory computer readable media and/or encoded in hardware logic. The operations may be configured to obtain, in real-time, a number of ECG signals of the patient from at least two ECG electrodes of a wearable medical device, and monitor for an abnormal rhythm in the patient by generating, from the number of ECG signals, ECG measurements of a predetermined duration, storing, to the non-volatile computer readable storage medium, the ECG measurements, and transforming the ECG measurements of the predetermined duration into an ECG image matrix. Transforming may include segmenting the ECG measurements of the predetermined duration into a number of adjacent ECG portions each having a duration smaller than the predetermined duration, and plotting the number of ECG portions using a number of pixel characteristic values mapped to parameter values of corresponding ECG measurements to produce the ECG image matrix. Monitoring for the abnormal rhythm may include applying the ECG image matrix to the machine learning classifier to determine an arrhythmia condition in the patient.

In some embodiments, the machine learning classifier is trained to identify at least the existence and the nonexistence of the arrhythmia condition by identifying noise conditions in the ECG image matrices. Identifying the arrhythmia condition may include classifying the arrhythmia condition based on applying the ECG image matrix to the machine learning classifier, where the machine learning classifier is trained to identify the type of arrhythmia condition using a number of arrhythmia classifications. The number of arrhythmia classifications may include at least one of a duration, a rate, or a mechanism of arrhythmia.

In some embodiments, generating the ECG measurements includes detecting, from the number of ECG signals, a number of ECG features including one or more of a set of R peaks, a set of P peaks, a set of T peaks, or a set of QRS complexes. A beginning of a time scale of the ECG image matrix may be registered to a deflection feature selected from the set of R peaks, the set of P peaks, the set of T peaks, and the set of QRS complexes, and the machine learning classifier may have been trained using a number of ECG image matrices registered to the deflection feature. Segmenting the ECG measurements may involve including at least one deflection feature in each portion of the number of adjacent ECG portions.

In some embodiments, the type of arrhythmia condition includes at least one of a supraventricular tachycardia (SVT), a ventricular tachycardia, ventricular fibrillation, tachycardia, bradycardia, asystole, a heart pause condition, pulseless electrical activity, or atrial fibrillation.

In some embodiments, the system includes the wearable medical device, where the wearable medical device includes the non-volatile computer readable storage medium. At least a portion of the non-transitory computer readable media and/or hardware logic may be disposed in a remote computer system. The period of time may be up to 30 seconds. The machine learning classifier may include a deep neural network (DNN) model.

In some embodiments, the operations are configured to determine, by from the number of ECG signals, a number of ECG metrics relating to one or more of heart rate, heart rate variability, PVC burden or counts, activity, noise quantifications, atrial fibrillation, momentary pauses, heart rate turbulence, QRS height, QRS width, changes in a size or a shape of the ECG morphology, cosine R-T, artificial pacing, corrected QT interval, QT variability, T wave width, T wave alternans, T-wave variability, ST segment changes, early repolarization, late potentials, fractionated QRS/HF content, or fractionated T wave/HF content. The operations may be configured to access one or more non-ECG physiological signals, and generate one or more patient metrics based on the one or more non-ECG physiological signals. The one or more non-ECG physiological signals may include cardiovibrational signals, and the one or more patient metrics may relate to at least one of electromechanical activation time (EMAT), left ventricular systolic time (LVST), S1 intensity, S2 intensity, S3 intensity, S4 intensity, S1 duration, S2 duration, S3 duration, S4 duration, or heart murmurs. The one or more non-ECG physiological signals may include radiofrequency-based physiological signals, and the one or more patient metrics may relate to at least one of thoracic fluid content, arterial pulse measurements, blood pressure measurements, or heart wall movement. The machine learning classifier may be further trained to identify at least the existence and nonexistence of the arrhythmia condition based on the one or more patient metrics.

In some embodiments, the operations are configured to cause the wearable medical device to provide an electrical therapeutic shock to the patient based on determining the arrhythmia condition in the patient. Causing the wearable medical device to provide the electrical therapeutic shock may include causing the wearable medical device to provide the electrical therapeutic shock within between at least around 5 seconds and around 2 minutes of an onset of the arrhythmia condition in the patient. The electrical therapeutic shock may include at least one of a defibrillating shock or a pacing pulse.

In one aspect, the present disclosure relates to a method for estimating risk of an adverse cardiac outcome in a patient. The method may include accessing, from a non-volatile computer readable storage medium, a number of ECG measurements obtained from ECG signals of a patient, and transforming, by the processing circuitry, a time series of the number of ECG measurements into at least one ECG image matrix. Transforming may include, for each set of one or more sets of ECG measurements, segmenting the ECG measurements into a number of adjacent ECG portions each having a predetermined duration, where segmenting results in a number of ECG portions, and plotting the number of ECG portions using a number of pixel characteristic values mapped to parameter values of corresponding ECG measurements to produce a respective matrix of the at least one ECG image matrix. The method may include applying, by the processing circuitry, the at least one ECG image matrix to at least one machine learning classifier to determine a present classification of the number of classifications of the at least one cardiac risk biomarker, where the at least one machine learning classifier was trained to identify a number of classifications of at least one cardiac risk biomarker, and generating, by the processing circuitry using the present classification, a prediction of future potential outcome in the patient related to the at least one cardiac risk biomarker.

In some embodiments, the at least one machine learning classifier was trained at least in part using a number of ECG image matrices generated from a number of historic ECG readings obtained from the patient. Generating the prediction may include comparing the present classification to at least one historic classification of the patient to determine patient progression related to the at least one cardiac risk biomarker.

In some embodiments, the at least one cardiac risk biomarker relates to one of sudden cardiac arrest (SCA), low ejection fraction (EF), or heart failure classification. The at least one cardiac risk biomarker may include low EF, and the number of classifications may include a less than 35% classification, a 35 to 39% classification, and a 40% to 54% classification. The at least one cardiac risk biomarker may relate to SCA, and the number of classifications includes one or more of ventricular fibrillation (VF), ventricular tachycardia (VT), pulseless electrical activity (PEA), or asystole.

In some embodiments, the method includes accessing, from the non-volatile computer readable storage medium, a number of cardio-vibrational measurements, the cardio-vibrational measurements including at least a number of S1 peaks and a number of S2 peaks, where the number of cardio-vibrational measurements were generated from a number of cardio-vibrational signals obtained by at least one vibrational sensor monitoring a heart of the patient. The method may include transforming, by the processing circuitry, a time series of the number of cardio-vibrational measurements into at least one cardio-vibrational image matrix, where transforming includes, for each set of set of one or more sets of cardio-vibrational measurements, segmenting the respective set of cardio-vibrational measurements into a number of adjacent cardiac portions each having a predetermined duration, where segmenting results in a number of cardiac portions, and plotting the number of cardiac portions using a number of pixel characteristic values mapped to parameter values of corresponding cardio-vibrational measurements to produce a respective matrix of the at least one cardio-vibrational image matrix. Determining the present classification may include applying a first cardio-vibrational image matrix of the at least one cardio-vibrational image matrix to the at least one machine learning classifier.

In some embodiments, the at least one cardiac risk biomarker is one of electromechanical activation over time (EMAT), left ventricular systolic time (LVST), S3 intensity, or S3 width.

In some embodiments, the method includes registering, by the processing circuitry, a time scale of the segmenting of the one or more sets of cardio-vibrational measurements to a time scale of the segmenting of the one or more sets of ECG measurements, where each set of the one or more sets of cardio-vibrational measurements corresponds to a respective set of the one or more sets of ECG measurements. The at least one machine learning classifier may have been trained at least in part using a number of cardio-vibrational image matrices generated based on a number of historic cardio-vibrational signals obtained from monitoring the heart of the patient.

In one aspect, the present disclosure relates to a system for estimating risk of an adverse cardiac outcome in a patient. The system may include a non-volatile computer readable storage medium including a number of ECG measurements obtained from ECG signals of a patient, at least one machine learning classifier trained to identify a number of classifications of at least one cardiac risk biomarker, and operations stored as computer executable instructions to a non-transitory computer readable media and/or encoded in hardware logic. The operations may be configured to transform a time series of the number of ECG measurements into at least one ECG image matrix, where transforming includes, for each set of one or more sets of ECG measurements, segmenting the ECG measurements into a number of adjacent ECG portions each having a predetermined duration, where segmenting results in a number of ECG portions, and plotting the number of ECG portions using a number of pixel characteristic values mapped to parameter values of corresponding ECG measurements to produce a respective matrix of the at least one ECG image matrix. The operations may be configured to apply the at least one ECG image matrix to the at least one machine learning classifier to determine a present classification of the number of classifications of the at least one cardiac risk biomarker, and generate, using the present classification, a prediction of future potential outcome in the patient related to the at least one cardiac risk biomarker.

In some embodiments, the at least one machine learning classifier was trained at least in part using a number of ECG image matrices generated from a number of historic ECG readings obtained from the patient. Generating the prediction may include comparing the present classification to at least one historic classification of the patient to determine patient progression related to the at least one cardiac risk biomarker.

In some embodiments, the at least one cardiac risk biomarker relates to one of sudden cardiac arrest (SCA), low ejection fraction (EF), or heart failure classification. The at least one cardiac risk biomarker may include low EF, and the number of classifications may include a less than 35% classification, a 35 to 39% classification, and a 40% to 54% classification. The at least one cardiac risk biomarker may relate to SCA, and the number of classifications may include one or more of ventricular fibrillation (VF), ventricular tachycardia (VT), pulseless electrical activity (PEA), or asystole.

In some embodiments, the non-volatile computer readable storage medium includes a number of cardio-vibrational measurements, the cardio-vibrational measurements including at least a number of S1 peaks and a number of S2 peaks, where the number of cardio-vibrational measurements were generated from a number of cardio-vibrational signals obtained by at least one vibrational sensor monitoring a heart of the patient. The operations may be configured to transform a time series of the number of cardio-vibrational measurements into at least one cardio-vibrational image matrix, where transforming includes, for each set of set of one or more sets of cardio-vibrational measurements, segmenting the respective set of cardio-vibrational measurements into a number of adjacent cardiac portions each having a predetermined duration, where segmenting results in a number of cardiac portions, and plotting the number of cardiac portions using a number of pixel characteristic values mapped to parameter values of corresponding cardiovibrational measurements to produce a respective matrix of the at least one cardio-vibrational image matrix. Determining the present classification may include applying a first cardio-vibrational image matrix of the at least one cardio-vibrational image matrix to the at least one machine learning classifier. The at least one cardiac risk biomarker may be one of electromechanical activation over time (EMAT), left ventricular systolic time (LVST), S3 intensity, or S3 width. Each set of the one or more sets of cardio-vibrational measurements may correspond to a respective set of the one or more sets of ECG measurements. The operations may be configured to register a time scale of the segmenting of the one or more sets of cardio-vibrational measurements to a time scale of the segmenting of the one or more sets of ECG measurements. The at least one machine learning classifier may have been trained at least in part using a number of cardio-vibrational image matrices generated based on a number of historic cardio-vibrational signals obtained from monitoring the heart of the patient.

The foregoing general description of the illustrative implementations and the following detailed description thereof are merely exemplary aspects of the teachings of this disclosure and are not restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
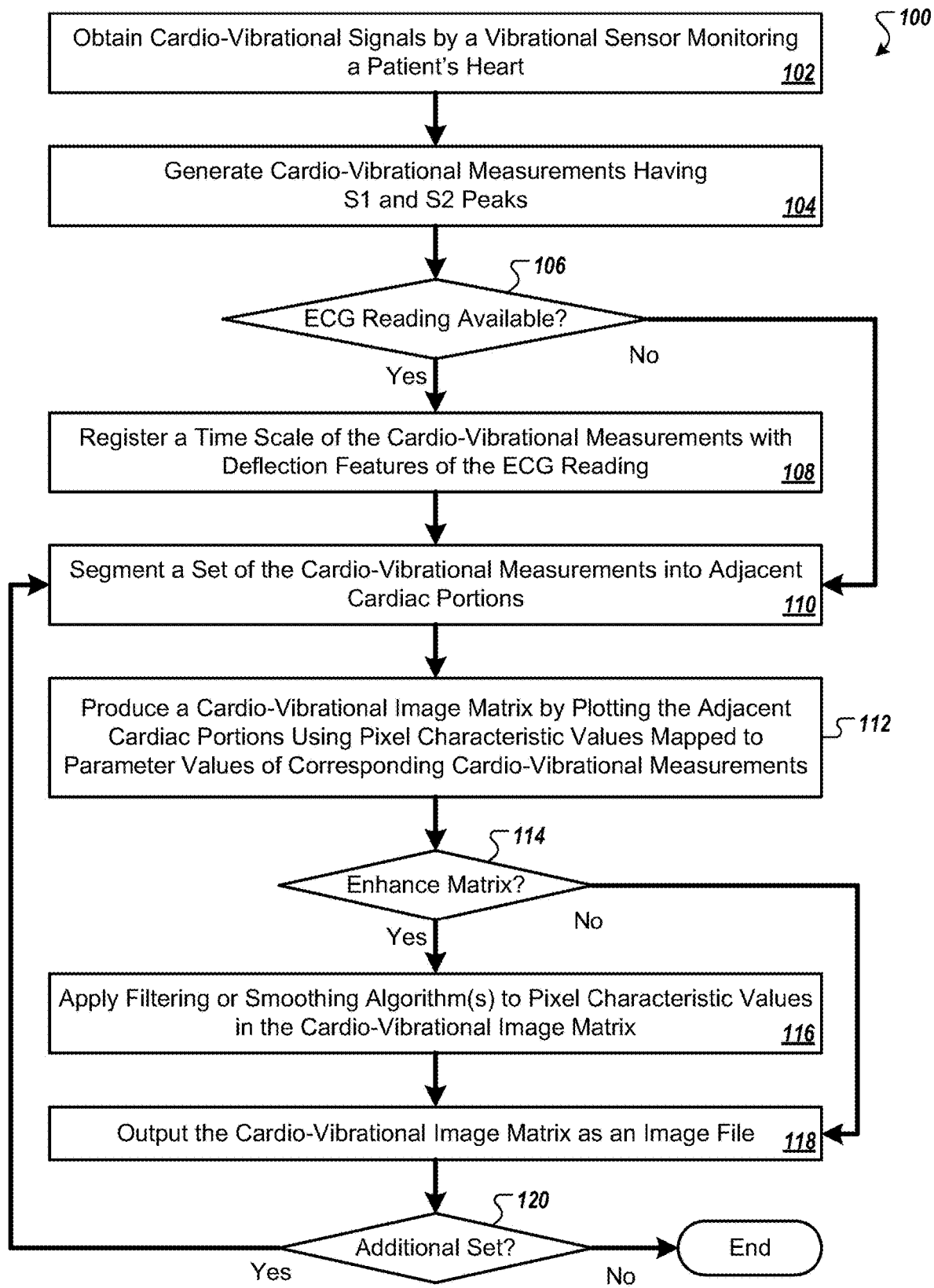
FIG. 1 is a flow chart of an example method for generating a cardio-vibrational image matrix from cardio-vibrational signals obtained through monitoring a patient.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

In one aspect, the present disclosure relates to methods and systems for monitoring progression of cardiac disease in a patient by transforming cardio-vibrational signals (e.g., signals corresponding to heart vibrations detected in a patient) obtained through monitoring a patient into a cardio-vibrational image matrix. The cardio-vibrational signals may be obtained from a sensor of a medical device, such as a wearable heart monitoring device. The cardio-vibrational image matrix visually represents differences in timing and/or occurrences of S1 peaks, S2 peaks, and/or other cardio-vibrational parameters and characteristics, such as S3 peaks, S4 peaks, heart murmurs, among others. The cardio-vibrational image matrix format is advantageous in providing a comparison mechanism that easily highlights to an end user substantial changes in timing and/or intensity of S1 peaks, S2 peaks, and/or other cardio-vibrational parameters and characteristics, such as S3 peaks, S4 peaks, heart murmurs, among others. For example, such information contained in cardio-vibrational signals of a predetermined duration can be depicted in an image. For instance, such predetermined duration can be of 30 seconds, 60 seconds, 90 seconds, 180 seconds, 300 seconds, or values therebetween. Viewing cardio-vibrational signals of such durations can result in a relatively lengthy signal strip of data for viewing compared to a visible size of a cardio-vibrational image matrix. Further, the cardio-vibrational image matrix format is advantageous in providing a pixel mapping that visibly contrasts S1, S2, S3 and S4 parameter values from other parameter values within the cardio-vibrational signal (e.g., via pixel intensity and/or hue as described further below). In this manner, harder to detect or view parameter values such as S3 and S4 be visibly contrasted from S1 and S2 parameter values. In comparison to a clinician reviewing the original measurements obtained from the signal in a cardio-vibrational signal graph, a clinician reviewing the cardio-vibrational image matrix has the opportunity to key in on significant events captured in the cardio-vibrational signals without detailed and lengthy scrutiny. Further, some significant events which may have been lost or misinterpreted in the cardio-vibrational graph are rendered readily apparent in the transformation into the cardio-vibrational image matrix format. Thus, the cardio-vibrational image matrix advantageously provides clinicians with the ability to carry out detailed analysis and draw more insights of the contents of the cardio-vibrational signals than from reviewing cardio-vibrational signal strips of data.

In some embodiments, to transform the cardio-vibrational measurements into a cardio-vibrational image matrix, cardio-vibrational measurements of a predetermined duration are generated from the cardio-vibrational signals. The cardio-vibrational measurements may be segmented into adjacent cardiac portions. The parameter values of the cardio-vibrational measurements of each cardiac portion may be mapped to pixel characteristic values (e.g., hue, intensity) and plotted as a cardio-vibrational image matrix having, on one axis, a time progression of the adjacent cardiac portions and, on another axis, the pixel characteristic values of each portion. While references herein to pixel characteristics values pertain to hue and/or intensity values, it is appreciated that other pixel characteristics may be substituted for or combined with hue and/or intensity values in transmitting underlying information. For example, pixel characteristics can include pixel saturation and brightness, as additional or alternative pixel characteristics for rendering the cardio-vibrational image matrix.

In some embodiments, the cardio-vibrational image matrix is output as an image file for use by a clinician in monitoring a patient. The image presented to the clinician, for example at a display of a computing device, may be a static image such as a static cardio-vibrational image matrix graph. In another example, the clinician is presented with a dynamic cardio-vibrational image, such as a moving image (or video) providing real-time or near-real-time feedback on the cardio-vibrational signals obtained through monitoring the patient. For example, the moving image can move along a horizontal timeline in accordance with a predetermined or a user-configurable speed. For example, the moving image can move at a rate of acquired real time data, but provide a user an ability to accelerate or slow down the moving image.

In an example, a dynamic ECG image (or video) can periodically refresh in accordance with a predetermined or a user-configurable refresh rate. For example, such a dynamic image can be refreshed at a periodic rate set by the user through a user-configurable parameter. For instance, the refresh rate may be set to be 5 seconds, and a user can modify the refresh rate to 30 seconds, 1 minute, 5 minutes, or more. In this example, the image can be refreshed as additional cardio-vibrational signal information is available. For instance, if the cardio-vibrational information is acquired in real time, the image can be refreshed every predefined period. For example, such predefined period can be 30 seconds, 45 seconds, 90 seconds, 120 seconds, 180 seconds, 300 seconds, or other values therebetween.

In examples, an ECG image matrix can be derived from ECG signals. The ECG signals may be obtained from one or more ECG electrodes of a medical device, such as a wearable heart monitoring device. The ECG image matrix visually represents differences in timing and/or intensity of ECG fiducial points, such as P, Q, R, S, T, U, V values, and/or other ECG parameters and characteristics, such as QP, QR, ST, TU segment changes, among others. The ECG image matrix format is advantageous in providing a comparison mechanism that easily highlights to an end user substantial changes in timing and/or intensity of ECG fiducial points, such as P, Q, R, S, T, U, V values, and/or other ECG parameters and characteristics, such as QP, QR, ST, TU segment changes, among others. For example, such information contained in ECG signals of a predetermined duration can be depicted in the ECG image matrix. For instance, such predetermined duration can be of 30 seconds, 60 seconds, 90 seconds, 180 seconds, 300 seconds, or values therebetween, In some examples, to transform the ECG measurements into an ECG image matrix, ECG measurements of a predetermined duration are generated from the ECG signals. The ECG measurements may be segmented into adjacent cardiac portions. The parameter values of the ECG measurements of each cardiac portion may be mapped to pixel characteristic values (e.g., hue, intensity) and plotted as an ECG image matrix having, on one axis, a time progression of the adjacent cardiac portions and, on the other axis, the pixel characteristic values of each portion. While references herein to pixel characteristics values pertain to hue and/or intensity values, it is appreciated that other pixel characteristics may be substituted for or combined with hue and/or intensity values in transmitting underlying information. For example, pixel characteristics can include pixel saturation and brightness, as additional or alternative pixel characteristics for rendering the ECG image matrix.

In some embodiments, the ECG image matrix is output as an image file for use by a clinician in monitoring a patient. The image presented to the clinician, for example at a display of a computing device, may be a static image such as a static ECG image matrix graph. In another example, the clinician is presented with a dynamic ECG image, such as a moving image (or video) providing real-time or near-real-time feedback on the ECG signals obtained through monitoring the patient. For example, the moving image can move along a horizontal timeline in accordance with a predetermined or a user-configurable speed. For example, the moving image can move at a rate of acquired real time data, but provide a user an ability to accelerate or slow down the moving image.

In an example, a dynamic ECG image (or video) can periodically refresh in accordance with a predetermined or a user-configurable refresh rate. For example, such a dynamic image can be refreshed at a periodic rate set by the user through a user-configurable parameter. For instance, the refresh rate may be set to be 5 seconds, and a user can modify the refresh rate to 30 seconds, 1 minute, 5 minutes, or more. In this example, the image can be refreshed as additional ECG signal information is available. For instance, if the ECG information is acquired in real time, the image can be refreshed every predefined period. For example, such predefined period can be 30 seconds, 45 seconds, 90 seconds, 120 seconds, 180 seconds, 300 seconds, or other values therebetween.

In some embodiments, the cardio-vibrational image matrix and/or an ECG image matrix is developed in real-time to automatically monitor a patient for signs of an arrhythmia condition. For example, rather than or in addition to being presented to a clinician, cardio-vibrational image matrices and/or ECG image matrices may be provided to an image analysis algorithm for automatically identifying an arrhythmia condition occurring in the patient. The image analysis algorithm may be a machine learning algorithm applying one or more machine learning classifiers each trained to detect a different type of arrhythmia. In one implementation, the image analysis algorithm may be configured to identify a state of arrhythmia versus a state of no arrhythmia. Further, in some implementations, the image analysis algorithm may be configured to identify a type of arrhythmia. Advantageously, the cardio-vibrational image matrix analysis may be performed to confirm the presence of an arrhythmia as compared to noise within the signal, thus avoiding unnecessary delivery of electrical therapeutic therapy in the absence of arrhythmia.

The cardio-vibrational image matrix, in some embodiments, is developed to automatically screen, using one or more machine learning classifiers, a patient's cardiac signals for one or more cardiac risk biomarkers. In some embodiments, the cardio-vibrational image matrix is developed as a number of cardio-vibrational image matrices produced over time are analyzed to identify trends in a patient's cardiac risk or heart failure condition. Alternatively, the ECG image matrix, in some embodiments, is developed to be used in conjunction with the cardio-vibrational image matrix to automatically screen, using one or more machine learning classifiers, a patient's cardiac (ECG and cardio-vibration) signals for one or more cardiac risk biomarkers.

In one aspect, the present disclosure relates to automatically screening a cardio-vibrational image matrix and/or an ECG image matrix, using machine learning classifiers, to identify one or more cardiac risk biomarkers. The automated screening, for example, may be used to monitor patient health, determine a best course of treatment, and/or manage appropriate follow up care for a patient based upon a prediction of risk of future cardiac disease or disorder. The screening may take into consideration at least a portion of a patient's ECG signals and/or cardio-vibrational signals captured over an extended period of time, such as at least ten minutes, at least one hour, about three hours, around one day, or up to a week. The cardiac risk biomarkers, for example, may be representative of risk of one or more of sudden cardiac arrest (SCA), low ejection fraction (EF), or a stage of heart failure. The cardiac risk biomarkers, in some examples, may include EMAT, LVST, S3 intensity, and/or S3 width. One or more machine learning analysis processes, for example, may apply the machine learning classifiers to the ECG image matrix and/or cardio-vibrational image matrix to determine a heart risk classification. The heart risk classification may be analyzed, in light of additional metrics and/or patient factors, to determine a set of heart risk metrics. The heart risk metrics may be presented in a report, for example for review by a clinician or patient.

In one aspect, the present disclosure relates to analyzing a number of cardio-vibrational image matrices and/or ECG image matrices produced over time to identify trends in a progression of a patient's cardiac health or heart failure condition. The heart failure progression screening, for example, may be used to monitor patient health, determine whether a course of treatment appears to be successful in mitigating worsening of heart failure, and/or manage appropriate follow up care for a patient based upon a present assessment of heart failure trends in the patient. For example, the image matrices may be analyzed using machine learning classifiers to determine a present stage of heart failure out of a number of stages of heart failure, such as the New York Heart Association (NYHA) heart failure classifications ranging from Class I to Class IV heart failure. For example, the output from such analysis may classify patients in accordance with the following Table 1.

TABLE 1

| NYHA Class | Patients with Cardiac Disease (Description of HF Related Symptoms) |
|---|---|
| Class I (Mild) | Patients with cardiac disease but without resulting in limitation of physical activity. Ordinary physical activity does not cause undue fatigue, palpitation (rapid or pounding heart beat), dyspnea (shortness of breath), or anginal pain (chest pain). |
| Class II (Mild) | Patients with cardiac disease resulting in slight limitation of physical activity. They are comfortable at rest. Ordinary physical activity results in fatigue, palpitation, dyspnea, or anginal pain |
| Class III (Moderate) | Patients with cardiac disease resulting in marked limitation of physical activity. They are comfortable at rest. Less than ordinary activity causes fatigue, palpitation, dyspnea, or anginal pain. |
| Class IV (Severe) | Patients with cardiac disease resulting in the inability to carry on any physical activity without discomfort. Symptoms of heart failure or the anginal syndrome may be present even at rest. If any physical activity is undertaken, discomfort is increased. |

In examples, the output of the machine learning classification can result in a classification in accordance with the American Heart Association (AHA) heart failure stages. For example, the classification can be based as shown below.

Stage A: Presence of heart failure risk factors but no heart disease and no symptoms Stage B: Heart disease is present but there are no symptoms (structural changes in heart before symptoms occur)

Stage C: Structural heart disease is present AND symptoms have occurred

Stage D: Presence of advanced heart disease with continued heart failure symptoms requiring aggressive medical therapy In accordance with the above classification, the machine learning models can be trained using thousands or more of training image matrices (along with other cardiac and health history information of patients) to produce the relevant heart failure classification for the patient. A progression of heart failure from Class 1 to Class 2, and then on to Class 3 or Class 4, or a progression of heart failure from Stage A to Stage B, and then on to Stage C or Stage D indicates worsening heart failure. For example, improvements in NYHA or AHA class symptoms indicate improving heart failure condition in the patient. In examples, instead of or in addition to NYHA or AHA class symptoms, the device can monitor predetermined physiologic parameters to determine improving or worsening heart failure condition in the patient. For example, the device can monitor for trends in certain cardiac risk biomarkers including increase of decrease in EMAT, increase or decrease in S3 intensity, increase or decrease in ejection fraction (EF) values, increase or decrease in pulmonary capillary wedge pressure, or increase or decrease in cardiac output. Such changes in these cardiac risk biomarkers are used by machine learning classifiers in outputting the appropriate status of the patient and further, in some examples, recommending the appropriate heart failure treatment for the patient. In implementations, the machine learning models used in the classification may be trained in part using historic image matrices generated from signals produced from monitoring the patient, thereby advantageously taking into consideration the unique cardiac signature of the patient. The classification provided by the machine learning analysis process(es) may be further analyzed, in view of additional historic sets of ECG and/or cardio-vibrational metrics, to determine heart failure progression metrics. The heart failure progression metrics may be presented in a report, for example for review by a clinician or patient.

FIG. 1 is a flow chart of an example method 100 for generating a cardio-vibrational image matrix from cardio-vibrational signals obtained through monitoring a patient. The method 100, for example, may be used in monitoring a cardiac condition of a patient using a wearable medical device. In some examples, the method 100 may be performed by processing circuitry of a medical device such as a wearable medical device, by one or more processors of a server or server system, or by one or more processors of a cloud computing platform. Portions of the method 100, in some embodiments, are performed on different computing platforms. For example, the generation of cardio-vibrational measurements (104) may be performed locally at a medical device, while producing the cardio-vibrational image matrix (112) may occur at a remote computing device or system.

In some implementations, the method begins with obtaining, by a vibrational sensor monitoring a patient's heart, cardio-vibrational signals (102). The vibrational sensor, in some examples, may be a medical grade accelerometer or microphone configured to monitor pulmonary vibrations. The vibrational sensor, in one example, attached to or built into a wearable cardiac monitoring device. The sensor may be positioned to contact skin on the patient. In another example, the sensor is releasably attached to the patient, for example using a medical grade adhesive. The signals may be obtained by one or more processors of a medical device, such as a wearable cardiac monitoring device. The signals, in another example, may be relayed via a network to a remote computing system such as a medical facility server or a cloud computing platform.

In some implementations, cardio-vibrational measurements are generated from the cardio-vibrational signals (104). The cardio-vibrational measurements, for example, may include parameter values corresponding to at least a number of peaks and troughs in the cardio-vibrational signal. The cardio-vibrational measurements, in some examples, may represent waveform morphology captured in the cardio-vibrational signal such as, in some examples, magnitudes, amplitudes, and/or phases captured in the cardio-vibrational measurements.

In some implementations, if an ECG reading corresponding to a same timeframe as the capture of the cardio-vibrational signals is available (106), a time scale of the cardio-vibrational measurements is registered with one or more types of deflection features of the ECG reading (108). In some examples, the time scale of the cardio-vibrational measurements may be registered with R peaks, P peaks, T peaks, and/or QRS complexes of the ECG reading. Registering the cardio-vibrational signal with the ECG reading, for example, may allow analysis of measurements obtained using both mechanisms, thereby supporting a more in-depth evaluation of cardiac condition. Further, registering the ECG reading with the cardio-vibrational measurements may be advantageous in enabling greater precision in the calculation of certain metrics, such as electromechanical activation time (EMAT) or left ventricular systolic time (LVST).

In some implementations, a set of the cardio-vibrational measurements is identified for conversion into a cardio-vibrational image matrix (110). The set of the cardio-vibrational measurements may represent a selected period of time (e.g., predetermined duration) such as, in some examples, 15 seconds, 30 seconds, 45 seconds, or 60 seconds to be real-real-time responsive to cardiac conditions occurring in the heart of the patient such as arrhythmia, thereby supporting timely and responsive therapeutic support, such as defibrillation or pacing pulse delivery. In further examples, the selected period of time may be around 30 seconds, around 60 seconds, around 90 seconds, around 120 seconds, around 180 seconds, around 300 seconds, or around 5 minutes to allow for analysis of less frequent cardiac behaviors and/or longer signatures of activity. In additional examples, the selected period of time may be at least 10 minutes for detailed analysis of heart failure and cardiac risk conditions, such as ejection fraction (EF) analysis or supraventricular tachycardia (SVT) classification. The predetermined duration, in further examples, may be between around 15 seconds and around 30 seconds, between around 30 seconds and around 45 seconds, between around 45 seconds and around 60 seconds, between around 60 seconds and around 90 seconds, between around 90 seconds and 120 seconds, between around 2 minutes or around 3 minutes, or between around 3 minutes and around 10 minutes.

In some embodiments, the set of cardio-vibrational measurements is selected so that the signals begin and/or end based upon the time registration with the ECG reading if registering was conducted. For example, the set of the cardio-vibrational measurements may be configured to begin at a certain type of ECG peak or at a set time offset from the type of ECG peak. The set may be further selected to represent at least a threshold number of a certain type of peak, such as, in an illustrative example, 60 R-peaks.

The identified set of cardio-vibrational measurements, in some implementations, is segmented into the adjacent cardiac portions (110). Each cardiac portion, in some embodiments, represents a duration smaller than the predetermined duration such as, in some examples, around 100 milliseconds, around 1000 milliseconds, around 1 second, around 2 seconds, around 5 seconds, around 10 seconds, around 15 seconds, or around 20 seconds. The duration, in some embodiments involving time registration with the ECG reading, is selected to capture, in each cardiac portion, a threshold number of a type of ECG peak. For example, such threshold number can be at least 2, 3, 4 or 5 of a type of ECG fiducial point. For example, the threshold number may be at least 2 R peaks of the ECG signal. In illustration, turning to FIG. 2A, the cardiac portions may be divided so that the R peak registration aligns with around 0.2 seconds on a y-axis 202b (e.g., over a span of 1.2 second), such that cardio-vibrational measurements corresponding to a valve opening is anticipated shortly thereafter.

The alignment with the R peak registration (or, conversely, another deflection feature), for example, may compensate for variations in duration and amplitude of individual cardio vibrations during each cardiac cycle. The cardiac portions, in further examples, may generally each have a duration spanning between around 1 millisecond and around 100 milliseconds, between 100 milliseconds and around 1000 milliseconds, between around 1 second and around 2 seconds, between around 2 seconds or around 5 seconds, or between around 5 seconds and around 10 seconds. The period of time represented by each cardiac portion, in some implementations, may be selected in part based upon a type of analysis desired. For example, real-time arrhythmia monitoring may involve a shorter timeframe, while sudden cardiac arrest (SCA) risk prediction analysis may involve review of lengthier timeframes. The duration, for example, may correspond in part to a total duration of the set (e.g., a longer set of cardio-vibrational measurements may correspond to a longer timeframe for each cardiac portion of the set of cardio-vibrational measurements).

Figure 2A:
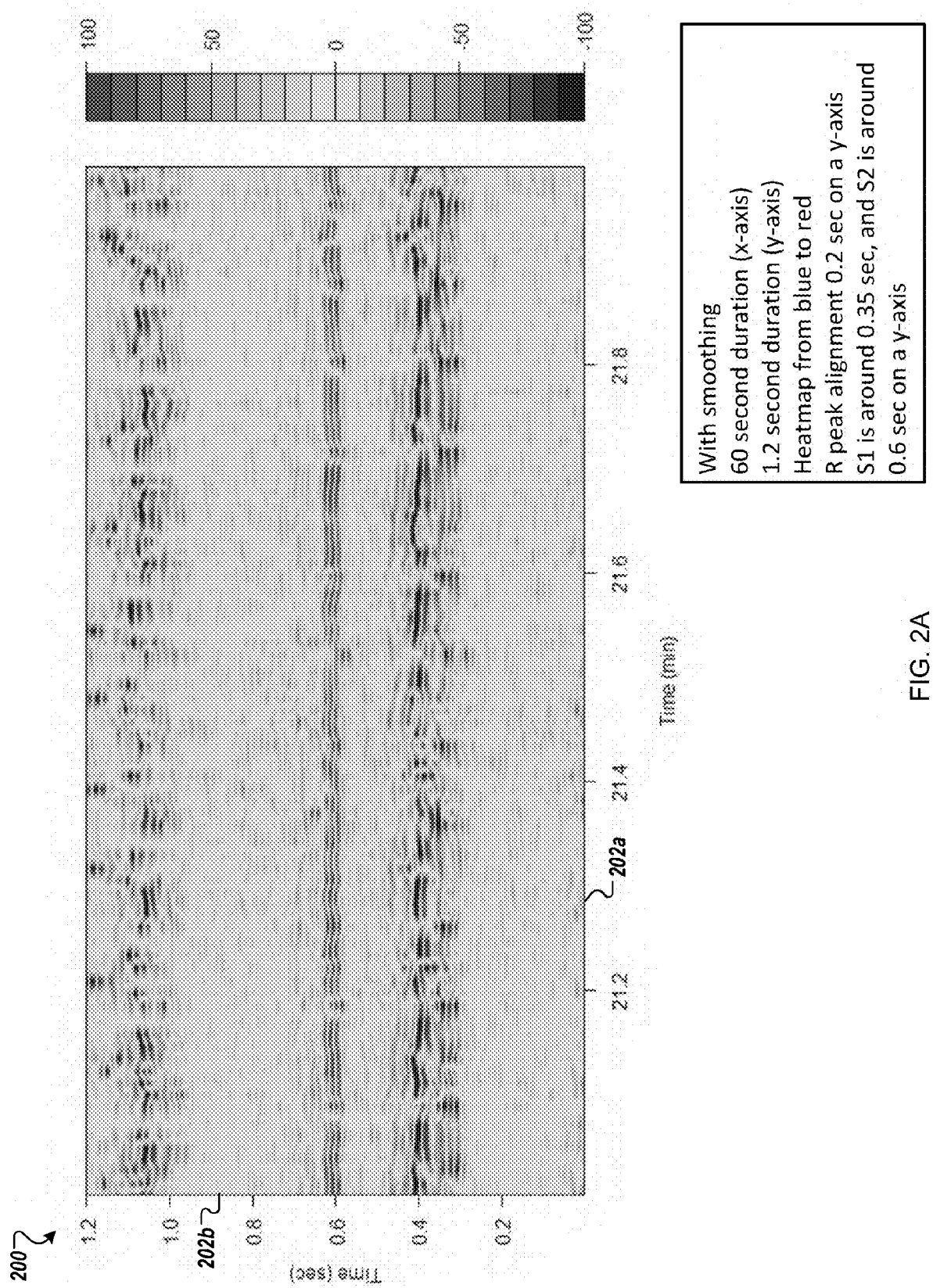
FIGS. 2A and 2B illustrate example cardio-vibrational image matrices.
Figure 2B:
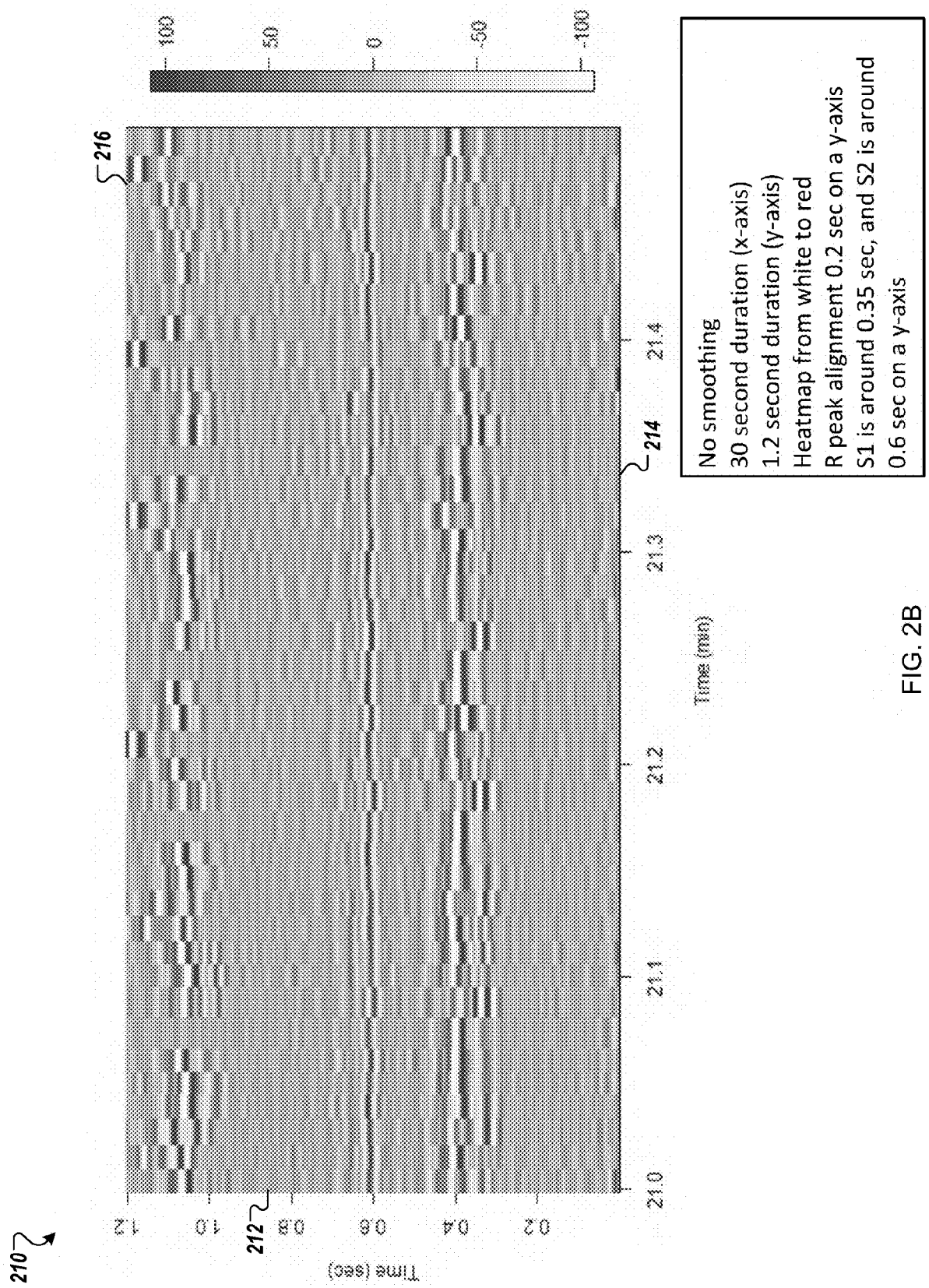

In some implementations, a cardio-vibrational image matrix is produced by plotting the adjacent cardiac portions using pixel characteristic values mapped to parameter values of the corresponding cardio-vibrational measurements (112). The pixel characteristic values, for example, may include pixel hue and/or pixel intensity. In an example, the color spectrum of the pixel characteristic values may include at least three colors, four colors, eight colors, or up to 16 colors. For example, as illustrated in FIG. 2A, an example cardio-vibrational image matrix 200 includes hues of yellow, orange, red, and green pixels. The pixel characteristic values, for example, may be arranged in a heat map to draw a clinician's attention to particularly relevant or important data, such as occurrences and intensities of S1, S2, S3, and S4 peaks. As illustrated in FIG. 2B, a pixel heat map scale 216 of an example cardio-vibrational image matrix 210 illustrates a range of magnitude intensities ranging from white to red. In another example, the pixel characteristic values may be mapped to distinct hues and/or intensities beneficial for automated analysis. The map of pixel characteristic values, in some embodiments, is selected from a set of maps of pixel characteristic values designed for different categories of parameter values, different types of interpretation, and/or highlighting different types of information. For example, a first map of pixel characteristic values may be applied in mapping amplitude parameter values, a second map may be applied in mapping phase parameter values, and a third map may be applied in mapping magnitude parameter values. Plotting, for example, may involve creating a graphic representation of the mapped parameter values as a time progression of adjacent cardiac portions plotted along a first axis of the cardio-vibrational image matrix, where parameter values of individual cardiac portions are plotted along a second axis of the cardio-vibrational image matrix. Turning to FIG. 2A, for example, the example cardio-vibrational image matrix 200 includes cardiac portions spanning 1.2 second each along a y-axis 202b over a one-minute duration of cardio-vibrational measurements along an x-axis 202a. In FIG. 2B, the example cardio-vibrational image matrix 210 includes cardiac portions spanning 1.2 seconds each along a y-axis 212 over a 30 second duration (21.0 minutes to 21.5 minutes) of cardio-vibrational measurements plotted along an x-axis 214.

In some implementations, if enhancement of the cardio-vibrational image matrix is desired (114), a filtering or smoothing algorithm is applied to at least certain pixel characteristic values in the cardio-vibrational image matrix (116). In some embodiments, a smoothing algorithm is applied to proximately located pixel characteristic values in the cardio-vibrational image matrix. The smoothing algorithm may reduce noise across the data by adjusting proximate pixel groups to display an averaging of the data represented by the pixel group (e.g., a rectangular section including at least 4 pixels). The smoothing algorithm, for example, may improve human readability of the data, leading to more accurate interpretation of the image data. The smoothing data may advantageously remove extraneous noise from the image, allowing a human to swiftly recognize important trends and anomalies within the cardio-vibrational image matrix. As illustrated in FIG. 2A, for example, the cardio-vibrational image matrix has been enhanced using a smoothing algorithm. FIG. 2B, on the other hand, has not been enhanced with smoothing to illustrate, in comparison, the effect of a smoothing algorithm.

In implementations, one or more template cardio-vibrational and/or ECG image matrices can be recorded and stored for analysis and/or comparison. For instance, an initial baseline cardio-vibrational and/or ECG image matrix can be recorded to be used as a template. For example, the initial baseline can be recorded at a predetermined time (e.g., prior to use of the device, such as during an initial fitting). Thereafter, new cardio-vibrational and/or ECG image matrices may be compared to the patient's baseline template. In examples, the baseline template can be periodically updated. For example, the patient can be prompted on a recurring period to manually record a baseline template cardio-vibrational and/or ECG image matrix. For example, the device can automatically initiate on a recurring period recording a baseline template cardio-vibrational and/or ECG image matrix. For example, the device can initiate a new baseline recording when a threshold number of false positives (e.g., 3-4 false positives in a 48-hour period, or 8-10 false positives in a one-week period) is recorded. In implementations, the device can cause a baseline template to record the patient's dominant rhythm and/or any abnormal rhythms that the patient may have had in the past. The device can use the prior knowledge of stored abnormal rhythms to avoid false alerts or otherwise reducing a number of alerts to the patient. In the example of the abnormal rhythms, when such a rhythm occurs, but the patient is otherwise physiologically normal (e.g., the patient presses response buttons on a wearable defibrillator or otherwise reports they are feeling fine via a user interface), the device can record the abnormal rhythm to store as a template for future comparison.

In examples, the device can have access to a universal rhythm template library based on templates recorded across several tens, hundreds, or thousands of similarly situated patients (e.g., similar patient demographics as the subject patient). For example, the demographics can include patients having similar age, ethnicity, weight, height, prior cardiac history, prior treatment history, among others. In this manner, an individual patient's rhythm as indicated in a cardio-vibrational or ECG image matrix can be rapidly compared via techniques described herein to assess a quick and accurate diagnosis. For example, such a template library can be stored on the wearable device or a gateway device with which the wearable device is in communication (e.g., wireless communication) via Bluetooth®, Zigbee®, or WiFi® technology. In some implementations, the cardio-vibrational image matrix is output as an image file (118). The cardio-vibrational image matrix, for example, may be provided to a display of a computing device for review by a clinician or incorporated in a report for review by an end user. For example, the image may be displayed via a user interface mounted on an external housing of the wearable medical device. In implementations, the image may be transmitted via a network interface in the wearable medical device (described in further detail below) to a remote server, for display at a remote computer screen viewed by a technician, a caregiver (e.g., a nurse, a physician, a physician's assistant, or other authorized medical representative) or other authorized person, in communication with the remote server. The cardio-vibrational image matrix, in another example, may be provided to one or more analysis algorithms for automated analysis of the data captured in the cardio-vibrational image matrix. If the cardio-vibrational image matrix was time registered to an ECG reading, in some embodiments, the cardio-vibrational image matrix is output to a graphic preparation algorithm for combining the cardio-vibrational image matrix with ECG data in a manner that enhances review of the information by an end user. In some embodiments, outputting the cardio-vibrational image matrix involves transmitting the cardio-vibrational image matrix to a remote computing system via a network. As noted, the end user may be the patient or a designated representative of the patient (e.g., a health care proxy), a caregiver (e.g., a nurse, a physician, a physician's assistant, or other authorized medical representative), or other authorized person (e.g., a service technician).

In some implementations, if additional sets of cardio-vibrational measurements are available for transformation (120), the method 100 continues with segmenting a next set of cardio-vibrational measurements into adjacent cardiac portions (110). The time-series of cardio-vibrational image matrices generated by iterating through at least the portion of the method 100, for example, may support real-time data interpretation and/or a dynamic (e.g., video) output to a clinician device.

Although described as a series of steps, in other embodiments, the method 100 may include more or fewer steps. For example, the method 100 may include obtaining ECG signals and generating ECG measurements for registering the time scale (108). In another example, rather than outputting the cardio-vibrational image matrix as an image file, the cardio-vibrational image matrix may be added to an existing file or the plotted data streamed to a remote processor for additional operations. In some implementations, a portion of the steps of the method 100 may be performed in parallel. For example, while the cardio-vibrational measurements are being transformed into the cardio-vibrational image matrix through segmenting (110) and plotting (112), a next set of cardio-vibrational signals may be obtained (102) and used to generate a next set of cardio-vibrational measurements (104). Other modifications to the method 100 are possible while remaining in the scope and spirit of the disclosure.

Figure 3A:
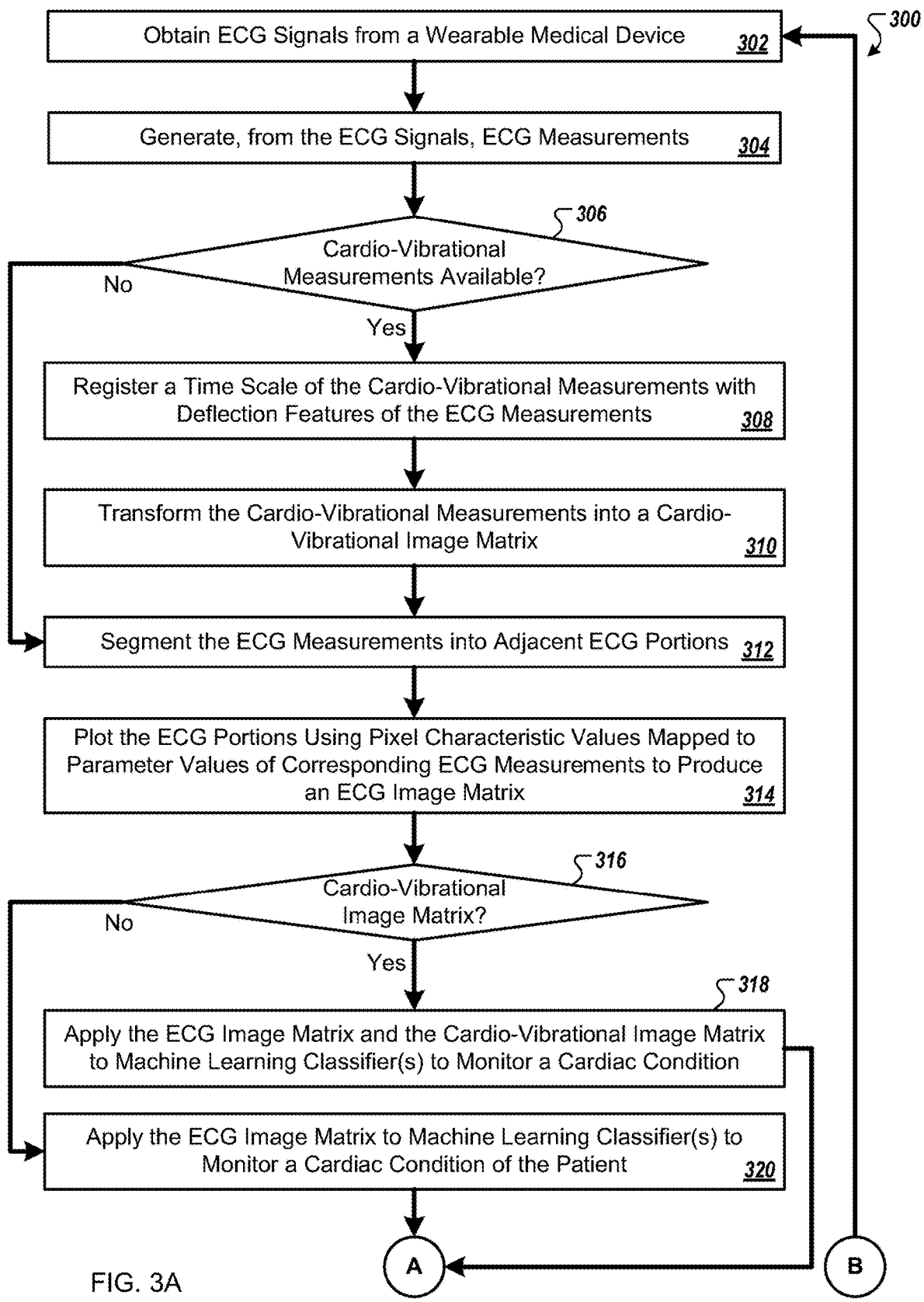
FIGS. 3A and 3B illustrate a flow chart of an example method for generating and applying an ECG image matrix for monitoring a cardiac condition of a patient.
Figure 3B:
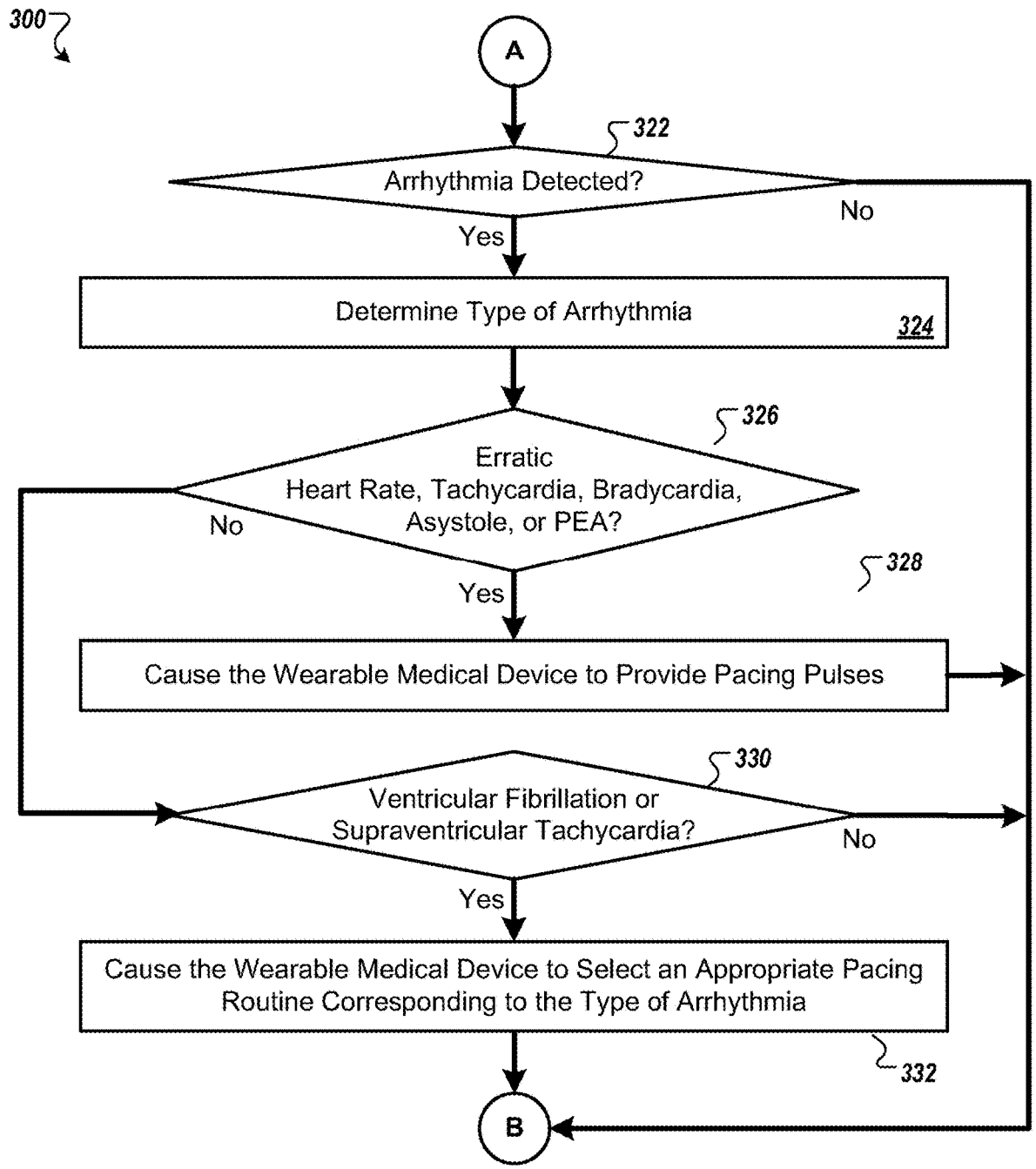

FIGS. 3A and 3B illustrate a flow chart of an example method 300 for generating and applying an ECG image matrix for monitoring a cardiac condition of a patient. The method 300, for example, may be used in monitoring a cardiac condition of a patient using a wearable medical device. In some examples, the method 300 may be performed by processing circuitry of a medical device such as a wearable medical device, by one or more processors of a server or server system, or by one or more processors of a cloud computing platform. Portions of the method 300, in some embodiments, are performed on different computing platforms. For example, the generation of ECG measurements (304) may be performed locally at a medical device, while producing the ECG image matrix (310-314) may occur at a remote computing device or system.

In some implementations, the method 300 begins with obtaining ECG signals from a wearable medical device (302). The ECG signals may be obtained from skin-facing ECG electrodes integrated into or connected to a wearable cardiac monitoring device, a cardiac holter monitor, or a cardiac monitoring and treatment device (e.g., with an automated external defibrillator or a wearable cardioverter defibrillator). The signals may be obtained by one or more processors of the wearable medical device. The signals, in another example, may be relayed via a network to a remote computing system such as a medical facility server or a cloud computing platform.

In some implementations, ECG measurements are generated from the ECG signals (304). The ECG measurements, for example, may include a variety of ECG features such as, in some examples, a set of R peaks, a set of P peaks, a set of T peaks, or a set of QRS complexes.

In some implementations, if cardio-vibrational measurements are available (306), a time scale of the cardio-vibrational measurements is registered with deflection features of the ECG measurements (308). In some examples, the time scale of the cardio-vibrational measurements may be registered with R peaks, P peaks, T peaks, and/or QRS complexes of the ECG reading. Registering the cardio-vibrational signal with the ECG reading, for example, may allow analysis of measurements obtained using both mechanisms, thereby supporting a more in-depth evaluation of cardiac condition. Further, registering the ECG reading with the cardio-vibrational measurements may be advantageous in enabling greater precision in the calculation of certain metrics, such as electromechanical activation time (EMAT) or left ventricular systolic time (LVST). In examples, a temporal component will also be used to determine if the ECG readings are changing over seconds, or minutes, or remaining stable.

In some implementations, the cardio-vibrational measurements are transformed into a cardio-vibrational image matrix (310). The cardio-vibrational measurements, for example, may be transformed into a cardio-vibrational image matrix as described in steps 110-116 of FIG. 1.

In some implementations, the ECG measurements are segmented into adjacent ECG portions (312). The set of the ECG measurements used in the transformation may represent a selected period of time (e.g., predetermined duration) such as, in some examples, 15 seconds, 30 seconds, or 45 seconds to be real-real-time responsive to cardiac conditions occurring in the heart of the patient such as arrhythmia, thereby supporting timely and responsive therapeutic support, such as defibrillation shock or pacing pulse delivery. In further examples, the selected period of time may be around 90 seconds, around 120 seconds, or around 2 or 3 minutes to allow for analysis of less frequent cardiac behaviors and/or longer periods of arrhythmic activity. In additional examples, the selected period of time may be at least 10 minutes for detailed analysis of heart failure and cardiac risk conditions, such as ejection fraction (EF) analysis or supraventricular tachycardia (SVT) classification. The predetermined duration, in further examples, may be between around 15 seconds and around 30 seconds, between around 30 seconds and around 45 seconds, between around 45 seconds and around 60 seconds, between around 60 seconds and around 90 seconds, between around 90 seconds and 120 seconds, between around 2 minutes or around 3 minutes, or between around 3 minutes and around 10 minutes. In examples, selection of the predetermined duration or the duration of the adjacent portions, e.g., adjacent ECG portions 312 can be automatically set based on self-learning of such durations for individual patients. For example, the medical device may automatically determine an appropriate value for the predetermined duration or the duration of the adjacent portions from an analysis of prior cardio-vibrational and/or ECG image matrices for the patient. In an illustration, if the device had previously assessed cardio-vibrational and/or ECG image matrices based on 45 second durations (x-axis), with 1 second segments (y-axis), and such assessments were used in prior machine-learning based classifications, then for ongoing and/or new classifications similar duration parameters can be used.

The identified set of ECG measurements, in some implementations, is segmented into the adjacent ECG portions (312). Each ECG portion, in some embodiments, represents a duration smaller than the predetermined duration such as, in some examples, around 100 milliseconds, around 1000 milliseconds, around 1 second, around 2 seconds, around 5 seconds, or around 10 seconds. The duration, in some embodiments, is selected to capture, in each ECG portion, a threshold number of deflection features, such as, in some examples, at least two R peaks of the ECG reading. The ECG portions, in further examples, may generally each have a duration spanning between around 1 millisecond and around 100 milliseconds, between 100 milliseconds and around 1000 milliseconds, between around 1 second and around 2 seconds, between around 2 seconds or around 5 seconds, or between around 5 seconds and around 10 seconds. The period of time represented by each ECG portion, in some implementations, may be selected in part based upon a type of analysis desired. For example, real-time arrhythmia monitoring may involve a shorter timeframe, while sudden cardiac arrest (SCA) risk prediction analysis may involve review of lengthier timeframes. The duration, for example, may correspond in part to a total duration of the set (e.g., a longer set of ECG measurements may correspond to a longer timeframe for each ECG portion of the set of ECG measurements). In examples, selection of the predetermined duration or the duration of the adjacent portions, e.g., adjacent ECG portions 312 can be automatically set based on self-learning of such durations for individual patients. For example, the medical device may automatically determine an appropriate value for the predetermined duration or the duration of the adjacent portions from an analysis of prior cardio-vibrational and/or ECG image matrices for the patient. In an illustration, if the device had previously assessed cardio-vibrational and/or ECG image matrices based on 45 second durations (x-axis), with 1 second segments (y-axis), and such assessments were used in prior machine-learning based classifications, then for ongoing and/or new classifications similar duration parameters can be used.

Figure 4:
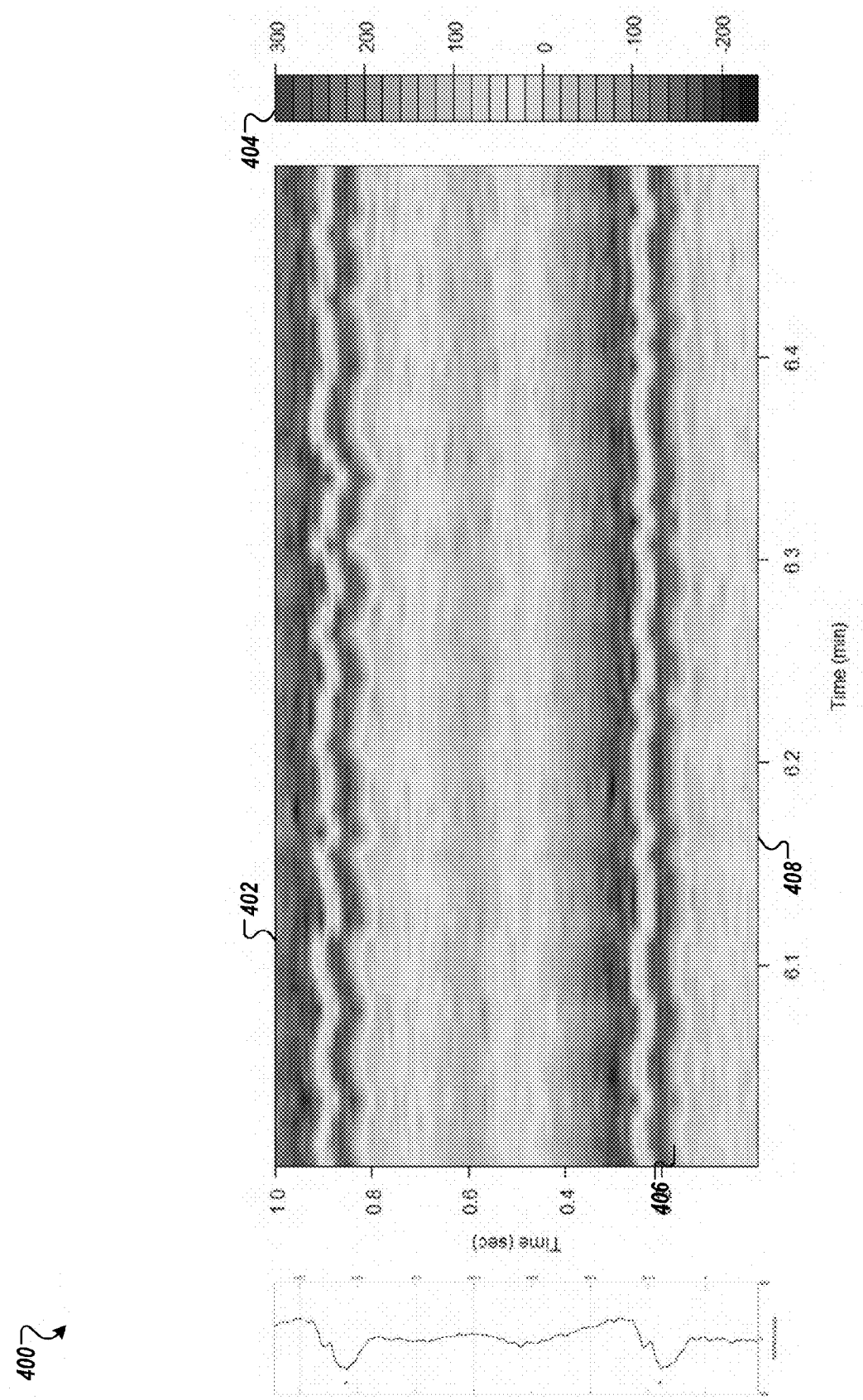
FIG. 4 illustrates an example ECG image matrix.

In some implementations, the ECG portions are plotted using pixel characteristic values mapped to parameter values of corresponding ECG measurements to produce an ECG image matrix (314). The pixel characteristic values, for example, may include pixel hue and/or pixel intensity. In an example, the color spectrum of the pixel characteristic values may include at least three colors, four colors, eight colors, or up to 16 colors. For example, as illustrated in FIG. 4, an example ECG image matrix 402 includes hues of yellow, orange, red, green, and blue pixels.

The pixel characteristic values, for example, may be arranged in a heat map to draw a clinician's attention to particularly relevant or important data, such as R peaks, P peaks, T peaks, and QRS complexes. As illustrated in FIG. 4, a pixel heat map scale 404 of the example ECG image matrix 402 illustrates a range of magnitude intensities ranging from blue to red. In another example, the pixel characteristic values may be mapped to distinct hues and/or intensities beneficial for automated analysis. The map of pixel characteristic values, in some embodiments, is selected from a set of maps of pixel characteristic values designed for different categories of parameter values, different types of interpretation, and/or highlighting different types of information. Plotting, for example, may involve creating a graphic representation of the mapped parameter values as a time progression of adjacent ECG portions plotted along a first axis of the ECG image matrix, where parameter values of individual ECG portions are plotted along a second axis of the ECG image matrix. Turning to FIG. 4, for example, the example ECG image matrix 402 includes ECG portions spanning 1 second each along a y-axis 406 over a 30 second duration of ECG measurements along an x-axis 408.

Returning to FIG. 3A, in some implementations, if a cardio-vibrational image matrix was generated (316), the ECG image matrix and the cardio-vibrational image matrix are applied to one or more machine learning classifiers to monitor a cardiac condition in the patient (318). If, instead, only an ECG image matrix was generated (316), in some implementations, the ECG matrix is applied to one or more machine learning classifiers to monitor a cardiac condition in the patient (320). The cardiac condition, for example, may include an arrhythmia condition. In some implementations, the ECG (and, optionally, the cardio-vibrational image matrix) is applied to multiple machine learning classifiers in parallel to screen for a number of potential cardiac conditions. In other implementations, the ECG image matrix (and, optionally, the cardio-vibrational image matrix) may be applied to a first machine learning classifier (e.g., to separate instances of noise from instances of an abnormality) then subsequently to one or more additional machine learning classifiers either serially or in parallel. Certain classifiers may be trained to apply only one of the two image matrices, while other machine learning classifiers are trained to apply both the ECG image matrix and the cardio-vibrational image matrix.

Turning to FIG. 3B, in some implementations, if an arrhythmia condition is detected (322) by the one or more machine learning classifiers, a type of arrhythmia is determined (324). For example, a first machine learning classifier may detect possibility of an arrhythmia (322) (e.g., abnormality). Responsive to the detection, one or more additional machine learning classifiers may be applied to determine a type of the arrhythmia (324). In a first example, the first machine learning classifier may detect possibility of an arrhythmia, while the second machine learning classifier determines whether the ECG measurements (and, optionally cardio-vibrational measurements) comprises indication of noise rather than presence of an arrhythmia. Thus, in a simplest form, determining the type of arrhythmia may correspond to determining presence of arrhythmia or a determination that the signals represent noise. In another example, machine learning classifiers may be provided to identify multiple types of arrhythmia, including, in some examples, supraventricular tachycardia (SVT), ventricular tachycardia, ventricular fibrillation, tachycardia, bradycardia, asystole, a heart pause condition, pulseless electrical activity, or atrial fibrillation.

In some implementations, if the type of arrhythmia corresponds to an erratic heart rate condition, tachycardia, bradycardia, asystole or pulseless electrical activity (PEA) (326), the wearable medical device is caused to is caused to select an appropriate pacing routine corresponding to the type of arrhythmia, culminating in delivery of pacing pulses (328). The medical device, for example, may be a wearable defibrillation device such as the device 1000 described below in relation to FIG. 10. In another example, the device may be a separate defibrillation device in communication with processing circuitry performing the method 300. In some implementations, after causing the wearable medical device to deliver the one or more pacing pulses, the method 300 then returns to obtaining ECG signals (302).

Where bradycardia is detected and the intrinsic cardiac rate of the patient is below that of a hysteresis rate of the patient, the medical device can be configured to pace the patient at a pre-set base pacing rate. During this time, the device will continue to monitor the patient's intrinsic heart rate and will withhold pacing pulses in the event that an intrinsic heart beat is detected within designated interval corresponding to the hysteresis rate, resulting in an on-demand pacing provided as maintenance pacing.

For responding to tachycardia, the medical device may additionally include another pacing rate, an anti-tachyarrhythmia pacing to rate, above which the device will identify that the patient is suffering from tachycardia, and will pace the patient in a manner to bring the patient's intrinsic heart back toward the base racing rate. For example, the device may employ a technique known as overdrive pacing wherein a series of pacing pulses (e.g., between about 5 and 10 pacing pulses) are delivered to the patient at a frequency above the intrinsic rate of the patient in an effort to gain control of the patient's heart rate. Once it is determined that the device is in control of the patient's heart rate, the rate (i.e., the frequency) of the pulses may be decremented, for example by about 10 ms, and another series of pacing pulses delivered. This delivery of pulses and the decrease in frequency may continue until the detected intrinsic cardiac rate of the patient is below the anti-tachyarrhythmia pacing rate, or at the base pacing rate.

For an erratic heart rate, the medical device may perform a type of pacing that is similar to a combination of maintenance pacing and overdrive pacing discussed above. For example, where the medical monitoring and treatment device detects an erratic heart rate with no discernable sinus rhythm, the device may deliver a series of pacing pulses (e.g., between about 5 and 10 pacing pulses) to the patient at a particular frequency. This frequency may be one that is above a lower frequency of a series of detected intrinsic beats of the patient's heart and below an upper frequency of the detected intrinsic beats of the patient's heart. After delivering the series of pulses, the device may monitor the patient's heart to determine if it has synchronized to the rate of the series of delivered pulses. Where the intrinsic rate of the patient's heart is still erratic, the device may increase the frequency of the series of pulses and deliver another series. This may continue until it is established that the patient's heart is now in a more regular state. Upon determining that the patient's heart is now in a more regular state, the device may perform maintenance pacing if it is determined that the patient's intrinsic heart rate is too low as described above, or perform pacing at a decremented rate, if such is warranted.

For responding to asystole or a detected condition of pulseless electrical activity, the medical monitoring and treatment device may perform maintenance pacing. This type of pacing would be performed after a series of one or more defibrillating shocks that attempt to restore a normal sinus rhythm to the heart of the patient.

In implementations, the medical device may be configured to perform a particular type of pacing only after a programmable delay after such cardiac arrhythmias are detected, or after a programmable period of time after one or more defibrillating shocks are delivered.

In some implementations, if the type of arrhythmia corresponds to a ventricular fibrillation or supraventricular tachycardia (330), the wearable medical device is caused to charge up the energy storage devices (e.g., capacitors) and deliver a defibrillation or cardioversion shock to the patient (332). The medical device, for example, may be a wearable therapeutic shock device such as the device 1000A described below in relation to FIG. 10A. In another example, the device may be a separate therapeutic shock device in communication with processing circuitry performing the method 300. In some implementations, after causing the wearable medical device to deliver the cardioversion or defibrillation shock, the method 300 returns to obtaining ECG signals (302).

If, instead, the type of arrhythmia is a heart pause condition, pulseless electrical activity, atrial fibrillation, or simply noise within the signal, in some implementations, the method 300 stores a portion of the ECG and/or cardio-vibrational signal in memory of the medical device, and returns to obtaining ECG signals (302). In implementations, the stored portion of the ECG and/or cardio-vibrational signal can be transmitted to a remote server for analysis and/or display via a viewing terminal to a caregiver, technician, or other authorized person.

Although described as a particular series of operations, in other implementations, the method 300 includes more or fewer steps. For example, rather than being a separate arrhythmia type determination step (324), in other embodiments, applying the ECG image matrix (318 or 320) includes detecting a condition such as an arrhythmia type. Further, in some embodiments, certain steps of the method 300 may be performed in a different order or simultaneously. For example, while the ECG measurements (and cardio-vibrational measurements) are being generated and transformed into the ECG image matrix (and cardio-vibrational image matrix) (304-314), previously created image matrices may be applied to the machine learning classifiers (318 or 320), and next set of ECG signals may be obtained (302). Other modifications are possible while remaining within the scope and the spirit of the method 300.

Figure 5:
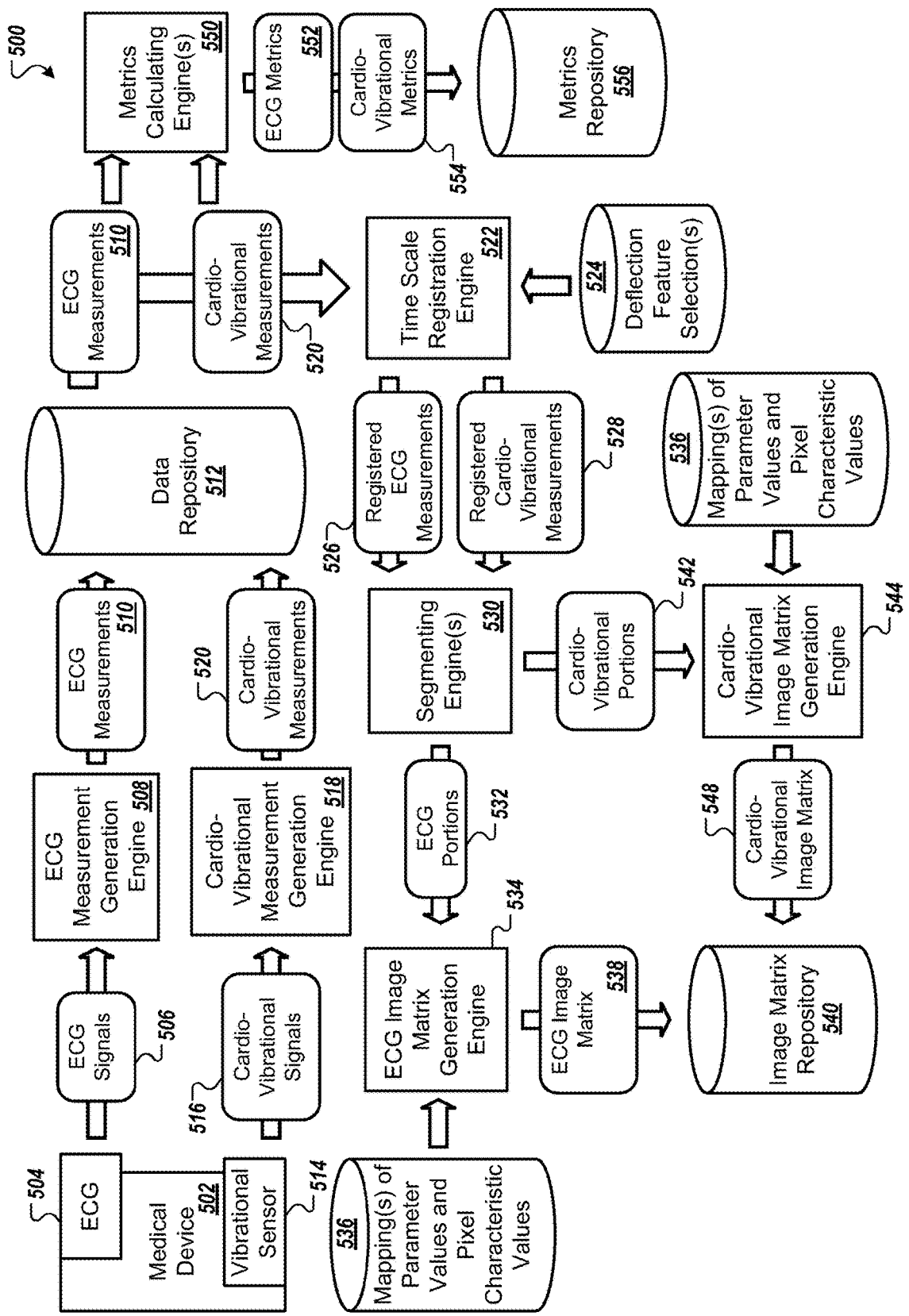
FIG. 5 is a flow diagram of an example process for collecting signals from a wearable medical device and forming image matrices and supporting metrics for monitoring a cardiac condition in a patient.

FIG. 5 is a flow diagram of an example process 500 for collecting signals from a wearable medical device 502 and forming both image matrices and supporting metrics for monitoring a cardiac condition in a patient. The process 500, in some examples, may be performed by processing circuitry of the medical device 502 such as a wearable medical device, by one or more processors of a server or server system, or by one or more processors of a cloud computing platform. Portions of the process 500, in some embodiments, are performed on different computing platforms. The process 500 includes a number of engines. Each engine may represent one or more software algorithms, computer-implemented functions, and/or hardware logic routines. Each engine may be configured to be executed as processing commands executed on processing circuitry and/or routines implemented as a specialized circuit design, such as a programmable logic chip design.

In some implementations, the process 500 begins with obtaining ECG signals 506 from an ECG monitoring unit 504 and cardio-vibrational signals 516 from a vibrational sensor 514 of a medical device 502. The medical device 502, for example, may be one of the medical devices 1100A-1100D described below in relation to FIGS. 11A-11D. The ECG signals 506, for example, may be obtained by ECG electrodes integrated into or connected to a cardiac monitoring device, as described in relation to step 302 of the method 300 of FIG. 3A. The ECG electrodes, for example, may be the electrodes 1022 described in relation to FIG. 10 or electrodes 1112 described in relation to FIGS. 11A-11D. The cardio-vibrational signals 516, for example, may be obtained by one or more vibrational sensors monitoring a patient's heart, as described, for example, in relation to step 102 of the method 100 of FIG. 1. The one or more vibrational sensors may include the sensors 1024, 1026, and/or 1030 described in greater detail below in relation to FIG. 10.

In some implementations, the ECG signals 506 are provided to an ECG measurement generation engine 508 to generate ECG measurements 510. The ECG measurements 510, for example, may be generated as described in relation to step 304 of the method 300 of FIG. 3A.

In some implementations, the cardio-vibrational signals 516 are provided to a cardio-vibrational measurement generation engine 518 to generate cardio-vibrational measurements 520. The cardio-vibrational measurements 520, for example, may be generated as described in relation to step 104 of FIG. 1.

In some implementations, the ECG measurements 510 and the cardio-vibrational measurements 520 are stored to a data repository 512 by the ECG measurement generation engine 508 and the cardio-vibrational measurement generation engine 518, respectively.

The ECG measurements 510 and the cardio-vibrational measurements 520, in some implementations, are accessed by a time scale registration engine 522 to generate a set of registered ECG measurements 526 which are time registered to a set of registered cardio-vibrational measurements 528. The time scale registration engine 522, the registered measurements 526, 528, for example, may be generated as described in step 108 of the method 100 of FIG. 1 and/or step 308 of the method 300 of FIG. 3A. The time scale registration engine 522 may obtain one or more deflection feature selections 524 for registering the ECG measurements 510 with the cardio-vibrational measurements 520. The deflection feature selections 524, in an illustrative example, may default to registering based on R peaks captured in the ECG measurements 510. This default registration, for example, may be selected in view of R peaks being typically readily identified within an ECG signal. In further examples, the deflection feature selections can include P peaks, T peaks, and/or QRS complexes of the ECG measurements 510.

In some implementations, the registered ECG measurements 526 and the registered cardio-vibrational measurements 528 are provided to at least one segmenting engine 530 to segment the registered measurements 526 and 528 into ECG portions 532 and cardio-vibrational portions 542, respectively. The segmenting engine(s) 530, for example, may segment the registered measurements 526 and 528 as described in relation to step 110 of the method 100 of FIG. 1 and/or step 312 of the method 300 of FIG. 3A.

In some implementations, the ECG portions 532 are provided to an ECG image matrix generation engine 534 for generating an ECG image matrix 538. The ECG image matrix 538 may be produced by the ECG image matrix generation engine 534, for example, as described in relation to step 314 of the method 300 of FIG. 3A. The ECG image matrix generation engine 534 may use a mapping of parameter values and pixel characteristic values 536 for mapping ECG measurements within each of the ECG portions to corresponding pixel characteristic values.

In some implementations, the ECG image matrix 538 is stored to an image matrix repository. The ECG image matrix 538, for example, may be stored in a database structure identifying the source (e.g., patient identifier), time stamp, and one or more links to corresponding ECG measurements 510 and/or registered ECG measurements 526. In another example, a portion of this information, such as the time stamp and the patient identifier, may be stored as meta data in the image file structure. The ECG image matrix 538, in some embodiments, is stored in a lossless image file structure such as, for example, a PNG file which retains the original information accurately. In other embodiments, the ECG image matrix 538 is stored as a lossy (e.g., compressed) image file format such as a JPG file, to reduce storage demands for retaining historic image matrix files.

In some implementations, the cardio-vibrational portions 542 are provided to a cardio-vibrational image matrix generation engine 544 for generating a cardio-vibrational image matrix 548. The cardio-vibrational image matrix 548, for example, may be generated as described in relation to steps 112-116 of the method 100 of FIG. 1 and/or step 310 of the method 300 FIG. 3A. The cardio-vibrational image matrix generation engine 544 may use a mapping of parameter values and pixel characteristic values 536 for mapping cardio-vibrational measurements within each of the cardio-vibrational portions to corresponding pixel characteristic values.

In some implementations, the cardio-vibrational image matrix 548 is stored to the image matrix repository 540. The cardio-vibrational image matrix 548, for example, may be stored in a database structure identifying the source (e.g., patient identifier), time stamp, and one or more links to corresponding cardio-vibrational measurements 520 and/or registered cardio-vibrational measurements 528. In another example, a portion of this information, such as the time stamp and the patient identifier, may be stored as meta data in the image file structure. The cardio-vibrational image matrix 548, in some embodiments, is stored in a lossless image file structure such as, for example, a PNG file which retains the original information accurately. In other embodiments, the cardio-vibrational image matrix 548 is stored as a lossy (e.g., compressed) image file format such as a JPG file, to reduce storage demands for retaining historic image matrix files.

In some implementations, the ECG measurements 510 and the cardio-vibrational measurements 520 are provided to one or more metrics calculating engines 550 to calculate ECG metrics 552 and cardio-vibrational metrics 554. The ECG metrics 522, in some examples, may include heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or a shape of morphology of the ECG information, cosine R-T, artificial pacing, QT interval, QT variability, T wave width, T wave alternans, T-wave variability, and/or ST segment changes. The cardio-vibrational metrics 554 may include, in some examples, cardio-vibrational signal values including any one or all of S1, S2, S3, and S4, electromechanical activation time (EMAT), average EMAT, percentage of EMAT (% EMAT), systolic dysfunction index (SDI), and/or left ventricular systolic time (LVST).

In some implementations, the ECG metrics 552 and the cardio-vibrational metrics 554 are stored to a metrics repository 556. The ECG metrics 552 and the cardio-vibrational metrics 554, for example, may be stored in a database structure identifying the source (e.g., patient identifier), time stamp, and one or more links to corresponding ECG measurements 510, cardio-vibrational measurements 520, registered ECG measurements 526, and/or registered cardio-vibrational measurements 528. The metrics repository 556, the data repository 512, and the image matrix repository 540, in some embodiments, are each configured as part of a database of information generated using data supplied by sensors such as the ECG sensors 504 and the vibrational sensor(s) 514 of the medical device 502.

Figure 8:
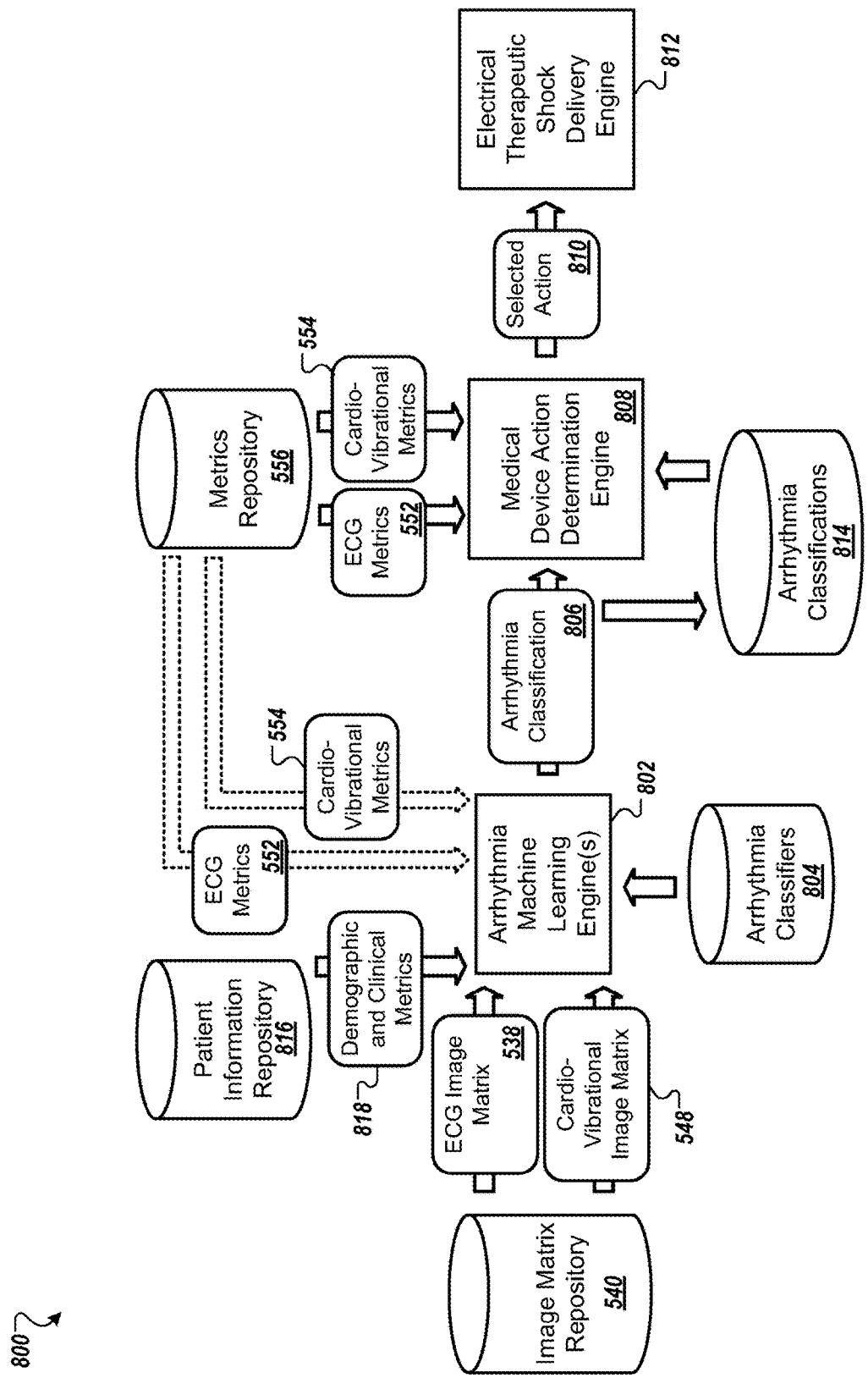
FIG. 8 is a flow diagram of an example process for applying machine learning classifiers to ECG image matrices and to cardio-vibrational image matrices to automatically determine whether to apply an electrical therapeutic shock to a patient.

FIG. 8 is a flow diagram of an example process 800 for applying machine learning classifiers to ECG image matrices and to cardio-vibrational image matrices to automatically determine whether to apply an electrical therapeutic shock to a patient. The process 800 is advantageous in that it is more timely than human review and is less subjective than human review. Further, the process 800, in applying machine learning engines to the image matrices, may develop a more accurate and more refined interpretation of the heart condition of the patient than had previously been achieved through ECG measurement analysis and/or other sensor analysis. The process 800 includes a number of engines. Each engine may represent one or more software algorithms, computer-implemented functions, and/or hardware logic routines. Each engine may be configured to be executed as processing commands executed on processing circuitry and/or routines implemented as a specialized circuit design, such as a programmable logic chip design.

In some implementations, one or more arrhythmia machine learning engines 802 access the ECG image matrix 538 and/or the cardio-vibrational image matrix 548 from the image matrix repository 540. For example, as discussed in relation to step 318 or step 320 of the method 300 of FIG. 3A, the arrhythmia machine learning engine(s) 802 may apply the image matrices 538, 548 to one or more machine learning classifiers to monitor a cardiac condition. Advantageously, the arrhythmia machine learning engine(s) 802 may execute upon one or more graphics processing units (GPUs) to accelerate analysis of the ECG image matrix 538 and/or the cardio-vibrational image matrix 548. The arrhythmia machine learning engine(s) 802 may access a set of arrhythmia classifiers 804 for classifying the contents of ECG image matrices and/or cardio-vibrational image matrices as corresponding to a type of arrhythmia.

The classifiers 804, in some embodiments, include one or more ECG classifiers 804 trained using a truth base of ECG image matrices each produced using a same mapping of parameter values and pixel characteristic values as applied to producing the ECG image matrix 538. Additionally, ECG image matrices of the truth base used in training the ECG classifier(s) 804 may have been produced using an ECG portion duration matching the ECG portion duration of the ECG image matrix 538. In a further example, the ECG image matrices of the truth base used in training the ECG classifier(s) 804 may have been produced using a same deflection feature registration to align the plotting of the ECG image matrix 538.

In some embodiments, the classifiers 804 include one or more cardio-vibrational classifiers 804 trained using a truth base of cardio-vibrational image matrices each produced using a same mapping of parameter values and pixel characteristic values as applied to producing the cardio-vibrational image matrix 548. Additionally, cardio-vibrational image matrices of the truth base used in training the cardio-vibrational classifier(s) 804 may have been produced using a cardio-vibrational portion duration matching the cardio-vibrational portion duration of the cardio-vibrational image matrix 548. In a further example, the cardio-vibrational image matrices of the truth base used in training the cardio-vibrational classifier(s) 804 may have been produced using a same deflection feature registration to align the plotting of the cardio-vibrational image matrix 548.

In some embodiments, the classifiers 804 include one or more co-registered classifiers 804 trained using a truth base of ECG matrices co-registered with cardio-vibrational image matrices (e.g., aligned along a y-axis or an x-axis as a single training image to demonstrate commonalities in cardiac signatures between the two types of matrices). As discussed above, each image matrix of the truth base, prior to co-registration, may have been produced using a same mapping of parameter values and pixel characteristic values as applied to producing the image matrix 538 or 548, a same portion duration as applied to producing the image matrix 538 or 548, and or a same deflection feature for registering alignment between the ECG image matrix 538 and the cardio-vibrational image matrix 548.

In some implementations, the arrhythmia classifiers 804 include separate arrhythmia classifiers trained from a truth base designed to identify each of supraventricular tachycardia (SVT), ventricular tachycardia, ventricular fibrillation, tachycardia, bradycardia, asystole, a heart pause condition, pulseless electrical activity, and/or atrial fibrillation. Thus, the arrhythmia classifiers 804, in an illustrative example, may include an ECG SVT classifier, an ECG ventricular tachycardia classifier, an ECG ventricular fibrillation classifier, an ECG tachycardia classifier, an ECG bradycardia classifier, an ECG asystole classifier, an ECG heart pause condition classifier, an ECG pulseless electrical activity classifier, an ECG atrial fibrillation classifier, a cardio-vibrational SVT classifier, a cardio-vibrational ventricular tachycardia classifier, a cardio-vibrational ventricular fibrillation classifier, a cardio-vibrational tachycardia classifier, a cardio-vibrational bradycardia classifier, a cardio-vibrational asystole classifier, a cardio-vibrational heart pause condition classifier, a cardio-vibrational pulseless electrical activity classifier, a cardio-vibrational atrial fibrillation classifier, a co-registered SVT classifier, a co-registered ventricular tachycardia classifier, a co-registered ventricular fibrillation classifier, a co-registered tachycardia classifier, a co-registered bradycardia classifier, a co-registered asystole classifier, a co-registered heart pause condition classifier, a co-registered pulseless electrical activity classifier, and/or a co-registered atrial fibrillation classifier.

In some embodiments, the classifiers 804 include a normal heart condition classifier. The normal heart condition classifier, for example, may be trained using historic ECG image matrices and/or historic cardio-vibrational image matrices of the patient, thereby including the unique "fingerprint" of the cardiac cycles of the patient. Further, in certain embodiments, other of the classifiers 804 may be trained in part using historic image matrices derived from the patient. Patient-derived classifier(s) 804, for example, may be advantageous in training the arrhythmia machine learning engine(s) 802 to recognize arrhythmia states in comparison to the unique features of the patient's cardiac cycles.

Additionally, or alternatively, in implementations, the machine learning engines(s) 802 can receive inputs apart from the image matrices for use in the classification (illustrated in FIG. 8 using dotted arrows). Examples of ECG metrics that can be used to aid in the classification process include average heart rate, minimum heart rate, maximum heart rate, average RR interval in milliseconds or seconds, minimum RR interval in milliseconds or seconds, maximum RR interval in milliseconds or seconds, standard deviation of RR intervals in milliseconds or seconds, number of successive RR intervals greater than a predetermined duration (e.g., 45 ms) per minute, heart rate turbulence information (e.g., onset, slope, etc.), average QRS duration, standard deviation of QRS duration, average QT interval, standard deviation of QT intervals, number of premature ventricular contractions (PVCs), and number of consecutive sequences of PVCs. Examples of cardio-vibrational metrics include S1, S2, S3, and S4 intensities, EMAT, % EMAT, LVST, % LVST, heart murmur information, among others. Examples of demographic and clinical metrics 818 that can be used to aid in the classification process include age, patient gender, clinical status, e.g., explant of an implanted cardiac device, coronary artery disease patient or previously operated on, prior myocardial infarction condition, prior VT/VF event(s), among others. The demographic and clinical metrics 818, for example, may be accessed from a patient information repository 816.

In some embodiments, at least a portion of the arrhythmia machine learning engine(s) 802 include one or more deep neural network (DNN) models configured to apply at least a portion of the classifiers 804. DNN models, for example, perform regression and classification on data input, potentially proving more successful where the classifiers 804 are combined with additional metrics to classify the image matrices 538, 548. In some embodiments, at least a portion of the arrhythmia machine learning engine(s) 802 include one or more convolution neural network (CNN) models configured to apply at least a portion of the classifiers 804. CNN models, for example, are designed to break down features of an image into sub-features, making CNN classification particularly advantageous for image classification. In some embodiments, at least a portion of the arrhythmia machine learning engine(s) 802 include one or more network in network (NiN) models configured to apply at least a portion of the classifiers 804. NiN models, for example, take CNN processing to another level by analyzing a network of convolutional layers of an image, proving advantageous for image classification. Other deep learning models may be applied, with the particular deep learning model being selected, in some examples, based in part on processing availability and storage size availability in the end system (e.g., a cloud network versus processing on a medical device), third party tool access (e.g., availability of cloud provider specialized tools and hardware for performing image classification), and/or processor type (e.g., GPU, CPU, FPGA, etc.).

In some embodiments, different image matrices are applied to identify different types of arrhythmia. For example, heart pause and pulseless electrical activity may be readily apparent using a single image matrix, such as the ECG image matrix 538, while other arrhythmias (e.g., discerning between SVT and noise) may benefit from combined analysis of both the ECG image matrix 538 and the cardio-vibrational image matrix 548.

The arrhythmia machine learning engine(s) 802, in some embodiments, are executed concurrently. For example, the arrhythmia machine learning engine(s) 802 may include a separate engine for each type of arrhythmia, with all types of arrhythmia scanned for in parallel by the arrhythmia machine learning engine(s) 802 to determine the type of arrhythmia (or lack thereof, e.g., a determination of noise or of normal matrix plot pattern) as an arrhythmia classification 806. In some embodiments, the arrhythmia machine learning engine(s) 802 store the arrhythmia classification 806 to a repository of historic arrhythmia classifications 814. The arrhythmia classification 806, in some embodiments, includes a duration and/or a rate of arrhythmia. The duration and/or rate, for example, may be relative (e.g., short, medium, long, slow, fast, etc.) or precise (e.g., number of seconds, number of heartbeats per second, etc.). For example, the arrhythmia classifiers 804 may include, for one or more types of arrhythmia, duration and/or rate refinements to more accurately classify the arrhythmia captured in the ECG image matrix 538 and/or the cardio-vibrational image matrix 548. In one illustration, the heart rate associated with the bradycardia or tachycardia may be determined to aid in selecting a pacing routine as an action 810. The arrhythmia machine learning engine(s) 802 may apply one or more metrics in determining a refined arrhythmia classification 806. The additional metrics, in some examples, can include ECG metrics, cardio-vibrational metrics, and/or other physiological metrics (e.g., breathing, blood pressure, body temperature, glucose level, tissue fluid, lung vibrations, etc.). The additional metrics, for example, may be supplied by the medical device 502 (e.g., as described further below).

In some implementations, the arrhythmia machine learning engine(s) 802 provide the arrhythmia classification 806 to a medical device action determination engine 808. The medical device action determination engine 808, responsive to receiving the arrhythmia classification 806, determines a selected action 810. The selected action 810 may involve, in some examples, doing nothing, collecting additional monitoring data (e.g., additional ECG image matrices and cardio-vibrational image matrices) to monitor subsequent activity to determine whether a condition is ongoing, issuing a warning to a clinician, caretaker, and/or wearer of a cardiac monitoring device, or issuing a command to an electrical therapeutic shock delivery engine 812 to deliver therapy to the patient. In an illustrative example, as described in relation to steps 322-332 of the method 300 of FIG. 3B, the arrhythmia classification may be used to determine whether to activate defibrillation or to select a pacing routine.

In some implementations, the medical device action determination engine 808 accesses ECG metrics 552 and/or cardio-vibrational metrics 554 from the metrics repository 556 to support the determination of the selected action 810. For example, the arrhythmia classification 806 may be analyzed in light of heart rate metrics, heart rate variability metrics, PVC burden or counts, atrial fibrillation burden metrics, pauses, heart rate turbulence, QRS height, QRS width, cosine R-T, artificial pacing, QT interval, QT variability, T wave width, T wave alternans, T-wave variability, ST segment changes, electromechanical activation time (EMAT), average EMAT, percentage of EMAT (% EMAT), systolic dysfunction index (SDI), and/or left ventricular systolic time (LVST). In some embodiments, further metrics are derived from other sensors of the medical device, such as a radio-frequency sensor, thermal sensor, one or more medical grade microphones, and/or one or more accelerometers.

The further metrics, in some examples, may relate to blood oxygen level, body temperature, glucose levels, tissue fluid levels (e.g., thoracic fluid content), lung vibrations and/or breath vibrations, sleep related parameters (e.g., snoring, sleep apnea), blood pressure, arterial pulse, and/or heart wall movement. For example, a rhythm with a low blood pressure could be treated differently than the same rhythm with a normal blood pressure. The same may be true for blood oxygen levels and thoracic fluid content. In a particular illustration, the rate of the arrhythmia may be determined from the heart rate metrics and/or heart rate variability metrics to support selection of an appropriate treatment routine. In some embodiments, the medical device action determination engine 808. The metrics 552 and 554, in some embodiments, include historic metrics derived from a timeframe prior to a timeframe represented in the ECG image matrix 538 and/or the cardio-vibrational image matrix 548. For example, the metrics 552 and/or 554 may inform the medical device action determination engine 808 regarding a patient's state leading up to the arrhythmia classification 806. In some embodiments, the metrics 552 and 554 are representative of a same or similar timeframe as the timeframe represented in the ECG image matrix 538 and/or the cardio-vibrational image matrix 548.

In some implementations, the medical device action determination engine 808 accesses one or more historic arrhythmia classifications 814 from a timeframe prior to the timeframe represented in the ECG image matrix 538 and/or the cardio-vibrational image matrix 548. For example, the selected action 810 on a prior round of execution of the process 800 may have been to continue to monitor, while, in determining that the condition has persisted, the medical device action determination engine 808 may determine, in the current round of execution, to command an electrical shock therapeutic delivery engine 812 to deliver a selected course of therapy.

Figure 10:
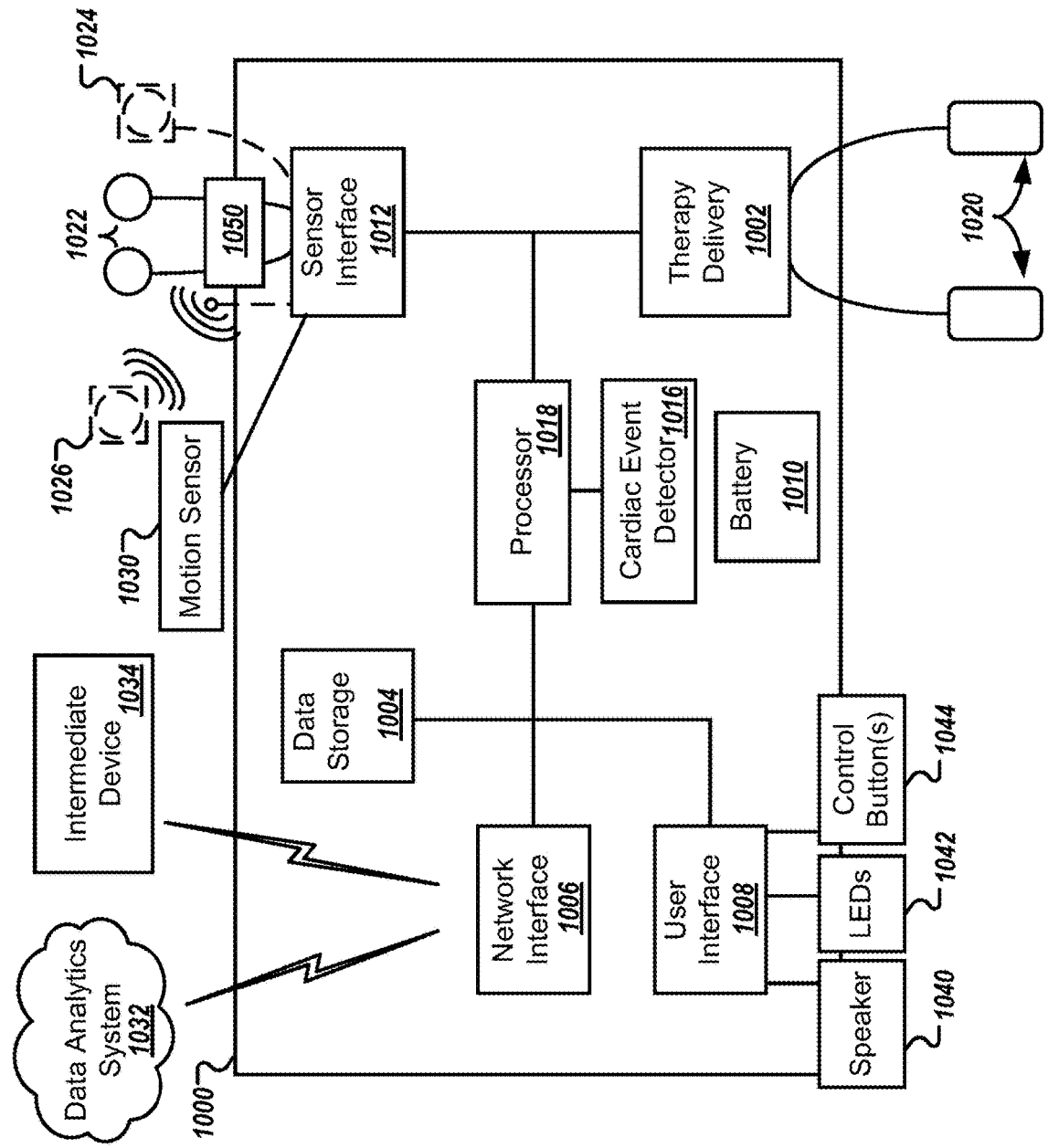
FIG. 10 is a block diagram of an example medical device for monitoring a cardiac condition of a patient.

In some implementations, the selected action 810 is provided to the electrical therapeutic shock delivery engine 812 for providing therapy to the patient. As discussed in relation to step 328 of the method 300 of FIG. 3B, the selected action 810 may be providing a defibrillating shock. In another example, as discussed in relation to step 332 of the method 300 of FIG. 3B, the selected action 810 may be a pacing routine corresponding to the arrhythmia classification 806. The electrical therapeutic shock delivery engine 812, for example, may be part of therapy delivery circuitry 1002 of a medical device controller 1000 of FIG. 10 or part of a processor 1018 commanding the therapy delivery circuitry 1002, as illustrated in FIG. 10.

In some implementations where electrical therapeutic shock is indicated by the selected action 810, the process 800 is configured to cause delivery of the electrical therapeutic shock in between 30 seconds and around two minutes after onset of the arrhythmia condition. In some examples, electrical therapeutic shock may be delivered within a minute to two minutes of arrhythmia onset, between thirty seconds and one minute of arrhythmia onset, under thirty seconds of arrhythmia onset, or between around 5 seconds and around 30 seconds of arrhythmia onset.

Figure 6:
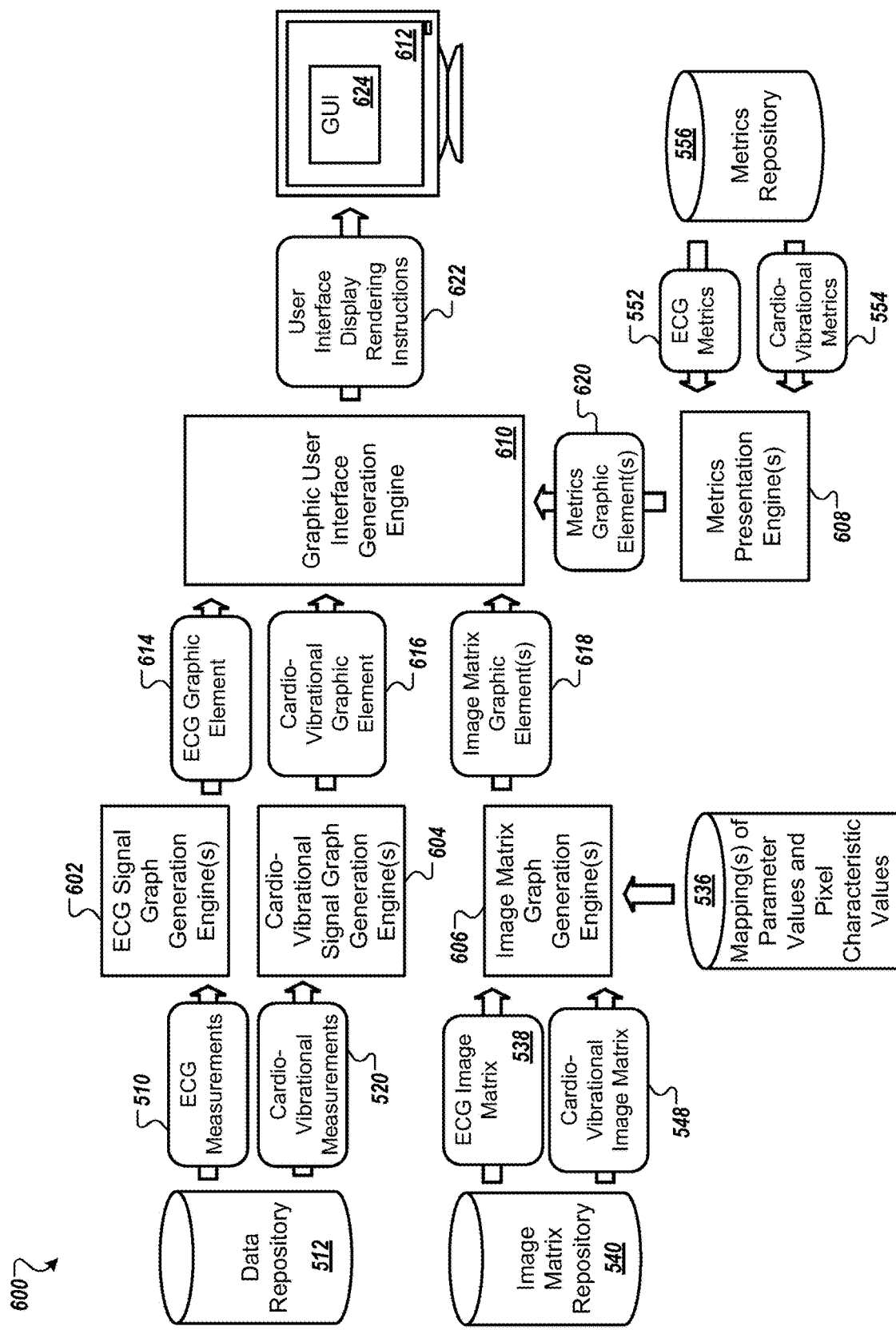
FIG. 6 is a flow diagram of an example process for presenting image matrix data for review by a clinician.

FIG. 6 is a flow diagram of an example process 600 for presenting image matrix data for review by a clinician. The process 600, in some examples, may be performed at least in part by processing circuitry of a medical device such as a wearable medical device, by one or more processors of a server or server system, or by one or more processors of a cloud computing platform. Portions of the process 600, in some embodiments, are performed on different computing platforms. The process 600 includes a number of engines. Each engine may represent one or more software algorithms, computer-implemented functions, and/or hardware logic routines. Each engine may be configured to be executed as processing commands executed on processing circuitry and/or routines implemented as a specialized circuit design, such as a programmable logic chip design.

In some implementations, one or more ECG signal graph generation engines 602 access the ECG measurements 510 from the data repository 512 and generate, from the ECG measurements 510, an ECG graphic element 614. The ECG graphic element 614, for example, may be an ECG graphic element 704 of the user interface 700 of FIG. 7A or an ECG graphic element 724 of a user interface 720 of FIG. 7B.

Figure 7A:
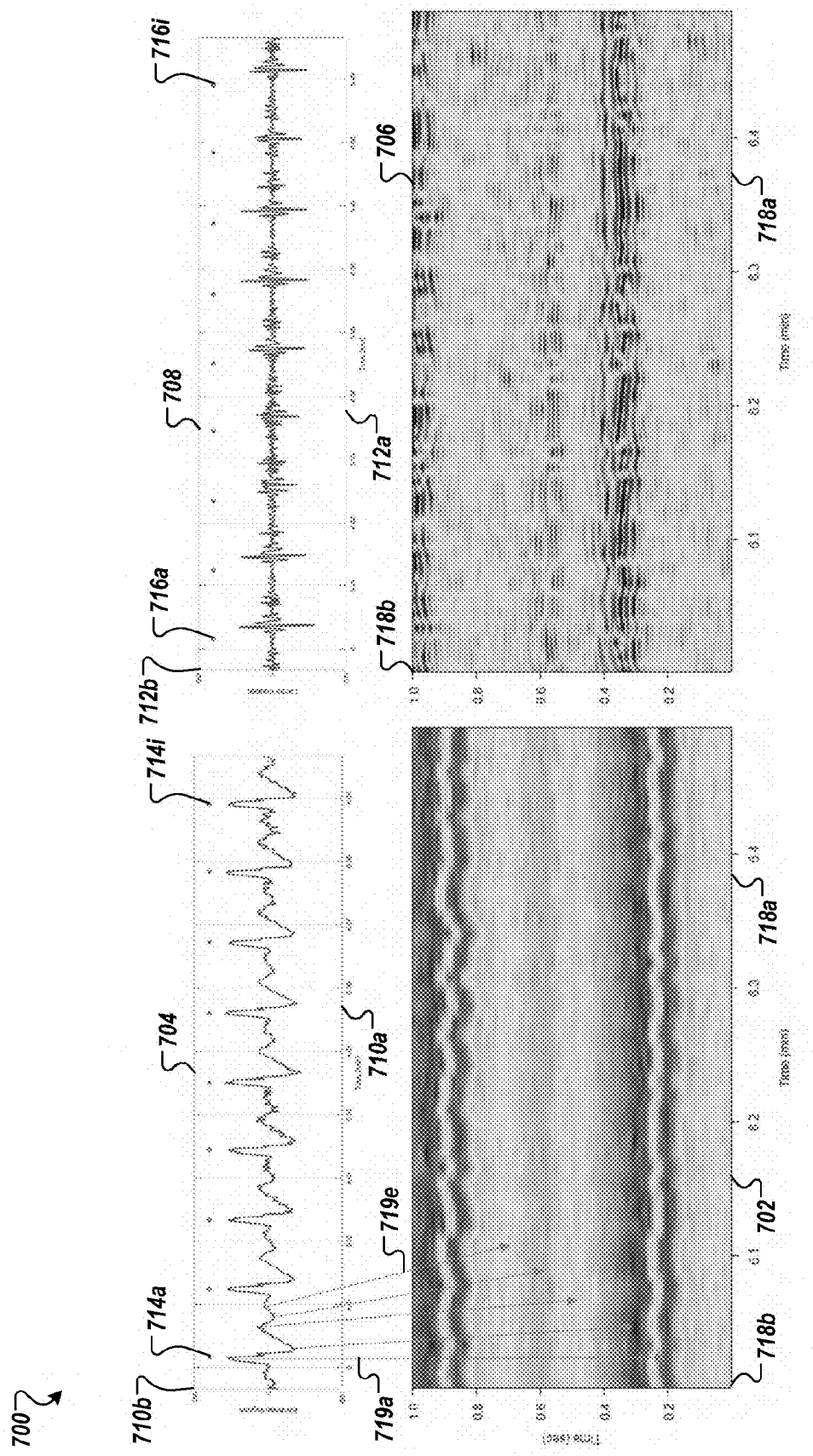
FIGS. 7A and 7B illustrate example graphic output representing an ECG image matrix and a cardio-vibrational image matrix for clinician review.

The ECG graphic element 614 may represent an electrocardiogram (e.g., a graph of voltage versus time) covering at least a portion of the time span of the ECG image matrix 538. For example, the ECG graphic element 704 of FIG. 7A includes a time scale along an x-axis 710a, and a voltage magnitude along the y-axis 710b. The time scale is 6 seconds along the x-axis, as demonstrated by the x-axis 710a (with readings spanning from 6 mins to about 6.1 mins). The time scale of ECG graphic element 704 tends to be shorter than the time scale for the ECG image matrix (as noted, 6 seconds, when compared to 30 seconds for the ECG image matrix 702), and as such an ECG reviewer will need to review multiple additional ECG graphic elements 704. This is one of the advantages of reviewing ECG data in the form of the ECG image matrix elements 702. For example, conventionally ECG technicians review beat-by-beat ECG waveforms. Such review can take much time to review, for example, over 24 hours of ECG data. With the image matrix representation, the ECG technician review is easier to identify arrhythmia or abnormal beats with longer time scale than beat-to-beat ECG representation. Rather than or in addition to the ECG measurements 510, in some embodiments, the ECG signal graph generation engine(s) 602 access the registered ECG measurements 526 of FIG. 5 (e.g., from the data repository 512). As illustrated in FIG. 7A, for example, deflection features 714a-i are arranged above the ECG signal plot in the graph 704. Deflection features included in the ECG graphic element 614 may correspond to the deflection feature selection(s) 524 provided to the time scale registration engine 522 of FIG. 5. Similarly, turning to FIG. 7B, the ECG graphic element 724, plotted on an x-axis 730a against time (e.g., 21.5 mins to 21.6 mins) and against voltage on a y-axis 730b, also includes a series of deflection points 734a-i. The deflection points 734a-i, for example, may represent R peaks of the registered ECG measurements 526.

Returning to FIG. 6, in some implementations, one or more cardio-vibrational signal graph generation engines 604 access the cardio-vibrational measurements 520 from the data repository 512 and generate, from the cardio-vibrational measurements 520, a cardio-vibrational graphic element 616. The cardio-vibrational graphic element 616, for example, may be a cardio-vibrational graphic element 708 of the user interface 700 of FIG. 7A or a cardio-vibrational graphic element 728 of a user interface 720 of FIG. 7B. The cardio-vibrational graphic element 616 may represent a cardio-vibrational signal (e.g., a graph of cardio-vibrations versus time) covering at least a portion of the time span of the cardio-vibrational image matrix 548. For example, the cardio-vibrational graphic element 708 of FIG. 7A includes a time scale along an x-axis 712a, and a voltage magnitude along the y-axis 712b. The time scale for the cardio-vibrational graphic element 708 of FIG. 7A is 6 seconds along the x-axis, as demonstrated by the x-axis 712*a* (with readings spanning from 21.5 mins to about 21.6 mins). Similar to the ECG image graphic element described above, the time scale of the cardio-vibrational graphic element 708 tends to be shorter than the time scale for the cardio-vibrational image matrix graphic element 706 (as noted, 6 seconds, when compared to 30 seconds for the cardio-vibrational image matrix graphic element 706), and as such a reviewer will need to review multiple additional cardio-vibrational image matrix graphic elements 706. This is one of the advantages of reviewing cardio-vibrational data in the form of the cardio-vibrational image matrix graphic elements 706. For example, conventionally ECG technicians review beat-by-beat ECG waveforms. Such review can take much time to review, for example, over 24 hours of cardio-vibrational data. With the image matrix representation, the technician review is easier to identify arrhythmia or abnormal cardio-vibrational patterns with longer time scale than beat-to-beat cardio-vibrational representation. Rather than or in addition to the cardio-vibrational measurements 520, in some embodiments, the cardio-vibrational signal graph generation engine(s) 604 access the registered cardio-vibrational measurements 528 of FIG. 5 (e.g., from the data repository 512). As illustrated in FIG. 7A, for example, deflection features 716*a-i* are arranged above the cardio-vibrational signal plot in the graph 708. Deflection features included in the cardio-vibrational graphic element 616 may correspond to the deflection feature selection(s) 524 provided to the time scale registration engine 522 of FIG. 5. Similarly, turning to FIG. 7B, the cardio-vibrational graphic element 728, plotted on an x-axis 712*a* against time (e.g., 6 mins to 6.1 mins) and against voltage on a y-axis 712*b*, also includes a series of deflection points 736*a-i*. The deflection points 734*a-i*, for example, may represent R peaks of the registered ECG measurements 526.

In some implementations, one or more image matrix graph generation engines 606 access the ECG image matrix 538 and the cardio-vibrational image matrix 548 from the image matrix repository 540 and produce one or more image matrix graphic elements 618. In some embodiments, producing an image matrix graphic element 618 includes applying one or more enhancements to the image matrix to improve visual interpretation by a human. As discussed in relation to step 116 of the method 100 of FIG. 1, for example, the image matrix graph generation engine(s) 606 may apply a filtering or smoothing algorithm to the image matrix. The image matrix graphic elements 618, for example may include, in addition to the image matrix plots represented in the ECG image matrix 538 and the cardio-vibrational image matrix 548, time scale representations or markers and/or deflection feature representations or markers. For example, as illustrated in FIG. 7A, each of the ECG image matrix 702 and the cardio-vibrational image matrix 706 includes an x-axis 718*a* (30 seconds) and a y-axis 718*b* (1 second). Further, turning to FIG. 7B, the cardio-vibrational image matrix 726 includes a set of S-value identifiers 738*a*-738*d* marking approximate locations of the S1, S2, S3, and S4 values within the cardio-vibrational image matrix 726. The image matrix graph generation engine(s) 606 may further access the mapping(s) of parameter values to pixel characteristic values 536. For example, the image matrix graph generation engine(s) 606 may access or generate a graphic heat map key such as the heat map key 216 of the cardio-vibrational image matrix display 210 of FIG. 2B or the heat map key 404 of the ECG image matrix display 400 of FIG. 4.

In some implementations, one or more metrics presentation engines 608 access the ECG metrics 552 and/or the cardio-vibrational metrics 554 from the metrics repository 556 and generate one or more metrics graphic elements 620. The metric graphic element(s) 620, in some examples, may include heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and/or ST segment changes. The metric graphic element(s) 620, in further examples, may include cardio-vibrational signal values including any one or all of S1, S2, S3, and S4, electromechanical activation time (EMAT), average EMAT, percentage of EMAT (% EMAT), systolic dysfunction index (SDI), and/or left ventricular systolic time (LVST). The metric graphic element(s) 620 may be represented as one or more graphs, tables, or markings upon one or more of the ECG graphic element 614, the cardio-vibrational graphic element 616, or the image matrix graphic element(s) 618.

In some implementations, a graphic user interface generation engine 610 obtains the ECG graphic element 614, cardio-vibrational graphic element 616, image matrix graphic element(s) 618, and/or metrics graphic element(s) 620 and produces user interface display rendering instructions 622 for rendering a graphic user interface (GUI) 624 upon a display 612 of a computing device for review by a user such as a clinician. The graphic interface 624, in some examples, may include the interface 200 of FIG. 2A, the interface 210 of FIG. 2B, the interface 400 of FIG. 4, the interface 700 of FIG. 7A, or the interface 720 of FIG. 7B. Turning to FIG. 7A, a set of illustrative arrows 719*a*-719*e* (depicted herein for illustrative purposes, and do not necessarily form part of the interface 700) demonstrate correspondence to portions of the ECG graph 704 and color bands of the ECG image matrix 702. The user interface display rendering instructions 622, in some examples, can include one or more browser-renderable files such as hyper-text markup language (HTML) files, Java Script (JS) files, Java Script Style Sheets (JSS) files, Cascading Style Sheets (CSS) files, and/or links to data and/or graphics for presenting information on the display 612. The user interface display rendering instructions 622, in some implementations, are updated in near real-time by the process 600 to continuously generate display elements 614, 616, 618, and/or 620 while current image matrices 538, 548 and measurements 510, 520 are received. The user interface display rendering instructions 622, for example, may render a moving graphic visually plotting up-to-date information for the user's review. In further embodiments, the user interface display rendering instructions 622 include download instructions for obtaining a report file, such as a portable document format (PDF) file or Visio spreadsheet including a combined report generated by the graphic user interface generation engine 610. Rather than sending the user interface display rendering instructions 622 to render the GUI 624 to the display 612, in further embodiments, the report file may be shared electronically with a user through email, printing, facsimile, or other electronic communications.

Figure 7B:
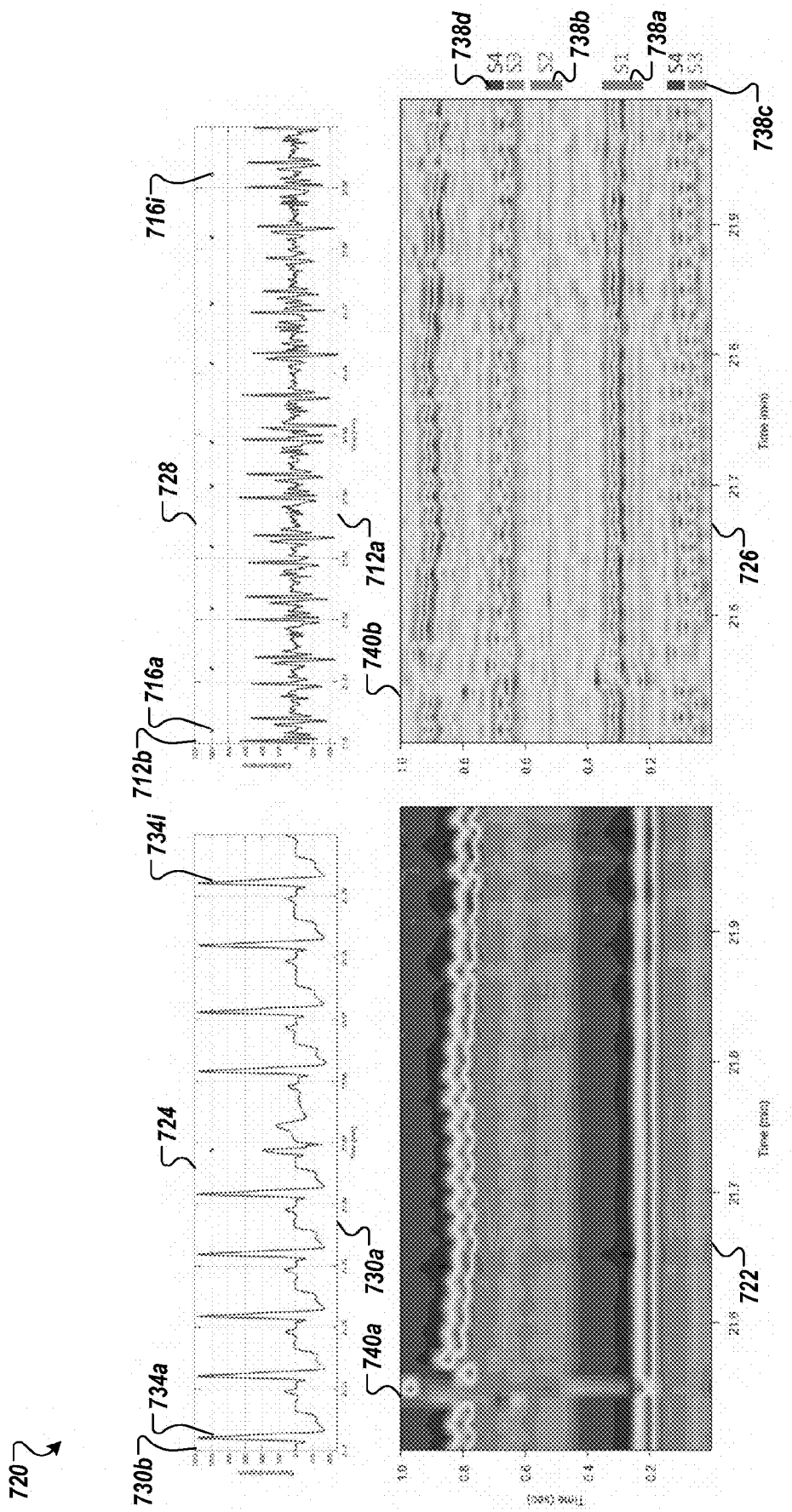

In some implementations, a user reviewing the GUI 624 identifies one or more anomalies in the images. For example, as illustrated in FIG. 7B, a timing anomaly 740 (e.g., an ectopic beat) shows up around 21.55 minute point of both the ECG image matrix 722 and the cardio-vibrational image matrix 726. As further illustrated in FIG. 7B, the S3 and/or S4 bands 738c, 738d are indicative of heart failure. Advantageously, while it would be difficult to visually analyze the S3 bands 738c or the S4 bands 738d from the cardio-vibrational graph 728, the cardio-vibrational image matrix 726 provides the end user a clear indication of problem regions (e.g., such as the fluctuating S3 738c and/or S4 738d).

Figure 9A:
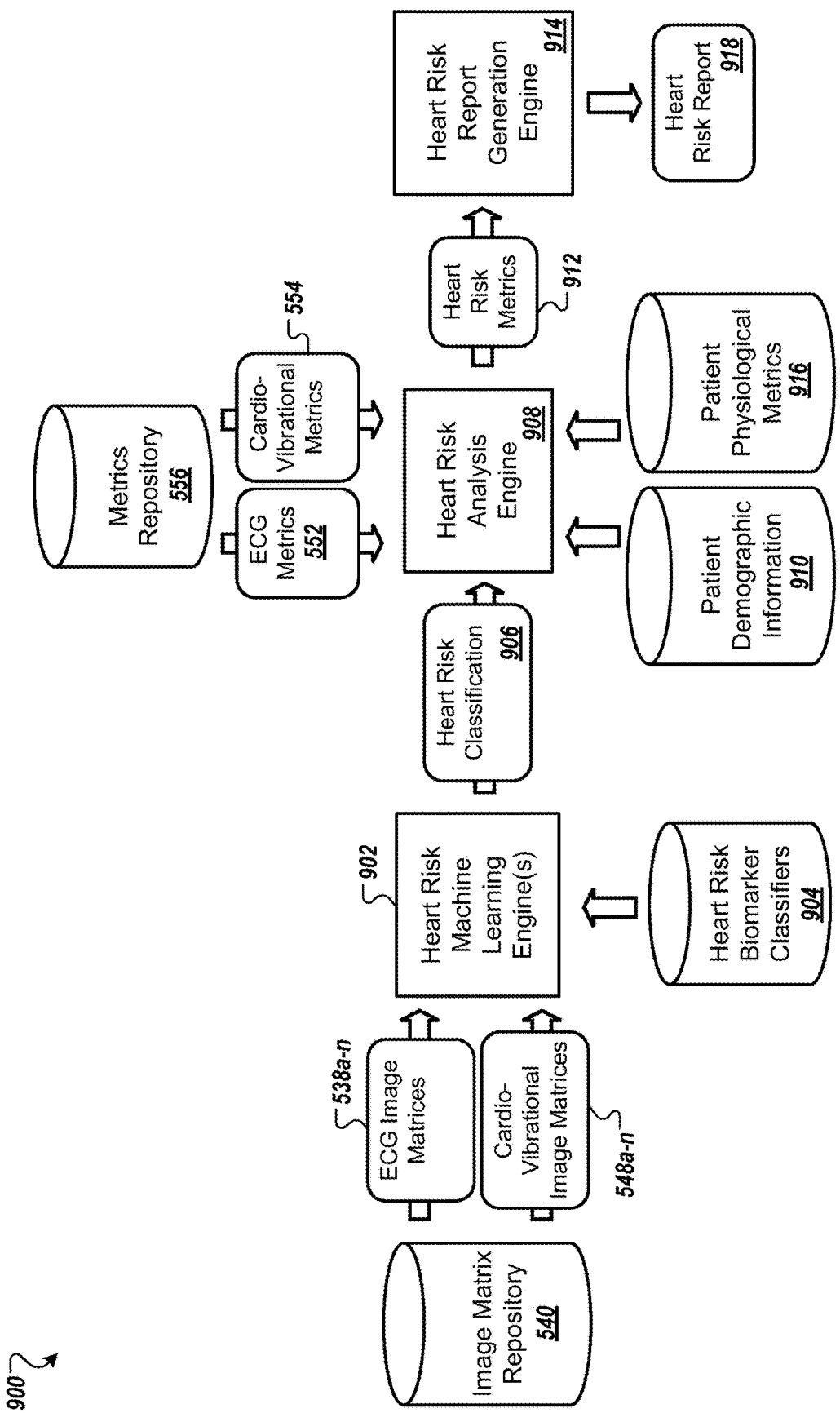
FIGS. 9A and 9B are flow diagrams of example processes for applying machine learning classifiers to ECG image matrices and to cardio-vibrational image matrices to analyze heart risk in a patient.
Figure 9B:
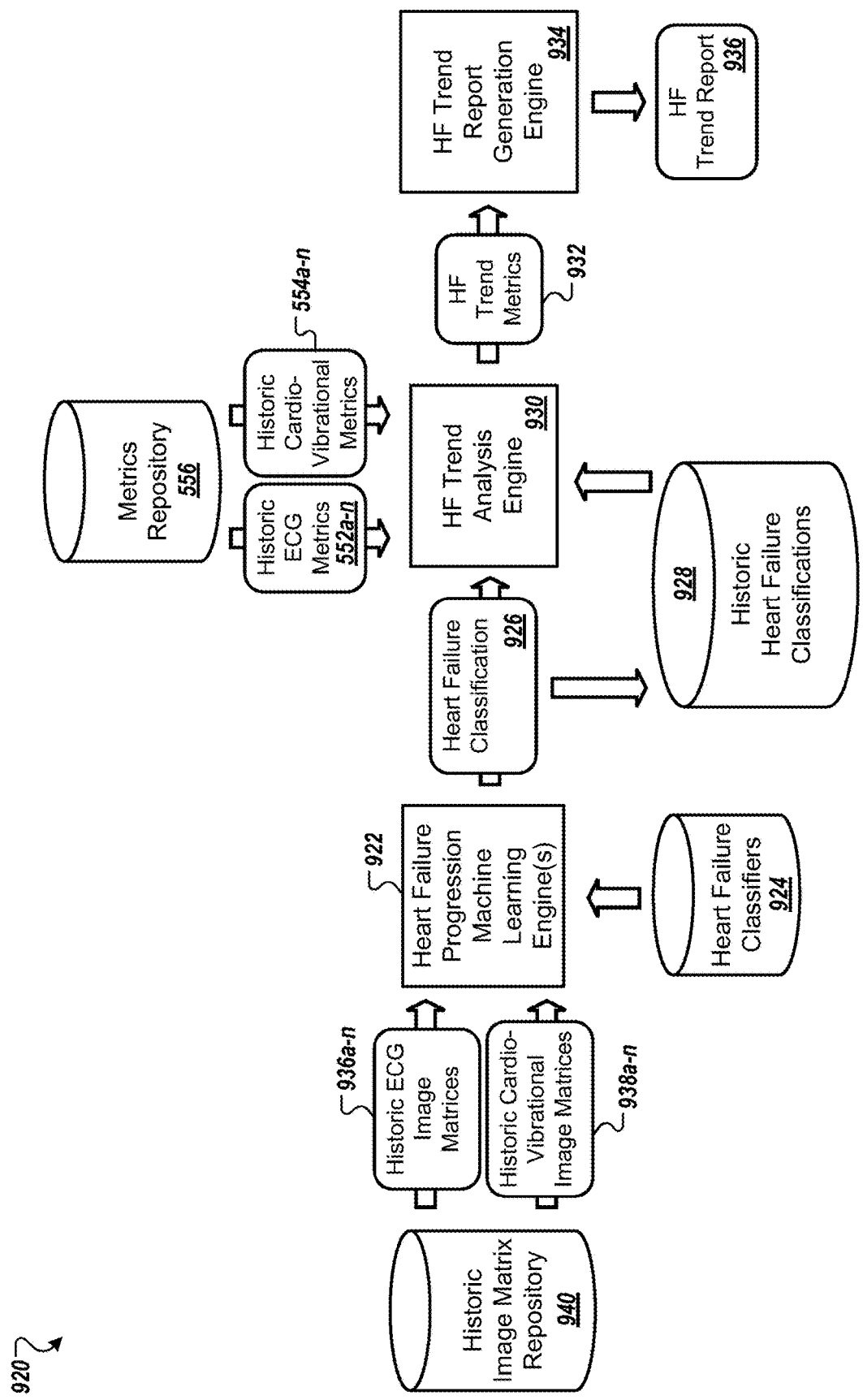

FIGS. 9A and 9B are flow diagrams of example processes 900 and 920 for applying machine learning classifiers to ECG image matrices and to cardio-vibrational image matrices to analyze heart risk in a patient. The processes 900 and 920 include a number of engines. Each engine may represent one or more software algorithms, computer-implemented functions, and/or hardware logic routines. Each engine may be configured to be executed as processing commands executed on processing circuitry and/or routines implemented as a specialized circuit design, such as a programmable logic chip design.

Turning to FIG. 9A, a process 900 is illustrated for analyzing potential heart risk in a patient based upon a number of cardiac risk biomarkers. The process 900, for example, may provide advance warning of cardiac risk based upon screening for the biomarkers through machine learning analysis of a set of ECG image matrices 538a-n and/or a set of cardio-vibrational image matrices 548a-n. The process 900, for example, may be used to monitor patient health, determine a best course of treatment, and/or manage appropriate follow up care for a patient based upon a prediction of risk of future cardiac disease or disorder. The process 900 advantageously uses a set of cardiac risk biomarker classifiers 904 developed through machine learning techniques, along with other health metrics, to provide a predictive assessment of the patient's future cardiac health. Further, as more information is learned regarding correspondence between cardiac patterns and future cardiac outcomes through ongoing training of the cardiac risk biomarker classifiers 904, the process 900 becomes more and more refined in its heart risk predictive analysis.

In some implementations, the process 900 begins with one or more heart risk machine learning engines 902 obtaining the set of ECG image matrices 538a-n and the set of cardio-vibrational image matrices 548a-n from the image matrix repository 540. The sets of image matrices 538a-n and 548a-n, in some embodiments, represent a substantially time-contiguous set of image matrices representing, together, a number of adjacent periods of time over a monitoring period. The adjacent periods of time, for example, may be directly adjacent, partially overlapping, or separated by a time gap (e.g., representing a time until a next deflection feature for aligning the next cardio-vibrational image matrix 548x with the next ECG image matrix 548x). In some embodiments, the sets of image matrices 538a-n and 548a-n represent a series of discrete periods of time captured throughout the monitoring period. The discrete periods of time, in some examples, may extend between around 15 seconds and around 30 seconds, between around 30 seconds and around 45 seconds, between around 45 seconds and around 60 seconds, between around 60 seconds and around 90 seconds, between around 90 seconds and 120 seconds, between around 2 minutes or around 3 minutes, or between around 3 minutes and around 10 minutes.

The sampling intervals throughout the monitoring period for capturing the discrete periods of time, in some examples, can include a periodic sampling, an activity-based sampling capturing one or more patient activities (e.g., sampling during high activity, sampling during sleep, etc.), and/or a patient-triggered sampling (e.g., patient activates a control on a user interface on or in communication with a wearable cardiac monitoring device to trigger sampling whenever experiencing one or more symptoms). The monitoring period may extend from about three hours to about one month. The monitoring period, in some examples, may cover at least one hour, around one hour to three hours, around three hours to twelve hours, around twelve hours to one day, around one day to three days, around three days to one week, around one week to one month, or around one month to three months.

In some implementations, the heart risk machine learning engine(s) 902 determine at least one heart risk classification 906 through applying a set of cardiac risk biomarker classifiers 904 to the sets of image matrices 538a-n and 548a-n. Advantageously, the heart risk machine learning engine(s) 902 may execute upon one or more graphics processing units (GPUs) to accelerate analysis of the sets of image matrices 538a-n and 548a-n. The set of cardiac risk biomarker classifiers 904, in some examples, may be trained to detect cardiac risk biomarkers associated with sudden cardiac arrest (SCA), low ejection fraction (EF), or a stage of heart failure. The cardiac risk biomarkers, in some examples, may include EMAT (e.g., over 120 milliseconds), LVST (e.g., under 0.001), S3 intensity (e.g., at or above 5), S3 width, pre-ejection period (PEP), and/or ejection time (ET). In some examples, the cardiac risk biomarkers include thoracic fluid index and a percentage of lung fluid over a period of time.

The cardiac risk biomarker classifiers 904 associated with SCA, in some embodiments, are trained to detect ventricular fibrillation (VF), ventricular tachycardia (VT), pulseless electrical activity (PEA), and/or asystole. The cardiac risk biomarker classifiers 904 associated with low EF, in some embodiments, are trained to detect a less than 35% classification, a 35 to 39% classification, and a 40% to 54% classification. The heart failure stages, in some embodiments, align with the New York Heart Association (NYHA) heart failure classifications. The NYHA classifications are as follows:

Class I—No symptoms and no limitation in ordinary physical activity, e.g. shortness of breath when walking, climbing stairs etc.

Class II—Mild symptoms (mild shortness of breath and/ or angina) and slight limitation during ordinary activity.

Class III—Marked limitation in activity due to symptoms, even during less-than-ordinary activity, e.g. walking short distances (20-100 m). Comfortable only at rest.

Class IV—Severe limitations. Experiences symptoms even while at rest. Mostly bedbound patients.

The cardiac risk biomarker classifiers 904, in some embodiments, include one or more ECG classifiers 904 trained using a truth base of ECG image matrices each produced using a same mapping of parameter values and pixel characteristic values as applied to producing the ECG image matrices 538a-n. Additionally, ECG image matrices of the truth base used in training the ECG classifier(s) 904 may have been produced using an ECG portion duration matching the ECG portion duration of the ECG image matrices 538a-n. In a further example, the ECG image matrices of the truth base used in training the ECG classifier(s) 904 may have been produced using a same deflection feature registration to align the plotting of the ECG image matrices 538a-n.

In some embodiments, the cardiac risk biomarker classifiers 904 include one or more cardio-vibrational classifiers 904 trained using a truth base of cardio-vibrational image matrices each produced using a same mapping of parameter values and pixel characteristic values as applied to producing the cardio-vibrational image matrices 548*a-n*. Additionally, cardio-vibrational image matrices of the truth base used in training the cardio-vibrational classifier(s) 904 may have been produced using a cardio-vibrational portion duration matching the cardio-vibrational portion duration of the cardio-vibrational image matrices 548*a-n*. In a further example, the cardio-vibrational image matrices of the truth base used in training the cardio-vibrational classifier(s) 904 may have been produced using a same deflection feature registration to align the plotting of the cardio-vibrational image matrices 548*a-n*.

In some embodiments, the cardiac risk biomarker classifiers 904 include one or more co-registered classifiers 904 trained using a truth base of ECG matrices co-registered with cardio-vibrational image matrices (e.g., aligned along a y-axis or an x-axis as a single training image to demonstrate commonalities in cardiac signatures between the two types of matrices). As discussed above, each image matrix of the truth base, prior to co-registration, may have been produced using a same mapping of parameter values and pixel characteristic values as applied to producing the image matrices 538*a-n* or 548*a-n*, a same portion duration as applied to producing the image matrices 538*a-n* or 548*a-n*, and or a same deflection feature for registering alignment between the ECG image matrices 538*a-n* and the cardio-vibrational image matrices 548*a-n*.

In some implementations, the cardiac risk biomarker classifiers 904 include separate cardiac risk biomarker classifiers trained from a truth base designed to identify each of VF, VT, PEA, asystole, less than 35% EF, 35 to 39% EF, 40% to 54% EF, class I HF, class II HF, class III HF, and class IV HF. Thus, the cardiac risk biomarker classifiers 904, in an illustrative example, may include an ECG VF classifier, an ECG VT classifier, an ECG PEA classifier, an ECG asystole classifier, an ECG less than 35% EF classifier, an ECG 35 to 39% EF classifier, an ECG 40% to 54% EF classifier, an ECG class I HF classifier, an ECG class II HF classifier, an ECG class III HF classifier, an ECG class IV HF classifier, a cardio-vibrational VF classifier, a cardio-vibrational VT classifier, a cardio-vibrational PEA classifier, a cardio-vibrational asystole classifier, a cardio-vibrational less than 35% EF classifier, a cardio-vibrational 35 to 39% EF classifier, a cardio-vibrational 40% to 54% EF classifier, a cardio-vibrational class I HF classifier, a cardio-vibrational class II HF classifier, a cardio-vibrational class III HF classifier, a cardio-vibrational class IV HF classifier, a co-registered VF classifier, a co-registered VT classifier, a co-registered PEA classifier, a co-registered asystole classifier, a co-registered less than 35% EF classifier, a co-registered 35 to 39% EF classifier, a co-registered 40% to 54% EF classifier, a co-registered class I HF classifier, a co-registered class II HF classifier, a co-registered class III HF classifier, and/or a co-registered class IV HF classifier.

In some embodiments, the cardiac risk biomarker classifiers 904 include a normal heart condition classifier. The normal heart condition classifier, for example, may be trained using historic ECG image matrices and/or historic cardio-vibrational image matrices of the patient, thereby including the unique "fingerprint" of the cardiac cycles of the patient. Further, in certain embodiments, other of the cardiac risk biomarker classifiers 904 may be trained in part using historic image matrices derived from the patient. Patient-derived cardiac risk biomarker classifier(s) 904, for example, may be advantageous in training the heart risk machine learning engine(s) 902 to recognize cardiac anomalies in comparison to the unique features of the patient's cardiac cycles.

In some embodiments, at least a portion of the heart risk machine learning engine(s) 902 include one or more deep neural network (DNN) models configured to apply at least a portion of the cardiac risk biomarker classifiers 904. In some embodiments, at least a portion of the heart risk machine learning engine(s) 902 include one or more convolution neural network (CCN) models configured to apply at least a portion of the cardiac risk biomarker classifiers 904. In some embodiments, at least a portion of the heart risk machine learning engine(s) 902 include one or more network in network (NiN) models configured to apply at least a portion of the cardiac risk biomarker classifiers 904. Other deep learning models may be applied, with the particular deep learning model being selected, in some examples, based in part on processing availability and storage size availability in the end system (e.g., a cloud network versus processing on a medical device), third party tool access (e.g., availability of cloud provider specialized tools and hardware for performing image classification), and/or processor type (e.g., GPU, CPU, FPGA, etc.).

In some embodiments, different image matrices are applied to identify different types of cardiac risk biomarkers. In examples, the cardio-vibrational signals are all those that are solely or include in the calculation any cardiac data from a vibrational sensor, including S1, S2, S3, S4, EMAT, SDI, among others.

The heart risk learning engine(s) 902, in some embodiments, are executed concurrently. For example, the heart risk learning engine(s) 902 may include a separate engine for each of at least SCA, HF, and EF, with the separate engines executing in parallel to determine evidence of any or all of SCA, HF, and EF. The positive identifiers (e.g., classifier matches), in some implementations, are combined as a heart risk classification 906. The heart risk classification 906, for example, may include a feature vector or binary code indicating a corresponding "match" or "no match" related to each of the cardiac risk biomarker classifiers 904. In another example, the heart risk classification 906 may include a nuanced analysis, including information regarding confidence levels associated with various matching cardiac risk biomarker classifiers 904. The heart risk learning engine(s) 902, in some implementations, apply weightings related to one or more of the cardiac risk biomarker classifiers 904 in determining the heart risk classification 906. For example, in relation to SCA, VF and VT may be weighted less than PEA and asystole, since treatability and likelihood of survival are more promising with VF and VT. The weightings may be based, in part, upon a confidence the heart risk machine learning engine(s) 902 have in the identified match for each of one or more of the cardiac risk biomarker classifiers 904. For example, in machine learning analysis, matches of a particular input to a classifier are associated with a score, or confidence rating, in how close the match appears. At some point, the confidence rating may be so low that the heart risk learning engine(s) 902 consider the outcome to be a non-match (e.g., 65% certainty, between 70% and 85% certainty, below 95% certainty, etc.). In other ranges, the confidence rating may be at a threshold for inclusion but weighted lower than a higher confidence rating. In an illustrative example, below 70% certainty may be considered a non-match, between 70% and 85% a possible match, between 85% and 95% a probable match, and over 95% a confident match.

Each of possible, probable, and confident may be associated with a different weighting for formulating the heart risk classification 906.

In some implementations, the heart risk classification 906 is provided to a heart risk analysis engine 908 for analysis in view of patient demographic information 910 as well as ECG metrics 552 and/or cardio-vibrational metrics 554 accessed from the metrics repository 556. The patient demographic information 910, in some examples, may include gender, age, height, weight, and/or BMI. Further, the patient demographic information 910 may include diseases or disorders such as, in some examples, diabetes, anemia, renal failure, sleep apnea, and/or cognitive disfunction. The heart risk analysis engine 908, in some embodiments, further considers additional patient physiological metrics 916. The patient physiological metrics 916, in some examples, may include breathing, blood pressure, body temperature, glucose level, tissue fluid, and/or lung vibrations. The additional metrics, for example, may be supplied by the medical device 502 of FIG. 5 (e.g., as described further in the Example Medical Devices for Monitoring a Patient's Heart Condition section, below).

The heart risk analysis engine 908, in some embodiments, generates heart risk metrics 912. The metrics, in some implementations, include values calculated from the ECG image matrices 538a-n and/or the cardio-vibrational image matrices 548a-n. For example, upon indication, in the heart risk classification 906, that the EMAT, LVST, S3 intensity, and/or S3 width is potentially indicative of heart risk, mathematical calculations may be generated by the heart risk analysis engine 908 using the image matrices 538a-n and/or 548a-n to apply a valuation to the abnormality. In some implementations, the metrics include values obtained from the ECG metrics 552 and/or cardio-vibrational metrics 554. The heart risk metrics 912, further, may include calculations performed using mathematical algorithms to quantify heart risk based upon the heart risk classification 906, patient physiological metrics 916, and/or patient demographic information 910. In an illustrative example, based on a heart risk classification 906 indicating significant risk of SCA, ECG metrics 552 and/or cardio-vibrational metrics 554 may be provided to an algorithm, as well as patient demographics 910 and/or patient physiological metrics 916, to quantify the risk in light of other known information regarding the patient. The metrics, in some implementations, include metrics pertaining to each of the areas screened for using the cardiac risk biomarker classifiers 904 (e.g., SCA, EF, and HF).

In some implementations, a heart risk report generation engine 914 combines the heart risk metrics 912 in a report 918 for review by a clinician and/or patient. The report 918, for example, may include metrics 912 such as heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or a shape of morphology of the ECG information, cosine R-T, artificial pacing, QT interval, QT variability, T wave width, T wave alternans, T-wave variability, and/or ST segment changes. The metrics 912 presented in the report 918, in further examples, may include cardio-vibrational signal values including any one or all of S1, S2, S3, and S4, electromechanical activation time (EMAT), average EMAT, percentage of EMAT (% EMAT), systolic dysfunction index (SDI), and/or left ventricular systolic time (LVST). Certain metrics 912 may be represented in the heart risk report 918 as one or more graphs and/or tables.

In some implementations, the heart risk report generation engine 914 produces user interface display rendering instructions for rendering the heart risk report 918 as a graphic user interface (GUI) upon a display of a computing device for review by a user such as a clinician. In some implementations, the heart risk report 918 is generated by the heart risk report generation engine 914 as a report file, such as a portable document format (PDF) file or Visio spreadsheet. The heart risk report generation engine 914 may provide the report to a computer display, to a printer, or to an electronic communications contact (e.g., email address), in some examples.

Turning to FIG. 9B, a process 920 is illustrated for analyzing heart failure trends in a patient based upon a number of heart failure biomarkers. The process 920, for example, may provide an objective assessment of heart failure progression in the patient based upon screening for the biomarkers through machine learning analysis of a set of historic ECG image matrices 538a-n and/or a set of historic cardio-vibrational image matrices 548a-n. The process 920, for example, may be used to monitor patient health, determine whether a course of treatment appears to be successful in mitigating worsening of heart failure, and/or manage appropriate follow up care for a patient based upon a present assessment of heart failure trends in the patient. The process 920 advantageously uses a set of heart failure biomarker classifiers 924 developed through machine learning techniques, along with other health metrics, to provide an objective analysis of heart failure trends in the patient. Further, as more information is learned regarding correspondence between cardiac patterns and degeneration of heart condition through the classes or stages of heart failure through ongoing training of the heart failure biomarker classifiers 924, the process 920 becomes more and more refined in its heart failure trend analysis.

In some implementations, the process 920 begins with one or more heart failure progression machine learning engines 922 obtaining a set of historic ECG image matrices 936a-n and a set of historic cardio-vibrational image matrices 938a-n from a historic image matrix repository 940. The sets of historic image matrices 936a-n and 938a-n, for example, may include the image matrices 538a-n and/or 548a-n used to perform heart risk analysis in accordance to the process 900 of FIG. 9A. The sets of image matrices 936a-n and 938a-n, in some embodiments, include one or more image matrices 936a-n and 938a-n captured on each capture period of a series of capture periods. Image matrices from a given capture period, as described in relation to FIG. 9A, may represent a substantially time-contiguous set of image matrices, or a series of discrete periods of time captured throughout the given capture period. The capture periods, in some examples, may cover at least one hour, around one hour to three hours, around three hours to twelve hours, around twelve hours to one day, around one day to three days, or around three days to one week. In some implementations, the capture periods are periodic. For example, the capture periods may be every week, every other week, every month, every other month, every three months, or every six months. The capture periods may correspond to check-up visits with a surgeon, doctor, or other clinician. The series of capture periods, in some embodiments, grow as the patient continues to be monitored. For example, upon a first execution of the process 920 for the patient, the series of capture periods may represent two capture periods. For the next analysis, the patient's image matrices 936*a-n* and 938*a-n* may represent three capture periods, and so on.

In some implementations, the heart failure progression machine learning engine(s) 922 determine at least one heart failure classification 926 through applying a set of heart failure classifiers 924 to the sets of historic image matrices 936*a-n* and 938*a-n*.

Advantageously, the heart failure progression machine learning engine(s) 922 may execute upon one or more graphics processing units (GPUs) to accelerate analysis of the sets of historic image matrices 936*a-n* and 938*a-n*. The set of heart failure classifiers 924, in some examples, may be trained to detect heart failure biomarkers associated with a stage of heart failure. The heart failure stages, in some embodiments, align with the New York Heart Association (NYHA) heart failure classifications. The NYHA classifications are as follows:

Class I—No symptoms and no limitation in ordinary physical activity, e.g. shortness of breath when walking, climbing stairs etc.

Class II—Mild symptoms (mild shortness of breath and/or angina) and slight limitation during ordinary activity.

Class III—Marked limitation in activity due to symptoms, even during less-than-ordinary activity, e.g. walking short distances (20-100 m). Comfortable only at rest.

Class IV—Severe limitations. Experiences symptoms even while at rest. Mostly bedbound patients.

For example, the heart failure classifiers 924 may include a portion of the heart risk classifiers 904.

In some implementations, the set of heart failure biomarker classifiers 924 are trained based on a pre-existing corpus of image matrices demonstrating each of a set of progressions and/or stages of heart failure, such as the four classes identified above. The set of heart failure classifiers 924, in some embodiments, include one or more ECG classifiers 924 trained using a truth base of ECG image matrices each produced using a same mapping of parameter values and pixel characteristic values as applied to producing the historic ECG image matrices 936*a-n*. Additionally, ECG image matrices of the truth base used in training the ECG classifier(s) 924 may have been produced using an ECG portion duration matching the ECG portion duration of the historic ECG image matrices 936*a-n*. In a further example, the ECG image matrices of the truth base used in training the ECG classifier(s) 924 may have been produced using a same deflection feature registration to align the plotting of the historic ECG image matrices 936*a-n*.

In some embodiments, the heart failure biomarker classifiers 924 include one or more cardio-vibrational classifiers 924 trained using a truth base of cardio-vibrational image matrices each produced using a same mapping of parameter values and pixel characteristic values as applied to producing the historic cardio-vibrational image matrices 938*a-n*. Additionally, cardio-vibrational image matrices of the truth base used in training the cardio-vibrational classifier(s) 924 may have been produced using a cardio-vibrational portion duration matching the cardio-vibrational portion duration of the historic cardio-vibrational image matrices 938*a-n*. In a further example, the cardio-vibrational image matrices of the truth base used in training the cardio-vibrational classifier(s) 924 may have been produced using a same deflection feature registration to align the plotting of the historic cardio-vibrational image matrices 938*a-n*.

In some embodiments, the heart failure biomarker classifiers 924 include one or more co-registered classifiers 924 trained using a truth base of ECG matrices co-registered with cardio-vibrational image matrices (e.g., aligned along a y-axis or an x-axis as a single training image to demonstrate commonalities in cardiac signatures between the two types of matrices). As discussed above, each image matrix of the truth base, prior to co-registration, may have been produced using a same mapping of parameter values and pixel characteristic values as applied to producing the historic image matrices 936*a-n* or 938*a-n*, a same portion duration as applied to producing the historic image matrices 936*a-n* or 938*a-n*, and or a same deflection feature for registering alignment between the historic ECG image matrices 936*a-n* and the historic cardio-vibrational image matrices 938*a-n*.

In some implementations, the heart failure biomarker classifiers 924 include separate cardiac risk biomarker classifiers trained from a truth base designed to identify each of class I HF, class II HF, class III HF, and class IV HF. Thus, the heart failure biomarker classifiers 924, in an illustrative example, may include an ECG class I HF classifier, an ECG class II HF classifier, an ECG class III HF classifier, an ECG class IV HF classifier, a cardio-vibrational class I HF classifier, a cardio-vibrational class II HF classifier, a cardio-vibrational class III HF classifier, a cardio-vibrational class IV HF classifier, a co-registered class I HF classifier, a co-registered class II HF classifier, a co-registered class III HF classifier, and/or a co-registered class IV HF classifier.

Each of the heart failure biomarker classifiers 924, in some embodiments, were trained in part using a portion of the historic ECG image matrices 936*a-n* and/or the historic cardio-vibrational image matrices 938*a-n*. For example, the heart failure biomarker classifiers 924 may be trained in part to identify a baseline (e.g., prior classification of heart failure) signature of the patient to better analyze trends in worsening of the heart failure condition.

In some embodiments, at least a portion of the heart failure progression machine learning engine(s) 922 include one or more deep neural network (DNN) models configured to apply at least a portion of the heart failure biomarker classifiers 924. In some embodiments, at least a portion of the heart failure progression machine learning engine(s) 922 include one or more convolution neural network (CCN) models configured to apply at least a portion of the heart failure biomarker classifiers 924. In some embodiments, at least a portion of the heart failure progression machine learning engine(s) 922 include one or more network in network (NiN) models configured to apply at least a portion of the heart failure biomarker classifiers 924. Other deep learning models may be applied, with the particular deep learning model being selected, in some examples, based in part on processing availability and storage size availability in the end system (e.g., a cloud network versus processing on a medical device), third party tool access (e.g., availability of cloud provider specialized tools and hardware for performing image classification), and/or processor type (e.g., GPU, CPU, FPGA, etc.).

The heart failure progression machine learning engine(s) 922, in some embodiments, are executed concurrently. For example, the heart risk learning engine(s) 902 may include a separate engine for each of at least class I, class II, class III, and class IV identification, with the separate engines executing in parallel to determine biomarkers indicative of each class or stage of heart failure. The positive identifiers (e.g., classifier matches), in some implementations, are combined as a heart failure classification 926. The heart failure classification 926, in some embodiments, is stored to a historic heart failure classifications repository 928 for future review. The heart failure classification 926, for example, may include a feature vector or binary code indicating a corresponding "match" or "no match" related to each of the heart failure biomarker classifiers 924. In another example, the heart failure classification 926 may include a nuanced analysis, including information regarding confidence levels associated with various matching heart failure biomarker classifiers 924. The heart failure progression learning engine(s) 922, in some implementations, apply weightings related to one or more of the heart failure biomarker classifiers 924 in determining the heart failure classification 926. The weightings may be based, in part, upon a confidence the heart failure progression machine learning engine(s) 922 have in the identified match for each of one or more of the heart failure biomarker classifiers 924. For example, in machine learning analysis, matches of a particular input to a classifier are associated with a score, or confidence rating, in how close the match appears. At some point, the confidence rating may be so low that the heart failure progression learning engine(s) 922 consider the outcome to be a non-match (e.g., 65% certainty, between 70% and 85% certainty, below 95% certainty, etc.). In other ranges, the confidence rating may be at a threshold for inclusion but weighted lower than a higher confidence rating. In an illustrative example, below 70% certainty may be considered a non-match, between 70% and 85% a possible match, between 85% and 95% a probable match, and over 95% a confident match. Each of possible, probable, and confident may be associated with a different weighting for formulating the heart failure classification 926.

In some implementations, the heart failure classification 926 is provided to a heart failure trend analysis engine 930 for analysis of the heart failure classification 926 in view of historic heart failure classification(s) 928 for the patient (e.g., obtained during a prior analysis, such as through the process 900 of FIG. 9A). This advantageously allows the process 920 to automatically analyze the patient for changes in classification indicative of heart failure worsening, leading to early identification of worsening heart failure condition and thus early intervention. The results of the comparison by the heart failure trend analysis engine 930 include heart failure trend metrics 932, for example identifying no change in class or stage of heart failure, a negative trend in heart failure progression, or a positive trend in heart failure progression. In some examples, a positive trend in heart failure progression can include decompensation and recovery of cardiac function in the heart failure patient.

The heart failure trend analysis engine 930 may combine comparison analysis of the heart failure classification 926 and the historic heart failure classification(s) 928 with analysis of historic ECG metrics 552*a-n* and historic cardio-vibrational metrics 554*a-n*, accessed from the metrics repository 556, to determine heart failure trend metrics 932 for the patient. The historic ECG metrics 552*a-n* and historic cardio-vibrational metrics 554*a-n*, for example, may include at least a most recent set of metrics 552, 554 as well as a prior set of metrics 552, 554 (e.g., from prior execution of the process 920 of FIG. 9B or the process 900 of FIG. 9A). The historic metrics 552*a-n* and/or 554*a-n*, in some examples, may include heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or a shape of morphology of the ECG information, cosine R-T, artificial pacing, QT interval, QT variability, T wave width, T wave alternans, T-wave variability, ST segment changes, S1, S2, S3, S4, electromechanical activation time (EMAT), average EMAT, percentage of EMAT (% EMAT), systolic dysfunction index (SDI), and/or left ventricular systolic time (LVST). The heart failure trend metrics 932, for example, may include differences or significant changes in one or more of the above identified metrics.

In some implementations, a heart failure trend report generation engine 934 combines the heart failure trend metrics 932 in a report for review by a clinician and/or patient.

The report 936, for example, may include one or more graphs and/or tables representing progressive changes in the historic metrics 552*a-n* and/or 554*a-n* as well as a present heart failure classification assessment.

In some implementations, the heart failure trend report generation engine 934 produces user interface display rendering instructions for rendering the heart failure trend report 936 as a graphic user interface (GUI) upon a display of a computing device for review by a user such as a clinician. In some implementations, the failure trend report 936 is generated by the heart failure trend report generation engine 934 as a report file, such as a portable document format (PDF) file or Visio spreadsheet. The heart failure trend report generation engine 934 may provide the report to a computer display, to a printer, or to an electronic communications contact (e.g., email address), in some examples.

In training the machine learning classifiers as described herein, a case-control cohort may be built of a large number of patients (e.g., between 5,000-10,000, or more) with demographic data including gender, age, and ICD code information. For example, these patients may be patients that have worn the LifeVest® wearable cardioverter defibrillator (WCD) device over a certain span of years (e.g., patients from between 2014 and 2020) and provided ambulatory ECG and cardio-vibrational recordings. In implementations, this training dataset can be enriched with information about which of these patients were shocked for sustained VT/VF (e.g., tachyarrhythmia SCA) within a certain time from initial wear (e.g., 72 hours, 1 week, 10 days, or 2 weeks). Controls can include patients who did not receive shocks but were matched to cases based on age, gender and initial wear time. During training, the machine learning classifiers can be based on a score characterizing likelihood of sudden cardiac arrest or other predetermined end point as described above.

A second training set can be built using a second cohort of a large number of patients (e.g., 15,000-20,000, or more) in a similar manner as described above for the first training set. Training Set 2 can be accrued to establish threshold for stratifying patients by their risk for adverse end points. In this example, the second training set can be used to establish threshold values from the models that optimizes sensitivity and specificity for detecting increased risk of the adverse end points.

In the foregoing manner, an ROC curve can be generated indicating acceptable thresholds for sensitivity and specificity, in accordance with a user's specifications. For example, a 92% specificity level may be chosen to reduce the potential for alarm fatigue and increase confidence in the risk status. In examples, the specificity that is set then determines the sensitivity.

In example advantages or benefits of the disclosure herein, as a first example, a risk status may be applied to ensuring patients already prescribed a medical device remain protected during periods of increased risk. Some patients may choose to end their medical device use within the first few days of wear (e.g., after only a week or two weeks). This may be a result of a lack of clear understanding of the risk they face and the related role of the wearable medical devices. Being able to identify patients who are at the highest level of risk who wish to end use prematurely may provide the caregiver an opportunity to engage the patient and ensure that they understand the importance of sudden cardiac risk protection. As a second advantage, a risk status may be applied to patients perceived as having lower sudden cardiac arrest risk, including patients with preserved ejection fraction, who are under ambulatory cardiac monitoring (e.g., Holter-type monitoring). Such patients may not otherwise be identified as such and can be switched over to a wearable cardioverter defibrillator for protection against sudden cardiac arrest.

The teachings of the present disclosure can be generally applied to external medical monitoring and/or treatment devices that include one or more sensors as described herein. Such external medical devices can include, for example, ambulatory medical devices as described herein that are capable of and designed for moving with the patient as the patient goes about his or her daily routine. An example ambulatory medical device can be a wearable medical device such as a wearable cardioverter defibrillator (WCD), an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as twenty-four hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other non-ECG physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

FIG. 10 illustrates an example component-level view of a medical device controller 1000 included in, for example, a wearable medical device. As further shown in FIG. 10, the therapy delivery circuitry 1002 can be coupled to one or more electrodes 1020 configured to provide therapy to the patient. For example, the therapy delivery circuitry 1002 can include, or be operably connected to, circuitry components that are configured to generate and provide an electrical therapeutic shock. The circuitry components can include, for example, resistors, capacitors, relays and/or switches, electrical bridges such as an h-bridge (e.g., including a number of insulated gate bipolar transistors or IGBTs), voltage and/or current measuring components, and other similar circuitry components arranged and connected such that the circuitry components work in concert with the therapy delivery circuitry and under control of one or more processors (e.g., processor 1018) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation shocks can be used to treat ventricular tachycardia and/or ventricular fibrillation.

For example, each defibrillation shock can deliver between 60 to 180 joules of energy. In some implementations, the defibrillating shock can be a biphasic truncated exponential waveform, whereby the signal can switch between a positive and a negative portion (e.g., charge directions). This type of waveform can be effective at defibrillating patients at lower energy levels when compared to other types of defibrillation shocks (e.g., such as monophasic shocks). For example, an amplitude and a width of the two phases of the energy waveform can be automatically adjusted to deliver a precise energy amount (e.g., 150 joules) regardless of the patient's body impedance. The therapy delivery circuitry 1002 can be configured to perform the switching and pulse delivery operations, e.g., under control of the processor 1018. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

In certain examples, the therapy delivery circuitry 1002 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

A data storage region 1004 can include one or more of non-transitory computer-readable media, such as flash memory, solid state memory, magnetic memory, optical memory, cache memory, combinations thereof, and others. The data storage 1004 can be configured to store executable instructions and data used for operation of the medical device controller 1000. In certain examples, the data storage 1004 can include executable instructions that, when executed, are configured to cause the processor 1018 to perform one or more operations. In some examples, the data storage 1004 can be configured to store information such as ECG data as received from, for example, a sensing electrode interface 1012.

In some embodiments, a network interface 1006 can facilitate the communication of information between the medical device controller 1000 and one or more other devices or entities over a communications network. For example, where the medical device controller 1000 is included in an ambulatory medical device, the network interface 1006 can be configured to communicate with a remote computing device such as a remote server or other similar computing device. In further embodiments, the remote computing device can be part of a remote data analytics system 1032. The network interface 1006 can include communications circuitry for transmitting data in accordance with a Bluetooth® or Zigbee® wireless standard for exchanging such data over short distances to an intermediary device 1034. In some examples, the intermediary device 1034 can be configured as a base station, a "hotspot" device, a smartphone, a tablet, a portable computing device, and/or other devices in proximity of the wearable medical device including the medical device controller 1000. The intermediary device(s) 1034 may in turn communicate the data to a remote server over a broadband cellular network communications link, such as the data analytics system 1032. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) 1034 may communicate with a remote server over a Wi-Fi® communications link based on the IEEE 802.11 standard.

In certain embodiments, a user interface 1008 can include one or more physical interface devices such as input devices, output devices, and combination input/output devices and a software stack configured to drive operation of the devices. These user interface elements can render visual (e.g. LEDs 1042), audio (e.g., speaker 1040), and/or tactile content. Thus, the user interface 1008 can receive input (e.g., via one or more control buttons 1044) or provide output, thereby enabling a user to interact with the medical device controller 1000.

The medical device controller 1000, in some embodiments, includes at least one power source (e.g., rechargeable battery) 1010 configured to provide power to one or more components integrated in the medical device controller 1000. The battery 1010 can include a rechargeable multi-cell battery pack. In one example implementation, the battery 1010 can include three or more 2200 mAh lithium ion cells that provide electrical power to the other device components within the medical device controller 1000. For example, the battery 1010 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 1000.

A sensor interface 1012, in some embodiments, includes physiological signal circuitry that is coupled to one or more sensors configured to monitor one or more physiological parameters of the patient. As shown, the sensors 1022, 1024, 1026, 1030 can be coupled to the medical device controller 1000 via a wired or wireless connection. The sensors can include one or more ECG sensing electrodes 1022 and non-ECG physiological sensors such as a vibration sensor 1024, tissue fluid monitor(s) 1026 (e.g., based on ultra-wide band RF devices), and motion sensor(s) 1030 (e.g., accelerometers, gyroscopes, and/or magnetometers). In some implementations, the sensors can include a number of conventional ECG sensing electrodes 1022 in addition to digital sensing electrodes 1022.

The sensing electrodes 1022 can be configured to monitor a patient's ECG information. For example, by design, the digital sensing electrodes 1022 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 1022 can be used with an electrolytic gel dispersed between the electrode surface and the patient's skin. In certain implementations, the electrodes 1022 can be dry electrodes that do not need an electrolytic material. As an example, such a dry electrode can be based on tantalum metal and having a tantalum pentoxide coating as is described above. Such dry electrodes can be more comfortable for long term monitoring applications.

The vibration sensor(s) 1024, in some implementations, can be configured to detect cardiac or pulmonary vibration information. For example, the vibration sensor(s) 1024 can detect a patient's heart valve vibration information. For example, the vibration sensor(s) 1024 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensor(s) 1024 can also be configured to detect heart wall motion, for instance, by placement of the sensor in the region of the apical beat. The vibration sensor(s) 1024 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on pulmonary vibrations produced within the lungs (e.g., stridor, crackle, etc.). The vibration sensor(s) 1024 can also include a multi-channel accelerometer, for example, a three-channel accelerometer configured to sense movement in each of three orthogonal axes such that patient movement/body position can be detected and correlated to detected cardio-vibrations information. The vibration sensor(s) 1024 can transmit information descriptive of the cardio-vibrations information to the sensor interface 1012 for subsequent analysis.

The tissue fluid monitor(s) 1026 can use radio frequency (RF) based techniques to assess fluid levels and accumulation in a patient's body tissue. For example, the tissue fluid monitor(s) 1026 can be configured to measure fluid content in the lungs, typically for diagnosis and follow-up of pulmonary edema or lung congestion in heart failure patients. The tissue fluid monitor(s) 1026 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitor(s) 1026 can transmit information descriptive of the tissue fluid levels to the sensor interface 1012 for subsequent analysis.

In certain implementations, a cardiac event detector 1016 can be configured to monitor a patient's ECG signal for an occurrence of a cardiac event such as an arrhythmia or other similar cardiac event. The cardiac event detector 1016 can be configured to operate in concert with the processor 1018 to execute one or more methods that process received ECG signals from, for example, the sensing electrodes 1022 and determine the likelihood that a patient is experiencing a cardiac event. The cardiac event detector 1016 can be implemented using hardware or a combination of hardware and software. For instance, in some examples, cardiac event detector 1016 can be implemented as a software component that is stored within the data storage 1004 and executed by the processor 1018. In this example, the instructions included in the cardiac event detector 1016 can cause the processor 1018 to perform one or more methods for analyzing a received ECG signal to determine whether an adverse cardiac event is occurring. In other examples, the cardiac event detector 1016 can be an application-specific integrated circuit (ASIC) that is coupled to the processor 1018 and configured to monitor ECG signals for adverse cardiac event occurrences. Thus, examples of the cardiac event detector 1016 are not limited to a particular hardware or software implementation.

In some implementations, the processor 1018 includes one or more processors (or one or more processor cores) that each are configured to perform a series of instructions that result in manipulated data and/or control the operation of the other components of the medical device controller 1000. In some implementations, when executing a specific process (e.g., cardiac monitoring), the processor 1018 can be configured to make specific logic-based determinations based on input data received and be further configured to provide one or more outputs that can be used to control or otherwise inform subsequent processing to be carried out by the processor 1018 and/or other processors or circuitry with which processor 318 is communicatively coupled. Thus, the processor 1018 reacts to specific input stimulus in a specific way and generates a corresponding output based on that input stimulus. In some example cases, the processor 1018 can proceed through a sequence of logical transitions in which various internal register states and/or other bit cell states internal or external to the processor 1018 can be set to logic high or logic low. As referred to herein, the processor 1018 can be configured to execute a function where software is stored in a data store coupled to the processor 1018, the software being configured to cause the processor 1018 to proceed through a sequence of various logic decisions that result in the function being executed. The various components that are described herein as being executable by the processor 1018 can be implemented in various forms of specialized hardware, software, or a combination thereof. For example, the processor 1018 can be a digital signal processor (DSP) such as a 24-bit DSP. The processor 1018 can be a multi-core processor, e.g., having two or more processing cores. The processor 1018 can be an Advanced RISC Machine (ARM) processor such as a 32-bit ARM processor or a 64-bit ARM processor. The processor 1018 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 1018 of the controller 1000 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 11A:
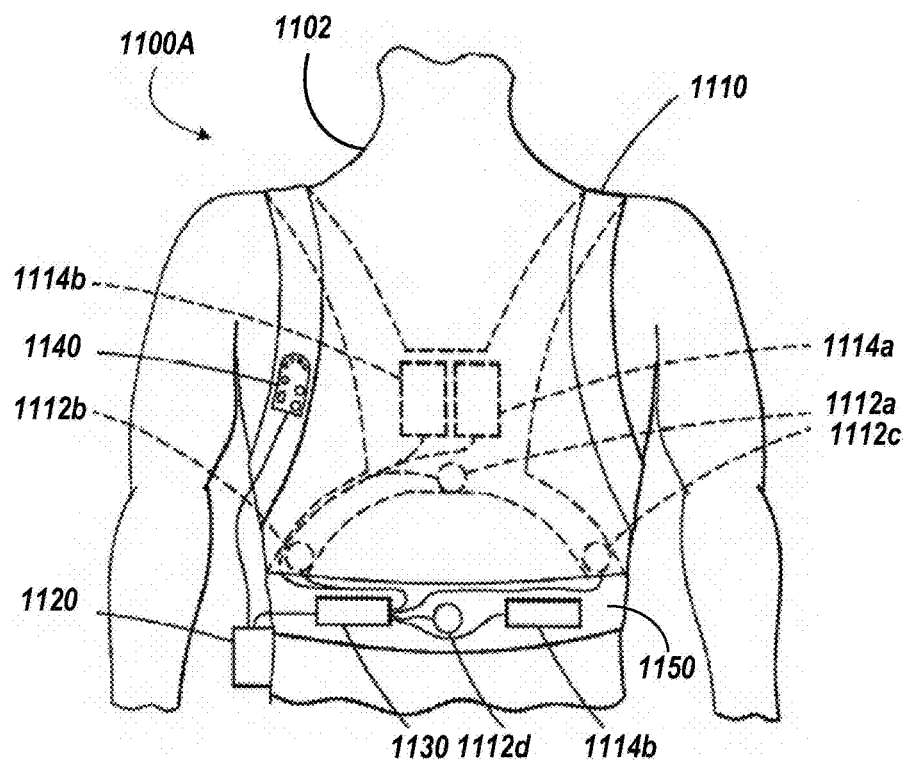
FIGS. 11A-11D illustrate example wearable medical devices for monitoring a cardiac condition of a patient.

FIG. 11A illustrates an example medical device 1100 that is external, ambulatory, and wearable by a patient 1102, and configured to implement one or more configurations described herein. For example, the medical device 1100 can be a non-invasive medical device configured to be located substantially external to the patient. Such a medical device 1100 can be, for example, an ambulatory medical device that is capable of and designed for moving with the patient as the patient goes about his or her daily routine. For example, the medical device 1100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1100 can include one or more of the following: a garment 1110, one or more ECG sensing electrodes 1112, one or more non-ECG physiological sensors such as the sensors 1024, 1026, 1030 described in relation to FIG. 10, one or more therapy electrodes 1114a and 1114b (collectively referred to herein as therapy electrodes 1114), a medical device controller 1120 (e.g., controller 1000 as described above in the discussion of FIG. 10), a connection pod 1130, a patient interface pod 1140, a belt 1150, or any combination of these. In some examples, at least some of the components of the medical device 1100 can be configured to be affixed to the garment 1110 (or in some examples, permanently integrated into the garment 1110), which can be worn about the patient's torso. In some implementations, at least a portion of the components of the medical device 1100 can be configured to be in wireless communication with other components of the medical device 1100. For example, the patient interface pod 1140 may be arranged as a remote control interface for use by the patient and in wireless communication with the medical device controller 1120.

The medical device controller 1120 can be operatively coupled to the sensing electrodes 1112, which can be affixed to the garment 1110, e.g., assembled into the garment 1110 or removably attached to the garment, for example using hook and loop fasteners, snaps, and/or Velcro. In some implementations, the sensing electrodes 1112 can be permanently integrated into the garment 1110. The medical device controller 1120 can be operatively coupled to the therapy electrodes 1114. For example, the therapy electrodes 1114 can also be assembled into the garment 1110, or, in some implementations, the therapy electrodes 1114 can be permanently integrated into the garment 1110. In an example, the medical device controller 1120 includes a patient user interface 1160 to allow a patient interface with the externally-worn device. For example, the patient can use the patient user interface 1160 to respond to activity related questions, prompts, and surveys as described herein.

Component configurations other than those shown in FIG. 11A are possible. For example, the sensing electrodes 1112 can be configured to be attached at various positions about the body of the patient 1102. The sensing electrodes 1112 can be operatively coupled to the medical device controller 1120 through the connection pod 1130. In some implementations, the sensing electrodes 1112 can be adhesively attached to the patient 1102. In some implementations, the sensing electrodes 1112 and at least one of the therapy electrodes 1114 can be included on a single integrated patch and adhesively applied to the patient's body.

The sensing electrodes 1112 can be configured to detect one or more cardiac signals. Examples of such signals include ECG signals and/or other sensed cardiac physiological signals from the patient. In certain examples, as described herein, the non-ECG physiological sensors 1113 such as accelerometers, vibrational sensors, RF-based sensors, and other measuring devices for recording additional non-ECG physiological parameters. For example, as described above, the non-ECG physiological sensors may be configured to detect other types of patient physiological parameters and acoustic signals, such as tissue fluid levels, cardio-vibrations, lung vibrations, respiration vibrations, and/or patient movement, etc.

In some examples, the therapy electrodes 1114 can also be configured to include sensors configured to detect ECG signals as well as other physiological signals of the patient. The connection pod 1130 can, in some examples, include a signal processor configured to amplify, filter, and digitize these cardiac signals prior to transmitting the cardiac signals to the medical device controller 1120. One or more of the therapy electrodes 1114 can be configured to deliver one or more therapeutic defibrillating shocks to the body of the patient 1102 when the medical device 1100 determines that such treatment is warranted based on the signals detected by the sensing electrodes 1112 and processed by the medical device controller 1120. Example therapy electrodes 1114 can include metal electrodes such as stainless-steel electrodes that include one or more conductive gel deployment devices configured to deliver conductive gel to the metal electrode prior to delivery of a therapeutic shock.

In some examples, the medical device 1100 can further includes one or more motion sensors such as accelerometers 1162. As shown in FIG. 11A, in some examples an accelerometer 1162 can be integrated into one or more of a sensing electrode 1112, a therapy electrode 1114, the medical device controller 1120, and various other components of the medical device 1100.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1114 and associated circuitry can be optionally decoupled from (or coupled to) or switched out of (or switched in to) the medical device 1100A. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 11B:
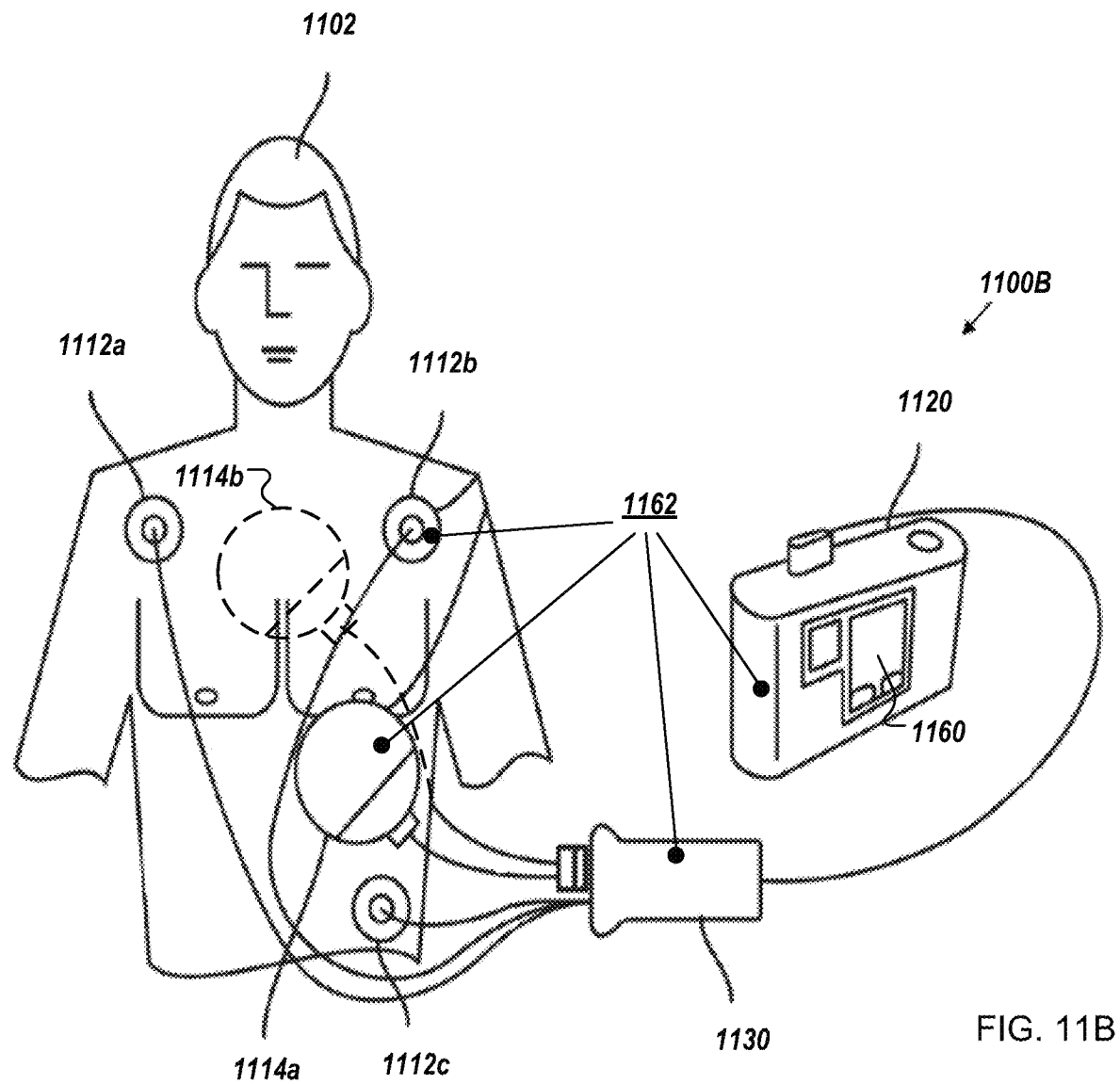

FIG. 11B illustrates a hospital wearable defibrillator 1100B that is external, ambulatory, and wearable by the patient 1102. Hospital wearable defibrillator 1100B can be configured in some implementations to provide pacing therapy, e.g., to treat bradycardia, tachycardia, and asystole conditions. The hospital wearable defibrillator 1100B can include one or more ECG sensing electrodes 1112, one or more therapy electrodes 1114, a medical device controller 1120 and a connection pod 1130. For example, each of these components can be structured and function as like number components of the medical device 1100A of FIG. 11A. For example, the electrodes 1112a-1112c, 1114a, 1114b can include disposable adhesive electrodes. For example, the electrodes 1112a, 1114a, 1114b can include sensing and therapy components disposed on separate sensing and therapy electrode adhesive patches.

In some implementations, both sensing and therapy components can be integrated and disposed on a same electrode adhesive patch that is then attached to the patient. For example, the front adhesively attachable therapy electrode 1114a attaches to the front of the patient's torso to deliver pacing or defibrillating therapy. Similarly, the back adhesively attachable therapy electrode 1114b attaches to the back of the patient's torso. In an example scenario, at least three ECG adhesively attachable sensing electrodes 1112a-1112c can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1160 can be configured to interact with a user other than the patient, e.g., a nurse, for device-related functions such as initial device baselining, setting and adjusting patient parameters, and changing the device batteries.

In some examples, the hospital wearable defibrillator 1100B can further include one or more motion sensors such as accelerometers 1162. As shown in FIG. 11B, in some examples an accelerometer 1162 can be integrated into one or more of a sensing electrode 1112a (e.g., integrated into the same patch as the sensing electrode), a therapy electrode 1114a (e.g., integrated into the same patch as the therapy electrode), the medical device controller 1120, the connection pod 1130, and various other components of the hospital wearable defibrillator 1100B.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 11B.

Figure 11C:
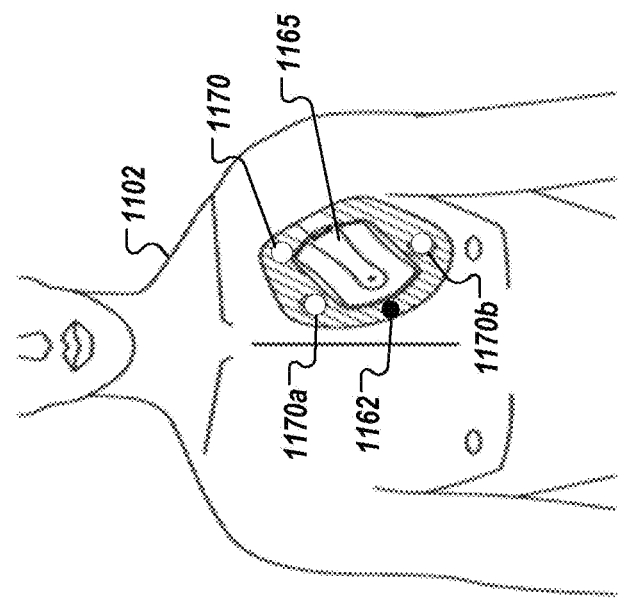
Figure 11C:
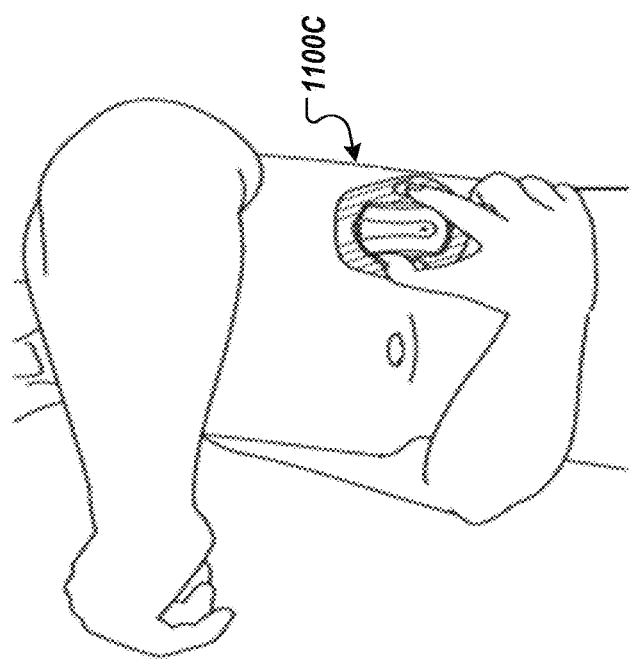
Figure 11D:
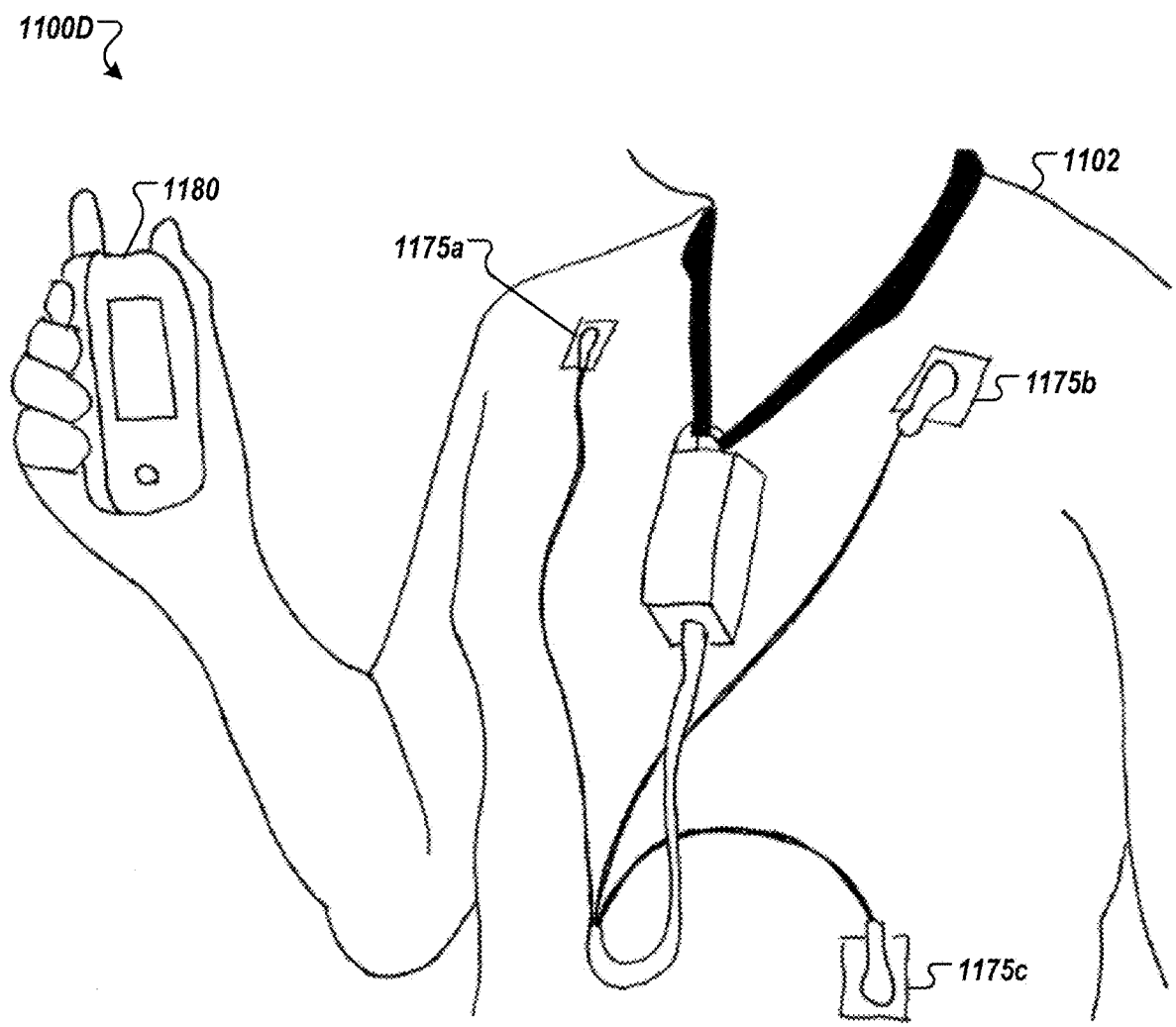

FIGS. 11C and 11D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 11C, an example wearable patient monitoring device 1100C can include tissue fluid monitors 1165 that use RF based techniques to assess fluid levels and accumulation in a patient's body tissue. Such tissue fluid monitors 1165 can be configured to measure fluid content in the lungs, typically for diagnosis and follow-up of pulmonary edema or lung congestion in heart failure patients. The tissue fluid monitors 1165 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1100C may be a cardiac monitoring device that also includes digital sensing electrodes 1170a, 1170b for sensing ECG activity of the patient. Device 1100C can pre-process the ECG signals via one or more ECG processing and/or conditioning circuits such as an ADC, operational amplifiers, digital filters, signal amplifiers under control of a microprocessor. Device 1100C can transmit information descriptive of the ECG activity and/or tissue fluid levels via a network interface to a remote server for analysis. Additionally, in certain implementations, the device 1100C can include one or accelerometers 1162 for measuring motion signals as described herein.

Referring to FIG. 11D, another example wearable cardiac monitoring device 1100D can be attached to a patient 1102 via at least three adhesive digital cardiac sensing electrodes 1175a-c disposed about the patient's torso. Additionally, in certain implementations, the device 1100D can include one or accelerometers (not illustrated) integrated into, for example, one or more of the digital sensing electrodes for measuring motion signals as described herein.

Cardiac devices 1100C and 1100D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause(s), and/or heart palpitations. For example, such patients may be prescribed a cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 11A-11D) can communicate with a remote server via an intermediary or gateway device 1180 such as that shown in FIG. 11D. For instance, devices such as shown in FIGS. 11A-D can be configured to include a network interface communications capability as described herein in reference to, for example, FIG. 10.

Additionally, the devices 1100A-D described herein in relation to FIGS. 11A-11D can be configured to include one or more vibrational sensors as described herein for collecting signals for use in producing cardio-vibrational image matrices.

Reference has been made to illustrations representing methods and systems according to implementations of this disclosure. Aspects thereof may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors, for example on one or more physical computing systems such as a computer farm or a cloud drive.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the computing device to perform, in some examples, the method 100 of FIG. 1, the method 300 of FIGS. 3A and 3B, the process flow 500 of FIG. 5, the process flow 600 of FIG. 6, the process flow 800 of FIG. 8, the process flow 900 of FIG. 9A, and/or the process flow 920 of FIG. 9B.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include WiFi®, Bluetooth®, Zigbee®, or another wireless form of communication. The network, for example, may support communications between the medical device 502 and one or more of the engines as described in relation to FIG. 5 or between the graphic user interface generation engine and the computing device having the display 612, as described in relation to FIG. 6. The network may support communications between the medical device controller 1000 and the data analytics system 1032 and/or the intermediate device 1034 as described in relation to FIG. 10.

The computing device further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display. The display controller and display may enable presentation of the screen shots illustrated, in some examples, in FIGS. 2A, 2B, 4, 7A, and 7B.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™, may be used perform at least portions of methods or algorithms detailed above. The processes associated with the methods described herein can be executed on a computation processor, of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google Cloud Storage, may store processed and unprocessed data supplied by systems described herein. For example, the contents of the data repository 512, image matrix repository 540, mappings of parameter values and pixel characteristic values 536, and/or metrics repository 556 of FIG. 5, the arrhythmia classifiers 804 and/or arrhythmia classifications 814 of FIG. 8, the cardiac risk biomarker classifiers 904, patient demographic information 910, and/or patient physiological metrics 916 of FIG. 1, and/or the heart failure classifiers 924, historic heart failure classifications 928, and/or historic image matrix repository 940 may be maintained in a database structure.

The systems described herein may communicate with the cloud computing environment through a secure gateway. In some implementations, the secure gateway includes a database querying interface, such as the Google BigQuery platform. The data querying interface, for example, may support access by the ECG signal graph generation engine(s) 602 and/or the cardio-vibrational signal graph generation engine(s) 604 to the data repository 512, access by the image matrix graph generation engine(s) to the image matrix repository, and/or access by the metrics presentation engine(s) 608 to the metrics repository 556 as described in relation to FIG. 6. The data querying interface, in another example, may support access by the arrhythmia machine learning engine(s) 802 to the image matrix repository 540 and/or access by the medical device action determination engine 808 to the metrics repository 556 as described in relation to FIG. 8. In a further example, the data querying interface may support access by the heart risk machine learning engine(s) 902 to the image matrix repository 540 and/or access by the heart risk analysis engine 908 to one or more of the metrics repository 556, the patient demographic information 910, and/or the patient physiological metrics 916, as described in relation to FIG. 9A. The data querying interface, in an additional example, may support access by the heart failure progression machine learning engine(s) 922 to the historic image matrix repository 940 and/or the heart failure trend analysis engine 930 to the metrics repository 556 and/or the historic heart failure classifications 928, as described in relation to FIG. 9B.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for monitoring a progression of a cardiac disease in a patient by providing cardio-vibrational image matrices generated using sensor data supplied by a wearable cardiac monitoring device, the method comprising:
   receiving, from the wearable cardiac monitoring device, a plurality of cardio-vibrational signals obtained by at least one vibrational sensor monitoring a heart of the patient;
   storing, to a non-volatile computer-readable storage medium, the plurality of cardio-vibrational signals;
   accessing the plurality of cardio-vibrational signals;
   generating, by processing circuitry from the plurality of cardio-vibrational signals, cardio-vibrational measurements of a predetermined duration, the cardio-vibrational measurements comprising at least a plurality of S1 peaks and a plurality of S2 peaks; and
   transforming, by the processing circuitry, the cardio-vibrational measurements of the predetermined duration into a cardio-vibrational image matrix, wherein transforming comprises
      segmenting the cardio-vibrational measurements of the predetermined duration into a plurality of adjacent cardiac portions each having a duration smaller than the predetermined duration, and
      plotting the plurality of adjacent cardiac portions using a plurality of pixel characteristic values mapped to parameter values of corresponding cardio-vibrational measurements to produce the cardio-vibrational image matrix, wherein plotting comprises
         on one axis, a time progression of the plurality of adjacent cardiac portions, and
         on another axis, the pixel characteristic values of each portion of the plurality of adjacent cardiac portions, wherein the pixel characteristic values of each respective portion comprise values representing at least an S1 parameter value corresponding to a respective S1 peak of the plurality of S1 peaks, and an S2 parameter value corresponding to a respective S2 peak of the plurality of S2 peaks, such that the cardio-vibrational image matrix represents, along the time progression of the plurality of adjacent cardiac portions, visible differences in timing and/or intensity of at least the S1 parameter values of the cardiac portions and the S2 parameter values of the cardiac portions;
   outputting the cardio-vibrational image matrix as an image file;
   using the image file, monitoring the progression of the cardiac disease in the patient by confirming, through analyzing the cardio-vibrational image matrix, presence of an arrhythmia initially detected using ECG analysis of ECG measurements gathered by the wearable cardiac monitoring device; and after confirming the presence of the arrhythmia, initiating a treatment routine by the wearable cardiac monitoring device, wherein the treatment routine comprises an electrical shock therapy.

2. The method of claim 1, wherein each of the plurality of pixel characteristic values comprises at least one of a pixel intensity or a pixel hue.

3. The method of claim 1, wherein the parameter values comprise at least one of an amplitude, a phase, or a magnitude.

4. The method of claim 1, wherein the predetermined duration comprises at least one of around 15 seconds, around 30 seconds, around 45 seconds, around 90 seconds, around 120 seconds, around 2 minutes, around 3 minutes, around 10 minutes, between around 15 seconds and around 30 seconds, between around 30 seconds and around 45 seconds, between around 45 seconds and around 60 seconds, between around 60 seconds and around 90 seconds, between around 90 seconds and around 120 seconds, between around 2 minutes and around 3 minutes, or between around 3 minutes and around 10 minutes.

5. The method of claim 1, wherein the duration smaller than the predetermined duration comprises at least one of around 100 milliseconds, around 1000 milliseconds, around 1 second, around 2 seconds, around 5 seconds, around 10 seconds, between around 1 millisecond and around 100 milliseconds, between around 100 milliseconds and around 1000 milliseconds, between around 1 second and around 2 seconds, between around 2 seconds and around 5 seconds, or between around 5 seconds and around 10 seconds.

6. The method of claim 1, wherein each portion of the plurality of adjacent cardiac portions comprises at least two S1 peaks of the plurality of S1 peaks and at least two S2 peaks of the plurality of S2 peaks.

7. The method of claim 1, wherein plotting the plurality of adjacent cardiac portions comprises plotting the pixel characteristic values of each portion vertically along a y-axis and plotting the time progression of the plurality of adjacent cardiac portions horizontally along an x-axis.

8. The method of claim 7, wherein the cardio-vibrational image matrix represents, along the x-axis, visible differences in the timing and/or the pixel characteristic values of a portion of the plurality of S1 peaks and a portion of the plurality of S2 peaks.

9. The method of claim 1, further comprising:
prior to the transforming, registering, by the processing circuitry, a time scale of the cardio-vibrational measurements of the predetermined duration with a plurality of R-peaks of an ECG reading of the patient obtained during the predetermined duration;
wherein the segmenting comprises segmenting at least in part according to the registering.

10. The method of claim 1, further comprising applying, by the processing circuitry to the cardio-vibrational image matrix, a smoothing algorithm to sets of proximately located pixel characteristic values of the plurality of pixel characteristic values, wherein each set of proximately located pixel characteristic values are proximately located in a plotting position in the cardio-vibrational image matrix.

11. The method of claim 1, wherein the plurality of pixel characteristic values comprises between around at least 3 and 16 different colors.

12. The method of claim 1, further comprising transmitting, by the processing circuitry, the cardio-vibrational image matrix to a remote server.

13. The method of claim 1, further comprising:
applying, by the processing circuitry, the cardio-vibrational image matrix to at least one machine learning classifier to determine a present classification of a plurality of classifications of at least one cardiac risk biomarker; and
generating, by the processing circuitry using the present classification, a prediction of future potential outcome related to the at least one cardiac risk biomarker.

14. A system for monitoring a progression of a cardiac disease in a patient by providing cardio-vibrational image matrices generated using sensor data supplied by a wearable cardiac monitoring device, the system comprising:
a non-volatile computer-readable storage medium configured to store a plurality of cardio-vibrational measurements; and
a plurality of operations stored as a plurality of computer executable instructions to a non-transitory computer-readable media and/or encoded in hardware logic, wherein the plurality of operations is configured to
receive, from the wearable cardiac monitoring device, a plurality of cardio-vibrational signals obtained by at least one vibrational sensor monitoring a heart of the patient,
store, to the non-volatile computer-readable storage medium, the plurality of cardio-vibrational signals,
access the plurality of cardio-vibrational signals,
generate, from the plurality of cardio-vibrational signals, cardio-vibrational measurements of a predetermined duration, the cardio-vibrational measurements comprising at least a plurality of S1 peaks and a plurality of S2 peaks, wherein the cardio-vibrational measurements are stored to the non-volatile computer-readable storage medium;
transform the cardio-vibrational measurements of the predetermined duration into a cardio-vibrational image matrix, wherein transforming comprises
segmenting the cardio-vibrational measurements of the predetermined duration into a plurality of adjacent cardiac portions each having a duration smaller than the predetermined duration, and
plotting the plurality of adjacent cardiac portions using a plurality of pixel characteristic values mapped to parameter values of corresponding cardio-vibrational measurements to produce the cardio-vibrational image matrix, wherein plotting comprises
on one axis, a time progression of the plurality of adjacent cardiac portions, and
on another axis, the pixel characteristic values of each portion of the plurality of adjacent cardiac portions, wherein the pixel characteristic values of each respective portion comprise values representing at least an S1 parameter value corresponding to a respective S1 peak of the plurality of S1 peaks, and an S2 parameter value corresponding to a respective S2 peak of the plurality of S2 peaks, such that the cardio-vibrational image matrix represents, along the time progression of the plurality of adjacent cardiac portions, visible differences in timing and/or intensity of at least the S1 parameter values of the cardiac portions and the S2 parameter values of the cardiac portions; and
output the cardio-vibrational image matrix for use in monitoring for an arrhythmia condition in the patient, wherein the monitoring comprises identifying in real-time, by analyzing the cardio-vibrational image matrix, an existence or a non-existence of the arrhythmia condition, and
responsive to identifying the existence of the arrhythmia condition, providing indication of the existence of the arrhythmia condition for use by a controller of the wearable cardiac monitoring device in initiating a treatment routine, wherein the treatment routine comprises an electrical shock therapy.

15. The system of claim 14, wherein each of the plurality of pixel characteristic values comprises at least one of a pixel intensity or a pixel hue.

16. The system of claim 14, wherein the parameter values comprise at least one of an amplitude, a phase, or a magnitude.

17. The system of claim 14, wherein the predetermined duration comprises at least one of around 15 seconds, around 30 seconds, around 45 seconds, around 90 seconds, around 120 seconds, around 2 minutes, around 3 minutes, around 10 minutes, between around 15 seconds and around 30 seconds, between around 30 seconds and around 45 seconds, between around 45 seconds and around 60 seconds, between around 60 seconds and around 90 seconds, between around 90 seconds and around 120 seconds, between around 2 minutes and around 3 minutes, or between around 3 minutes and around 10 minutes.

18. The system of claim 14, wherein each portion of the plurality of adjacent cardiac portions comprises at least two S1 peaks of the plurality of S1 peaks and at least two S2 peaks of the plurality of S2 peaks.

19. The system of claim 14, wherein plotting the plurality of adjacent cardiac portions comprises plotting the pixel characteristic values of each portion vertically along a y-axis and plotting the time progression of the plurality of adjacent cardiac portions horizontally along an x-axis.

20. The system of claim 19, wherein the cardio-vibrational image matrix represents, along the x-axis, visible differences in the timing and/or the pixel characteristic values of a portion of the plurality of S1 peaks and a portion of the plurality of S2 peaks.

21. The system of claim 14, wherein the plurality of operations is configured to, prior to the transforming, register a time scale of the cardio-vibrational measurements of the predetermined duration with a plurality of R-peaks of an ECG reading of the patient obtained during the predetermined duration,
wherein the segmenting comprises segmenting at least in part according to the registering.

22. The system of claim 14, wherein the plurality of pixel characteristic values comprises between around at least 3 and 16 different colors.

23. The system of claim 14, wherein the wearable cardiac monitoring device comprises a cardiac monitor and associated plurality of ECG electrodes.

24. The system of claim 14, wherein the wearable cardiac monitoring device comprises a wearable cardioverter defibrillator.

25. The system of claim 14, wherein the plurality of operations is configured to transmit the cardio-vibrational image matrix to a remote server.

26. The system of claim 14, wherein the plurality of operations is configured to:
apply the cardio-vibrational image matrix to at least one machine learning classifier to determine a present classification of a plurality of classifications of at least one cardiac risk biomarker; and
generate, using the present classification, a prediction of future potential outcome related to the at least one cardiac risk biomarker.

27. A system for monitoring a progression of a cardiac disease in a patient by providing cardio-vibrational image matrices generated using sensor data supplied by a wearable cardiac monitoring device, the system comprising:
a non-volatile computer-readable storage medium configured to store a plurality of cardio-vibrational measurements;
at least one machine learning classifier trained to identify a plurality of classifications of at least one cardiac risk biomarker; and
a plurality of operations stored as a plurality of computer executable instructions to a non-transitory computer-readable media and/or encoded in hardware logic,
wherein the plurality of operations is configured to
receive, from the wearable cardiac monitoring device, a plurality of cardio-vibrational signals obtained by at least one vibrational sensor monitoring a heart of the patient,
store, to the non-volatile computer-readable storage medium, the plurality of cardio-vibrational signals,
access the plurality of cardio-vibrational signals,
generate, from the plurality of cardio-vibrational signals, cardio-vibrational measurements of a predetermined duration, the cardio-vibrational measurements comprising at least a plurality of S1 peaks and a plurality of S2 peaks, wherein the cardio-vibrational measurements are stored to the non-volatile computer-readable storage medium,
transform the cardio-vibrational measurements of the predetermined duration into a cardio-vibrational image matrix, wherein transforming comprises
segmenting the cardio-vibrational measurements of the predetermined duration into a plurality of adjacent cardiac portions each having a duration smaller than the predetermined duration, and
plotting the plurality of adjacent cardiac portions using a plurality of pixel characteristic values mapped to parameter values of corresponding cardio-vibrational measurements to produce the cardio-vibrational image matrix, wherein plotting comprises
on one axis, a time progression of the plurality of adjacent cardiac portions, and
on another axis, the pixel characteristic values of each portion of the plurality of adjacent cardiac portions, wherein the pixel characteristic values of each respective portion comprise values representing at least an S1 parameter value corresponding to a respective S1 peak of the plurality of S1 peaks, and an S2 parameter value corresponding to a respective S2 peak of the plurality of S2 peaks, such that the cardio-vibrational image matrix represents, along the time progression of the plurality of adjacent cardiac portions, visible differences in timing and/or intensity of at least the S1 parameter values of the cardiac portions and the S2 parameter values of the cardiac portions,
output the cardio-vibrational image matrix as an image file,
apply the image file of the cardio-vibrational image matrix to the at least one machine learning classifier to determine a present classification of the plurality of classifications of the at least one cardiac risk biomarker, and responsive to determining the present classification corresponds to a type of an arrhythmia condition, causing the wearable cardiac monitoring device to initiate a treatment routine, wherein the treatment routine comprises an electrical shock therapy.

28. The system of claim 27, wherein the wearable cardiac monitoring device comprises at least one of:
   a cardiac monitor and associated plurality of ECG electrodes; or
   a wearable cardioverter defibrillator and associated plurality of ECG and therapy electrodes.

29. The system of claim 27, wherein the plurality of operations is configured to transmit the cardio-vibrational image matrix to a remote server.

30. The system of claim 27, wherein plotting the plurality of adjacent cardiac portions comprises plotting the pixel characteristic values of each portion vertically along a y-axis and plotting the time progression of the plurality of adjacent cardiac portions horizontally along an x-axis.

* * * * *